United States Patent
Park et al.

(10) Patent No.: US 8,604,274 B2
(45) Date of Patent: Dec. 10, 2013

(54) PLANTS HAVING ENHANCED YIELD-RELATED TRAITS AND A METHOD FOR MAKING THE SAME

(75) Inventors: Soon Ju Park, Seoul (KR); Yang Do Choi, Seoul (KR); Chang-Deok Han, Seoul (KR)

(73) Assignees: CropDesign N.V. (BE); Crop Functional Genomics Center (KR)

( * ) Notice: Subject to any disclaimer, the term of this patent is extended or adjusted under 35 U.S.C. 154(b) by 612 days.

(21) Appl. No.: 12/670,027

(22) PCT Filed: Jul. 25, 2008

(86) PCT No.: PCT/EP2008/059764
§ 371 (c)(1),
(2), (4) Date: Jan. 21, 2010

(87) PCT Pub. No.: WO2009/016104
PCT Pub. Date: Feb. 5, 2009

(65) Prior Publication Data
US 2010/0199381 A1    Aug. 5, 2010

Related U.S. Application Data

(60) Provisional application No. 60/969,996, filed on Sep. 5, 2007.

(30) Foreign Application Priority Data

Jul. 27, 2007   (EP) .................................... 07113355

(51) Int. Cl.
*C12N 15/82*    (2006.01)
*C12N 15/63*    (2006.01)

(52) U.S. Cl.
USPC .......................................... 800/278; 435/468

(58) Field of Classification Search
None
See application file for complete search history.

(56) References Cited

U.S. PATENT DOCUMENTS

2006/0123505 A1 *   6/2006   Kikuchi et al. ............... 800/278

FOREIGN PATENT DOCUMENTS

| EP | 1 033 405 A2 | | 9/2000 |
|---|---|---|---|
| WO | WO 2004/035798 | * | 4/2004 |
| WO | WO-2004/035798 A2 | | 4/2004 |
| WO | WO 2004035798 A2 | * | 4/2004 |
| WO | WO-2007/078280 A2 | | 7/2007 |

OTHER PUBLICATIONS

Doerks et al., (TIG, 14:248-250, 1998).*
Smith et al. (Nature Biotechnology, 15:1222-1223, 1997).*
Bork et al. (TIG, 12:425-427, 1996).*
Wells, Biochemistry 29:8509-8517, 1990.*
Ngo et al., (The Protein Folding Problem and Tertiary Structure Prediction, K. Merz., and S. Le Grand (eds.) pp. 492-495,1994).*
Keskin et al. (Protein Science, 13:1043-1055, 2004).*
Thornton et al. (Nature structural Biology, structural genomics supplement, Nov. 2000).*
Irvine et al. (Int. J. Dev. Biol., 48:1065-1077, 2004).*
Maniatis et al. (Molecular Cloning: A Laboratory Manual, Cold Spring Harbor Laboratory, 1982; see in particular pp. 387-389.*
Buell et al. (NCBI, GenBank Sequence Accession No. Q7Y1L6; Published Nov. 2006).*
Hong, F., et al., "Overexpression of the rFCA RNA Recognition Motif Affects Morphologies Modifications in Rice (*Oryza sativa* L.)", Bioscience Reports, 2007, vol. 27, No. 4-5, pp. 225-234.
Burd, C. G., et al., "Conserved Structures and Diversity of Functions of RNA-Binding Proteins", Science, 1994, vol. 265, pp. 615-621.

\* cited by examiner

*Primary Examiner* — Vinod Kumar
(74) *Attorney, Agent, or Firm* — Novak Druce Connolly Bove + Quigg LLP

(57) ABSTRACT

The present invention relates generally to the field of molecular biology and concerns a method for enhancing various economically important yield-related traits in plants. More specifically, the present invention concerns a method for enhancing yield-related traits in plants by modulating expression in a plant of a nucleic acid encoding a GSBP-like polypeptide (GSBP: GT-Pase activating protein SH3 domain binding Protein). The present invention also concerns plants having modulated expression of a nucleic acid encoding a GSBP-like polypeptide, which plants have enhanced yield-related traits relative to control plants.

12 Claims, 22 Drawing Sheets

MAVQAGTPATPISPQVISGAFVQQYYHILHETPDQVYKFYQDASIVGRPDSNGVMK YVSTTADINKTILSMDFSNYLTEIETADAQLSHQDGVLIVVTGSLTSEGICRRFTQ SFFLAPQESGGYVVLNDIFRFIVERPPVAISQVSQENENNQNTATLPETDPNPAGD GMISEPVAVENNVAEGEVTNSTVDGTSIENNATAAVEPPVQMTKEEPRKISVAAPP PPAQKDVTKKSYASIVKVMKEVSLTPVVKPKPAPKHVVKTVEASEKPSVKSSQTVE ITPNDNNDAENNTSNDEQGY<u>SVFVKSLPHNVTVQTVEEEFKKFGAIKPGGIQVRNN KIDRFCFGFIEFESQQSMQAAIEASPIHMGGKEVFVEEKRTTTRVVNGVVIT*RGD*N</u> GNAGGGGRYQSGRGGY*RGD*NFRGRGGGYANSGNYRGGDNFSRRNDLRNRNEFSGRG RGPPPGNGYQNNGFHPARPFQNGNGRFTRVNGPRQTPVAA

FIGURE 1

CLUSTAL W (1.83) multiple sequence alignment

```
EAZ27342         ------------------------------------------------------------
EAY90482         MPSRMMQAFAQEASDFDRQMGCMAGMFQIFDRRRLLTARQRGGARGTAPPGHVLPNSNSN
GSBP-LIKE        ------------------------------------------------------------
NP001060210      ------------------------------------------------------------
EAZ04627         ------------------------------------------------------------
NP001052571      ------------------------------------------------------------
EAY93771         ------------------------------------------------------------
NP200906         ------------------------------------------------------------
NP189151         ------------------------------------------------------------
BAE71222         ------------------------------------------------------------
Q1SBN7           ------------------------------------------------------------
NP178462         ------------------------------------------------------------
BAE71299         ------------------------------------------------------------
CAE03370         ------------------------------------------------------------
XP001110514      ------------------------------------------------------------
EAW61662         -------------------------------------------------------MQLQPT

EAZ27342         ------------------------MAVQAGTPATPISPQVISGAFVQQYYHILHETP
EAY90482         VSIQNPVASNNTLVYDDDARDGAIGFPMAVQAGTPATPISPQVISGAFVQQYYHILHETP
GSBP-LIKE        ------------------------MAVQAGTPATPISPQVISGAFVQQYYHILHETP
NP001060210      ------------------------MAMQVGESVAPLSPQMIGNAFVQQYYNVLHSSP
EAZ04627         ------------------------MAMQVGESVAPLSPQTIGNAFVQQYYNVLHSSP
NP001052571      ---------------MASPPPPPPSAAAPGSPPSAQVVGNAFVHQYYNILHQSP
EAY93771         ------------------------MAQQEASPSPGAEVVGRAFVEQYYHILHQSP
NP200906         ------------------------MAMLGAQQVPAAACTPDMVGNAFVPQYYHILHQSP
NP189151         ------------------------MAVSDGVQTPTPQVVGNAFVEQYYSILHQDP
BAE71222         ---------------------------MVGNAFVEQYYSILHRDP
Q1SBN7           ------------------MTPESNAPSVDPQFVGNGFVQEYYNHLYDST
NP178462         ---------------------MASSYPGSVSAAQVGSYFVGQYYOVLRQQP
BAE71299         ------------MGGRYHMEMPTGMRELDRVQQQIASHPYAFEVCSYFLQGYYNVIANSP
CAE03370         ------------------------MVMEKPSPLLVGREFVRQYYTLLNQAP
XP001110514      ------------------------MVMEKPSPLLVGREFVRQYYTLLNQAP
EAW61662         SHCSFMRASELEPLGQAVPKFLTLRNCVELTKAMVMEKPSPLLVGREFVRQYYTLLNQAP
```

```
EAZ27342         GIQVRNNKIDRFCFGFIEFESQQSMQAAIEASP---IHMGGKEVFVEEKRTTTRVVNGVV
EAY90482         GIQVRNNKIDRFCFGFIEFESQQSMQAAIEASP---IHMGGKEVFVEEKRTTTRVVNGVV
GSBP-LIKE        GIQVRNNKIDRFCFGFIEFESQQSMQAAIEASP---IHMGGKEVFVEEKRTTTRVVNGVV
NP001060210      GIQVRHRQPDGFCFGFVEFESRQSMLAAIEASP---VSIGSKASIVEEKRTTTRVVNGVT
EAZ04627         GIQVRHRQPDGFCFGFVEFESRQSMLAAIEASP---VSIGSKASIVEEKRTTTRVVNGVT
NP001052571      GIQVRSHKIQGFCYGFVEFEDPSSVQSAIAGSP----VTISDRQCYVEEKRTAGSRGG---
EAY93771         GIQVRSHKIQGFCYGFVEFEDPSSVQSAIAGSP----VTISDRQCYVEEKRTAGSRGG---
NP200906         GIQVRSNKQQGFCFGFVEFETSSGKQSALEASP----VTIGDRQAVVEEKKTNSRGGG---
NP189151         GIQVRSQK--GFCFGFVEFESASSMQSAIEASP----VMLNGHKVVVEEKRSTAR-GN---
BAE71222         GIQVRSNK--GSCFGFVEFESAASLQSALEASPP--VMLDNRRLSIEERR---
Q1SBN7           GIQVRSNK--GSCFGFVEFESAASMQSALEASPP--VMLDNRRLSIEERR---
NP178462         GIQVRSYPEKKNCIGFVAFENGEAVKNVFQAHRESPIRIGNRRASIEEKRGGNNQNG---
BAE71299         ----GIFEIGVCYAFVEFEDVVGVQNALQASP----IQLAGRQIYIEERRPSS---
CAE03370         GVAIRSRKEAGIFFGFVEYEDMSGIHNALRASP----IELNGRLIHVEERRQIYR---
XP001110514      RINSGGKLP---NFGFVVFDDSEPVQKVLSNRP---IMFRGEVRLNVEEKTRAAREG---
EAW61662         RINSGGKLP---NFGFVVFDDSEPVQKVLSNRP---IMFRGEVRLNVEEKTRAAREG---
                                 *:               ::              *   *: ::

EAZ27342         ITRGDNGNGAGGGGGRYQSGRGGYRGDNFRGRGGGYANSGNYRGGDNFSRRNDLRNRNEFSG
EAY90482         ITRGDNGNGAGGGGGRYQSGRGGYRGDNFRGRGGGYANSGNYRGGDNFSRRNDLRNRNEFSG
GSBP-LIKE        ITRGDNGNGAGGGGGRYQSGRGGYRGDNFRGRGGGYANSGNYRGGDNFSRRNDLRNRNEFSG
NP001060210      HIENNGNAARGRFQQDNRGGGYRGDNFRGREAGFVNNGNYRDGD--NMRNGFRNQNEYSG
EAZ04627         HIENNGNAWGGRFQQDNRGGGYRGDNFRGREAGFVNNGNYRDGD--NLRNRFRNQNEYSG
NP001052571      ----GRGRFAPGRGGNFRGEGMRGRGNYTGGRG--YGRGEFNYRSDYGGRGAGRGG
EAY93771         ----GRGRFAPGRGGNFRGEGMRGRGNYTGGRG--YGRGEFNYRSDYGGRGAGRGG
NP200906         ----NNG---GSRGRYFSGRGSFRNESFKGGRG--GGGRGGYGRGGGEFSGRPKSS
NP189151         ----YRGRSTFGVNTGYRNEGGRGRGSFGGGRGGYGRTDFNGYGNNRGNNRGGYA
BAE71222         ---------GRGGYRNDRNDNFRGRGNFGGGRG----GGFNGRNDFDRRG-EFSG
Q1SBN7           ---------GRSGYRNDRNDNFRGRGNFGGGRG----GGFNGRNDFERRGGEFSG
NP178462         -------NRVSTRNNSGYKNEDGFRRDGYKPRGSGVNGGRGYGRRNSESNGDGKAY
BAE71299         -------GGAARGRGRGRGRGRGRGR-------PADFSRGQSGGRYDG------DYATR
CAE03370         ---------GGGARRGRGR--------------PADFSRGQSGGRYDG------DYATR
XP001110514      ----DRRDNRLRGPGGPRGGLGGMRGPPRGGMVQKPGFGVGRGLAPRQ
EAW61662         ----DRRDNRLRGPGGPRGGLGGMRGPPRGGMVQKPGFGVGRGLAPRQ
```

FIGURE 2 (continued)

| | |
|---|---|
| EAZ27342 | RGRGPPPGNGYQN------------------------------------------------- |
| EAY90482 | RGRGPPPGNGYQN------------------------------------------------- |
| GSBP-LIKE | RGRGPPPGNGYQN------------------------------------------------- |
| NP001060210 | RGRGPQGNGYHQNGNGGGYHQNGDGYHQNGDGYHQNGNRYNQNGNRYHQNGDEYYQNGNG |
| EAZ04627 | RGRGPQGNGYHQNGNGGGYHQNGDGYHQNGDGYHQNGNRYNQNGNRYHQNGDEYYQNGNG |
| NP001052571 | SSRGGDVG-YQRVD------------------------------------------------ |
| EAY93771 | SSRGGDVG-YQRVD------------------------------------------------ |
| NP200906 | NPRNGGEG-YQRVP------------------------------------------------ |
| NP189151 | NRANGDGGFPRAN------------------------------------------------- |
| BAE71222 | RPRGGNNTGRSNGD------------------------------------------------ |
| Q1SBN7 | RSRGGQNAGRSNGD------------------------------------------------ |
| NP178462 | QNNGHGNTEAKN--------------------------------------------------- |
| BAE71299 | SGRGDGYLQRGSR-------------------------------------------------- |
| CAE03370 | S-KGNGYQRRV---------------------------------------------------- |
| XP001110514 | --------------------------------------------------------------- |
| EAW61662 | --------------------------------------------------------------- |

| | |
|---|---|
| EAZ27342 | -----------------NGFHPARPFQNGNG--RFTRVNGPRQTPVAA-- |
| EAY90482 | -----------------NGFHPARPFQNGNG--RFTRVNGPRQTPVAA-- |
| GSBP-LIKE | -----------------NGFHPARPFQNGNG--RFTRVNGPRQTPVAA-- |
| NP001060210 | NGHRQNGSGYYHQNGNGYRQDRIFHNGNGNGRPARFNGPRQTPVQA-- |
| EAZ04627 | NGHRQNGSGYYHQNGNGYRQDRIFHNGNGNGRPARFNGPRQTPVQA-- |
| NP001052571 | -----------------HSAG--RAARAPSGTSAVAK------------ |
| EAY93771 | -----------------HSAG--RAARAPSGTSAVAK------------ |
| NP200906 | -----------------QNGGGGRGGRGEGGRGGARGGGSS-------- |
| NP189151 | -----------------GNNGRVRGGNDANRATKPVDDAPRVSVAA |
| BAE71222 | -----------------AAPRSYQNGGKVARQPPVKAQ----------- |
| Q1SBN7 | -----------------AVPRSYQNGGGKVAARQPPVKVQ---------- |
| NP178462 | --------------------------------------------------- |
| BAE71299 | --------------------------------------------------- |
| CAE03370 | --------------------------------------------------- |
| XP001110514 | --------------------------------------------------- |
| EAW61662 | --------------------------------------------------- |

FIGURE 2 (continued)

SEQ ID NO: 1; GSBP-like coding encoding sequence, Oryza sativa
GTACAAAAAAGCAGGCTTAAACAATGGCAGTGCAAGCTGGAACCCCAGCTACTCCTATAAGCCCCC
AAGTGATTAGTGGTGCATTTGTTCAGCAATATTACCACATTCTACATGAGACACCAGATCAGGTCT
ATAAGTTCTATCAAGATGCAAGTATTGTTGGTCGGCCTGATTCTAATGGAGTCATGAAATATGTAT
CAACAACTGCTGATATCAACAAAACAATCTTGTCTATGGACTTCAGCAACTACTTAACAGAGATAG
AGACTGCAGATGCACAGTTATCTCACCAGGATGGTGTGCTCATTGTTGTTACTGGATCTTTGACAT
CTGAAGGCATATGCCGTAGATTTACACAGTCATTCTTCCTTGCACCACAAGAATCTGGTGGCTATG
TTGTTCTCAATGATATTTTTAGATTTATAGTGGAAAGGCCACCAGTTGCAATAAGTCAAGTTAGTC
AAGAAAATGAGAACAATCAGAACACTGCCACTCTTCCTGAAACTGATCCTAATCCAGCGGGAGATG
GTATGATCTCAGAGCCTGTGGCAGTGGAAAATAATGTTGCGGAGGGGGAAGTGACAAATTCCACGG
TTGATGGCACTAGTATTGAAAATAATGCTACTGCTGCTGTCGAACCACCTGTACAAATGACGAAAG
AGGAGCCCAGGAAGATCTCTGTTGCTGCTCCTCCCCCTCCAGCTCAGAAGGATGTAACGAAGAAGT
CCTATGCGTCGATTGTGAAGGTTATGAAGGAGGTGTCACTAACCCCAGTTGTCAAACCTAAGCCAG
CTCCAAAACATGTGGTTAAGACTGTTGAAGCTTCAGAGAAACCTTCTGTTAAAAGTTCTCAAACTG
TTGAAATCACTCCGAATGATAACAACGATGCTGAAAATAACACTTCTAATGATGAGCAAGGTTACT
CAGTTTTTGTGAAGAGTTTGCCTCACAATGTGACAGTCCAGACGGTTGAGGAAGAGTTCAAGAAAT
TTGGCGCTATCAAGCCAGGTGGCATCCAAGTTAGGAACAACAAGATTGACCGGTTCTGCTTTGGTT
TTATTGAGTTTGAGTCCCAGCAATCTATGCAGGCAGCAATTGAGGCATCTCCGATTCATATGGGTG
GGAAAGAAGTATTTGTTGAGGAGAAAAGAACCACTACCCGAGTTGTGAATGGTGTTGTCATCACGC
GTGGTGATAATGGGAATGCTGGTGGAGGCGGACGTTACCAATCTGGAAGGGGAGGCTACCGCGGTG
ATAATTTCAGGGGACGGGGTGGTGGCTATGCGAACAGCGGAAACTACCGTGGAGGTGATAACTTCA
GCAGGAGGAACGACTTGAGAAATCGCAACGAGTTTTCAGGTCGTGGTCGAGGGCCACCGCCTGGGA
ATGGCTATCAGAACAACGGATTCCATCCAGCAAGGCCGTTCCAGAACGGAAATGGGAGGTTCACCC
GAGTCAACGGCCCTAGGCAAACACCGGTTGCGGCATAGAGGAGGGCAATGATGACCCAGCTTT

SEQ ID NO: 2; GSBP-like, Oryza sativa
MAVQAGTPATPISPQVISGAFVQQYYHILHETPDQVYKFYQDASIVGRPDSNGVMKYVSTTADINK
TILSMDFSNYLTEIETADAQLSHQDGVLIVVTGSLTSEGICRRFTQSFFLAPQESGGYVVLNDIFR
FIVERPPVAISQVSQENENNQNTATLPETDPNPAGDGMISEPVAVENNVAEGEVTNSTVDGTSIEN
NATAAVEPPVQMTKEEPRKISVAAPPPPAQKDVTKKSYASIVKVMKEVSLTPVVKPKPAPKHVVKT
VEASEKPSVKSSQTVEITPNDNNDAENNTSNDEQGYSVFVKSLPHNVTVQTVEEEFKKFGAIKPGG
IQVRNNKIDRFCFGFIEFESQQSMQAAIEASPIHMGGKEVFVEEKRTTTRVVNGVVITRGDNGNAG
GGGRYQSGRGGYRGDNFRGRGGGYANSGNYRGGDNFSRRNDLRNRNEFSGRGRGPPPGNGYQNNGF
HPARPFQNGNGRFTRVNGPRQTPVAA

SEQ ID NO: 3; GOS2 promoter (rice)
AATCCGAAAAGTTTCTGCACCGTTTTCACCCCCTAACTAACAATATAGGGAACGTGTGCTAAATAT
AAAATGAGACCTTATATATGTAGCGCTGATAACTAGAACTATGCAAGAAAAACTCATCCACCTACT
TTAGTGGCAATCGGGCTAAATAAAAAGAGTCGCTACACTAGTTTCGTTTTCCTTAGTAATTAAGT
GGGAAAATGAAATCATTATTGCTTAGAATATACGTTCACATCTCTGTCATGAAGTTAAATTATTCG
AGGTAGCCATAATTGTCATCAAACTCTTCTTGAATAAAAAAATCTTTCTAGCTGAACTCAATGGGT
AAAGAGAGAGATTTTTTTAAAAAAATAGAATGAAGATATTCTGAACGTATTGGCAAAGATTTAAA
CATATAATTATAATTTTATAGTTTGTGCATTCGTCATATCGCACATCATTAAGGACATGTCTTA
CTCCATCCCAATTTTTATTTAGTAATTAAAGACAATTGACTTATTTTTATTATTTATCTTTTTCG
ATTAGATGCAAGGTACTTACGCACACACTTTGTGCTCATGTGCATGTGTGAGTGCACCTCCTCAAT
ACACGTTCAACTAGCAACACATCTCTAATATCACTCGCCTATTTAATACATTTAGGTAGCAATATC
TGAATTCAAGCACTCCACCATCACCAGACCACTTTTAATAATATCTAAAATACAAAAAATAATTTT
ACAGAATAGCATGAAAAGTATGAAACGAACTATTTAGGTTTTTCACATACAAAAAAAAAAAGAATT

FIGURE 5

```
TTGCTCGTGCGCGAGCGCCAATCTCCCATATTGGGCACACAGGCAACAACAGAGTGGCTGCCCACA
GAACAACCCACAAAAAACGATGATCTAACGGAGGACAGCAAGTCCGCAACAACCTTTTAACAGCAG
GCTTTGCGGCCAGGAGAGAGGAGGAGAGGCAAAGAAAACCAAGCATCCTCCTTCTCCCATCTATAA
ATTCCTCCCCCCTTTTCCCCTCTCTATATAGGAGGCATCCAAGCCAAGAAGAGGGAGAGCACCAAG
GACACGCGACTAGCAGAAGCCGAGCGACCGCCTTCTCGATCCATATCTTCCGGTCGAGTTCTTGGT
CGATCTCTTCCCTCCTCCACCTCCTCCTCACAGGGTATGTGCCTCCCTTCGGTTGTTCTTGGATTT
ATTGTTCTAGGTTGTGTAGTACGGGCGTTGATGTTAGGAAAGGGGATCTGTATCTGTGATGATTCC
TGTTCTTGGATTTGGGATAGAGGGGTTCTTGATGTTGCATGTTATCGGTCGGTTTGATTAGTAGT
ATGGTTTTCAATCGTCTGGAGAGCTCTATGGAAATGAAATGGTTTAGGGATCGGAATCTTGCGATT
TTGTGAGTACCTTTTGTTTGAGGTAAAATCAGAGCACCGGTGATTTGCTTGGTGTAATAAAGTAC
GGTTGTTTGGTCCTCGATTCTGGTAGTGATGCTTCTCGATTTGACGAAGCTATCCTTTGTTTATTC
CCTATTGAACAAAATAATCCAACTTTGAAGACGGTCCCGTTGATGAGATTGAATGATTGATTCTT
AAGCCTGTCCAAAATTTCGCAGCTGGCTTGTTTAGATACAGTAGTCCCCATCACGAAATTCATGGA
AACAGTTATAATCCTCAGGAACAGGGATTCCCTGTTCTTCCGATTTGCTTTAGTCCCAGAATTTT
TTTTCCCAAATATCTTAAAAAGTCACTTTCTGGTTCAGTTCAATGAATTGATTGCTACAAATAATG
CTTTTATAGCGTTATCCTAGCTGTAGTTCAGTTAATAGGTAATACCCCTATAGTTTAGTCAGGAGA
AGAACTTATCCGATTTCTGATCTCCATTTTTAATTATATGAAATGAACTGTAGCATAAGCAGTATT
CATTTGGATTATTTTTTTTATTAGCTCTCACCCCTTCATTATTCTGAGCTGAAAGTCTGGCATGAA
CTGTCCTCAATTTTGTTTTCAAATTCACATCGATTATCTATGCATTATCCTCTTGTATCTACCTGT
AGAAGTTTCTTTTTGGTTATTCCTTGACTGCTTGATTACAGAAAGAAATTTATGAAGCTGTAATCG
GGATAGTTATACTGCTTGTTCTTATGATTCATTTCCTTTGTGCAGTTCTTGGTGTAGCTTGCCACT
TTCACCAGCAAAGTTC
```

SEQ ID NO: 4; RCc3 promoter (rice)
```
TCGACGCTACTCAAGTGGTGGGAGGCCACCGCATGTTCCAACGAAGCGCCAAAGAAAGCCTTGCAG
ACTCTAATGCTATTAGTCGCCTAGGATATTTGGAATGAAAGGAACCGCAGAGTTTTTCAGCACCAA
GAGCTTCCGGTGGCTAGTCTGATAGCCAAAATTAAGGAGGATGCCAAAACATGGGTCTTGGCGGGC
GCGAAACACCTTGATAGGTGGCTTACCTTTTAACATGTTCGGGCCAAAGGCCTTGAGACGGTAAAG
TTTTCTATTTGCGCTTGCGCATGTACAATTTTATTCCTCTATTCAATGAAATTGGTGGCTCACTGG
TTCATTAAAAAAAAAGAATCTAGCCTGTTCGGGAAGAAGAGGATTTTGTTCGTGAGAGAGAGAGA
GAGAGAGAGAGAGAGAGAGAGAAGGAGGAGGAGGATTTTCAGGCTTCGCATTGCCCAACCTC
TGCTTCTGTTGGCCCAAGAAGAATCCCAGGCGCCCATGGGCTGGCAGTTTACCACGGACCTACCTA
GCCTACCTTAGCTATCTAAGCGGGCCGACCTAGTAGCCACGTGCCTAGTGTAGATTAAAGTTGCCG
GGCCAGCAGGAAGCCACGCTGCAATGGCATCTTCCCCTGTCCTTCGCGTACGTGAAAACAAACCCA
GGTAAGCTTAGAATCTTCTTGCCCGTTGGACTGGGACACCCACCAATCCCACCATGCCCCGATATT
CCTCCGGTCTCGGTTCATGTGATGTCCTCTCTTGTGTGATCACGGAGCAAGCATTCTTAAACGGCA
AAAGAAAATCACCAACTTGCTCACGCAGTCACGCTGCACCGCGCGAAGCGACGCCCGATAGGCCAA
GATCGCGAGATAAAATAACAACCAATGATCATAAGGAAACAAGCCCGCGATGTGTCGTGTGCAGCA
ATCTTGGTCATTTGCGGGATCGAGTGCTTCACAGCTAACCAAATATTCGGCCGATGATTTAACACA
TTATCAGCGTAGATGTACGTACGATTTGTTAATTAATCTACGAGCCTTGCTAGGGCAGGTGTTCTG
CCAGCCAATCCAGATCGCCCTCGTATGCACGCTCACATGATGGCAGGGCAGGGTTCACATGAGCTC
TAACGGTCGATTAATTAATCCCGGGGCTCGACTATAAATACCTCCCTAATCCCATGATCAAAACCA
TCTCAAGCAGCCTAATCATCTCCAGCTGATCAAGAGCTCTTAATTAGCTAGCTAGTGATTAGCTGC
GCTTGTGATC
```

SEQ ID NO: 5; forward primer prm8784
```
GGGGACAAGTTTGTACAAAAAAGCAGGCTTAAACAATGGCAGTGCAAGCTGGAA
```

FIGURE 5 (continued)

SEQ ID NO: 6; reverse primer prm8783
GGGGACCACTTTGTACAAGAAAGCTGGGTCATCATTGCCCTCCTCTATGC SEQ ID NO: 7; EAZ27342.1 hypothetical protein OsJ_010825 [Oryza sativa (japonica cultivar-group)], variant of SEQ ID NO: 2
MAVQAGTPATPISPQVISGAFVQQYYHILHETPDQVYKFYQDASIVGRPDSNGVMKYVSTTADINK
IILSMDFSNYLTEIETADAQLSHQDGVLIVVTGSLTSEGICRRFTQSFFLAPQESGGYVVLNDIFR
FIVERPPVAISQVSQENENNQNTATLPETDPNPAGDGMISEPVAVENNVAEGEVTNSTVDGTSIEN
NATAAVEPPVQMTKEEPRKISVAAPPPPAQKDVTKKSYASITLTMIALQVKVMKEVSLTPVVKPKP
APKHVVKTVEASEKPSVKSSQTVEITPNDNNDAENNTSNDEQGYSVFVKSLPHNVTVQTVEEEFKK
FGAIKPGGIQVRNNKIDRFCFGFIEFESQQSMQAAIEASPIHMGGKEVFVEEKRTTTRVVNGVVIT
RGDNGNAGGGGRYQSGRGGYRGDNFRGRGGGYANSGNYRGGDNFSRRNDLRNRNEFSGRGRGPPPG
NGYQNNGFHPARPFQNGNGRFTRVNGPRQTPVAA SEQ ID NO: 8; EAY90482.1, hypothetical protein OsI_011715 [Oryza sativa (indica cultivar-group)] (variant of SEQ ID NO: 2)
MPSRMMQAFAQEASDFDRQMGCMAGMFQIFDRRRLLTARQRGGARGTAPPGHVLPNSNSNVSIQNP
VASNNTLVYDDDARDGAIGFPMAVQAGTPATPISPQVISGAFVQQYYHILHETPDQVYKFYQDASI
VGRPDSNGVMKYVSTTADINKIILSMDFSNYLTEIETADAQLSHQDGVLIVVTGSLTSEGICRRFT
QSFFLAPQESGGYVVLNDIFRFIVERPPVAISQVSQENENNQNTATLPETDPNPAGDGMISEPVAV
ENNVAEGEVTNSTVDGTSIENNATAAVEPPVQMTKEEPRKISVAAPPPPAQKDVTKKSYASITLTM
IALQVKVMKEVSLTPVVKPKPAPKHVVKTVEASEKPSVKSSQTVEITPNDNNDAENNTSNDEQGYS
VFVKSLPHNVTVQTVEEEFKKFGAIKPGGIQVRNNKIDRFCFGFIEFESQQSMQAAIEASPIHMGG
KEVFVEEKRTTTRVVNGVVITRGDNGNAGGGGRYQSGRGGYRGDNFRGRGGGYANSGNYRGGDNFS
RRNDLRNRNEFSGRGRGPPPGNGYQNNGFHPARPFQNGNGRFTRVNGPRQTPVAA SEQ ID NO: 9; NM_001066745.1 Oryza sativa (japonica cultivar-group) Os07g0603100 (Os07g0603100) mRNA, complete cds;
CTCCTCTCTCCGTCTCGCTTCGGTTCCTTCCTCGAGTCGAAACCTCGCGAAGCCGCCGCCGCCGCC
GCCGACTCTCGCTAGGGCTAGGGTTTTCCTCCCGCCGCCGGGAGCCCCTCCCCCTGCAACCGCGCA
AGGGATGGCTATGCAAGTTGGGGAATCAGTTGCTCCTTTAAGTCCACAAATGATTGGAAATGCGTT
TGTTCAACAATACTACAATGTTCTCCATAGTTCACCGGGTCAAGTTTGTAAGTTCTATCATGATTC
AAGCACCCTTGGTCGACCAGATTCTAATGGAACCATGACATCTGTAACCACATTGACTGCTATCAA
CGATGAATTTCTCTCTACGGACTTCAGTAGCTGTTTGATTAAGTTAGAGAATGTGGATGCACAGTT
ATCCCTCAATGGTGGTGTGCACATTTTGGTAACTGGATCTATTGGACACAATGGCACTATGAGGCA
TAGATTTAGCCAGTCATTCTTCCTTGCTCCACAAGAAAGCGGAGGCTATTTTGTTCTGAATGATAT
GCTAAGATATGATTCTCTGCAAGAAACACTGTTGACTGAGACAAATGATTCTCCACAAGAAAGACT
GTTGACTGAGATAAATGATTCTCTGCCTAACCATGTTGATGATAACACTCACAGTGTCACATTTAC
ATCTGAGCCAGAGACTTCAGGCAATGTCAATGAGACTGCAGACTTGGAGCTTCCATCTGCAGAGAA
TGTCAATGACAATGTTGAGAATCTGCCTGCCAATGACAGTTCTCCCGAAGAAATGTTCTTGTTGA
GGCATGCACGGAAGTGGTTAGTTCGTGTGCAGAGAACATTCCTGCAGCTGCACCTGCACCTGCTCC
TCGTGCCTCGACTCAGAAGGATGTTACTAAACAGTCATATGCATCAGTTGTTAAGGTTACAAAGGA
GGGCACACCAACTCCACCTGTTGCAAAGCCCAAGCCCAAACCCAAACCAAAGCCAACTGCAAAAGT
GACTGACAATGTGGAGAAAGCTGTGTCCTCACCTGTGAAACCTACTAATGCAGCTGATACCACATC
TCCAAATGACAAAAATGTTCTTGTTGAGCAAGGGTATTCTGTTTATGTAAAGCACTTACCTTATGA
ATGTACCACGAAAGATGTTGAGGAAAAGTTCAGGAAATTTGGTGCTATCAGGCCTGGTGGTATTCA
AGTTCGACACCGTCAGCCCGATGGATTCTGCTTTGGCTTTGTTGAATTTGAGTCTCGGCAATCCAT
GCTAGCAGCAATTGAGGCCTCTCCAGTTTCTATTGGCTCAAAAGCATCCATTGTTGAGGAGAAACG FIGURE 5 (continued)

AACTACAACTCGAGTTGTTAATGGTGTCACCCATATTGAAAACAATGGCAATGCTCGGGGTGGTCG
GTTCCAGCAAGACAACAGAGGTGGTGGATACCGTGGGGACAACTTCAGGGGACGAGAAGCAGGTTT
CGTGAACAATGGTAACTACCGTGATGGTGATAACATGAGGAACGGATTCAGAAATCAGAACGAGTA
CTCAGGGCGTGGTCGTGGGCCTCAGGGGAATGGTTACCATCAGAATGGTAACGGTGGTGGTTACCA
TCAGAATGGAAATGGATACCATCAGAACGGTGATGGATACCATCAGAATGGGAACAGATACAATCA
GAACGGGAACAGATACCATCAGAACGGAGATGAGTACTATCAGAACGGCAATGGCAATGGACATCG
GCAGAATGGGTCTGGATACTATCATCAGAATGGGAATGGCTATCGTCAGGACCGCATCTTCCACAA
TGGGAATGGAAATGGGCGGCCTGCTCGCTTCAATGGACCCAGGCAAACACCGGTTCAAGCGTAGGC
GTTTCTTGAATATCCAAAAAATCCTTTTGTCAATCCTAGGATCGCCTTATTTATCTGTGTTCTTTT
GCACCCCATTCGGCTGCGACAAAGTTCAGTCCCAGCCCTTCGTTTTGCCTCGATGCTTTTGCTGAC
TAGTTGGCATGTTCTGGATGTACTTGGTGAGACCAGGAAGTGTAATTTTGGAAAGGTTGGGAGCTT
ACTGCAAGGTTCGTGACTTCATGTCGAGACATGCTATCTAATATATGCATTAGTATTTATGGCACG
CAGATGGATGAAGGATCTGTTGTGTGCTTTTCCTTATG

SEQ ID NO: 10; NP_001060210.1| Os07g0603100 [Oryza sativa (japonica cultivar-group)]
MAMQVGESVAPLSPQMIGNAFVQQYYNVLHSSPGQVCKFYHDSSTLGRPDSNGTMTSVTTLTAIND
EFLSTDFSSCLIKLENVDAQLSLNGGVHILVTGSIGHNGTMRHRFSQSFFLAPQESGGYFVLNDML
RYDSLQETLLTETNDSPQERLLTEINDSLPNHVDDNTHSVTFTSEPETSGNVNETADLELPSAENV
NDNVENLPANDSSPEENVLVEACTEVVSSCAENIPAAAPAPAPRASTQKDVTKQSYASVVKVTKEG
TPTPPVAKPKPKPKPKPTAKVTDNVEKAVSSPVKPTNAADTTSPNDKNVLVEQGYSVYVKHLPYEC
TTKDVEEKFRKFGAIRPGGIQVRHRQPDGFCFGFVEFESRQSMLAAIEASPVSIGSKASIVEEKRT
TTRVVNGVTHIENNGNARGGRFQQDNRGGGYRGDNFRGREAGFVNNGNYRDGDNMRNGFRNQNEYS
GRGRGPQGNGYHQNGNGGGYHQNGNGYHQNGDGYHQNGNRYNQNGNRYHQNGDEYYQNGNGNGHRQ
NGSGYYHQNGNGYRQDRIFHNGNGNGRPARFNGPRQTPVQA

SEQ ID NO: 11; A2YNG6_ORYSI; EAZ04627; Hypothetical protein, Oryza sativa (variant from SEQ ID NO: 10)
MAMQVGESVAPLSPQTIGNAFVQQYYNVLHSSPGQVCKFYHDSSTLGRPDSNGTMTSVTTLTAIND
EFLSTDFSSCLIKLENVDAQLSLNGGVHILVTGSIGHNGTMRHRFSQSFFLAPQESGGYFVLNDML
RYDSLQETLLTETNDSPQERLLTEINDSLPNHVDDNTHSVTFTSEPETSGNVNETADLELPSAENV
NDNVENLPANDSSPEENVLVEACTEVVSSCAENIPAAAPAPAPRASTQKDVTKQSYASVVKVTKEG
TPTPPVAKPKPKPKPKPTAKVTDNVEKAVSSPVKPTNAADTTSPNDKNVLVEQGYSVYVKHLPYEC
TAKDVEEKFRKFGAIRPGGIQVRHRQPDGFCFGFVEFESRQSMLAAIEASPVSIGSKASIVEEKRT
TTRVVNGVTHIENNGNAWGGRFQQDNRGGGYRGDNFRGREAGFVNNGNYRDGDNLRNRFRNQNEYS
GRGRGPQGNGYHQNGNGGGYHQNGNGYHQNGDGYHQNGNRYNQNGNRYHQNGDEYYQNGNGNGHRQ
NGSGYYHQNGNGYRQDRIFHNGNGNGRPARFNGPRQTPVQA

SEQ ID NO: 12; NM_126414.3 Arabidopsis thaliana nuclear transport factor 2 (NTF2) family protein / RNA recognition motif (RRM)-containing protein (AT2G03640) mRNA, complete cds
CACCTTCCTTCTCTCCTTCACTCTAATTGCGATTGATTCTCCTGTCTTCTCCAATTTATCAGAGAA
ATTGCAGAGATGACACCTGAATCAAACGCTCCCTCAGTAGATCCACAATTTGTAGGCAATGGGTTT
GTTCAAGAATACTATAACCACCTTTATGATTCAACCTCGGAAGTACACAAATTCTATCTCGAGGAT
AGTATGATTTCACGGCCTGGTCTCGATGGTGAGATAGTTACTATCAAATCCTTGAAAGGGATTAAT
GATCAGATAATGTCCATTGACTACAAAAGCTCAAGGATCGAGATTCTAACTGCTGATTCTCAATCA
ACTTTAAAGAATGGTGTTGTAACTCTAGTCACGGGTTTAGTGATCGGGAACGATGGAGGAAGGAGG
AAATTTTCTCAGAGTTTCTTTCTTGTGTCGCGGAATGGAAGCTACTTTGTGCTGAATGATACCTTT FIGURE 5 (continued)

```
AGGTATGTGTCTGATGAGTTTGTTGAACCAGAAGCTACCAAGGAGGTTGAGGAGAGTCAGTCAACA
AATGCTATCACTGAGCCTGCAAATGAAAGTGTAGAGGCGGTTATTGTCCCTACTGAAGCTAAAACT
ACGGTGACGAAGCCAGCAAGTGCCATACCAAACGGACATGCGAAAGTCCCTGAGGAGAAAGTTGTG
AATGAAAACAGTAGCTTACCTAAAGCTGCTGAAGCAAAACTTCAAGAGGAGGTTCCCAAGAAATCG
TTTGCATTAATTGTTCAATCTCTGGCTCAAAGCGCTGGTACTTTACAGGTTAAAGCCTCGCCGGTC
AAGCGTAAACCTGTCGAAAAACCGGTTGCTGCTCCGGAGCGCAAAGCTCCTTCCCCAATTCGTAAA
CAGGCTTCTGCTGAAAGCATTAAACCACAAGCTCAGGGTAGTTCCATATTTGTTGCAAACTTGCCT
ATGGATGCGACTATTGAGCAACTTTATGAAACATTTAAAAGTTTTGGAGCTATTAGAAAGGATGGT
ATCCAAGTCAGAAGTTACCCGGAAAAAAAGAACTGTATTGGGTTTGTGGCATTCGAAAATGGTGAA
GCAGTAAAAAATGTCTTTCAGGCTCACAGGGAATCACCAATCAGAATCGGAAACCGAAGAGCATCT
ATAGAAGAAAAGCGAGGAGGTAACAATCAAATGGCAACAGAGTCTCTACAAGAAACAACAGTGGT
TATAAAAATGAGGATGGTTTCAGACGTGATGGATACAAACCTAGGGGCAGTGGCGTCAATGGAGGA
CGAGGCTATGGGAGACGGAACAGTGAGTCTAATGGGGATGGTAAAGCATACCAGAACAATGGCCAT
GGCAATACTGAGGCCAAAAACTAGATTAGTTTTTTCTTCTTCTAAGCTTTGCTCATGGTTGAGAAT
CTGAGGTTGTAGGCGATGTTAAAACAAATTTTTGTTTCCGTGGATATCTTAGGTGTTGATCTTTTC
GATTTGTGATATTGTTTGGGGATAAATCTAGAACATTTTTCTTCACTCTTTGATCTCTGTATCTTC
TCATGAACAAAGCAGAGAACAAAATCGAATTGATTTAAGGTTCT
```

SEQ ID NO: 13; NP_178462, Arabidopsis thaliana nuclear transport factor 2 (NTF2) family protein / RNA recognition motif (RRM)-containing protein

```
MTPESNAPSVDPQFVGNGFVQEYYNHLYDSTSEVHKFYLEDSMISRPGLDGEIVTIKSLKGINDQI
MSIDYKSSRIEILTADSQSTLKNGVVTLVTGLVIGNDGGRRKFSQSFFLVSRNGSYFVLNDTFRYV
SDEFVEPEATKEVEESQSTNAITEPANESVEAVIVPTEAKTTVTKPASAIPNGHAKVPEEKVVNEN
SSLPKAAEAKLQEEVPKKSFALIVQSLAQSAGTLQVKASPVKRKPVEKPVAAPERKAPSPIRKQAS
AESIKPQAQGSSIFVANLPMDATIEQLYETFKSFGAIRKDGIQVRSYPEKKNCIGFVAFENGEAVK
NVFQAHRESPIRIGNRRASIEEKRGGNNQNGNRVSTRNNSGYKNEDGFRRDGYKPRGSGVNGGRGY
GRRNSESNGDGKAYQNNGHGNTEAKN
```

SEQ ID NO: 14; AT3G25150.1, nuclear transport factor 2 (NTF2) family protein / RNA recognition motif (RRM)-containing protein [Arabidopsis thaliana] encoding sequence

```
TTTTTTCTTCTTCTTCCATTTTTTTGTTCTCACGTCGCTCTCTCTTTTTTTCGAGATTCAGCTGT
AAAACCCTAACTAGCGCCATAGCCAAGGAAGCTTTCCTCAGATCGTCTCTCCGAAATTTTCCGGTT
AATCGTCAGTTAAGGGGAAAATTAGGCTATGGCGATGTTAGGTGCACAGCAAGTTCCAGCAGCAGC
TTGTACTCCAGATATGGTTGGGAATGCTTTTGTGCCCCAGTATTATCACATATTGCATCAATCACC
TGAGCATGTTCACAGATTTTACCAAGAGATTAGCAAGTTAGGTCGTCCTGAAGAGAATGGTTTAAT
GAGCATCACTTCTACCTTGCAAGCTATTGACAAGAAGATAATGGCGCTTGGTTACGGTGTAATCAG
TGCAGAGATAGCTACTGTGGACACACAAGAATCTCATGGAGGTGGTTATATTGTACTGGTGACTGG
GTATTTGACGGGAAAAGACAGTGTCAGGAGGACGTTTAGTCAGACCTTCTTCCTTGCTCCACAGGA
GACAGGATACTTTGTCTTGAATGATATGTTTCGATTCATTGATGAAGGCACTGTCGTACATGGAAA
TCAGATTCCAGTGAACAACGTCCAAGCTCCTGTCAACACTTACCAGGACACAGCTGCTGCGAAGGA
AATTCCAGATGACTTTGTTCAGGAGAAATATGTCCAAGAGAATCATGCTGTTAAGCAAACCGAGGT
GTTGTCCAAGAGCATTAATGAGCCTGAAAAAGTGTTCACGCCCTCTGAAGATGAACAAGTATCAGC
TGCAGAAGAAGCTCTGGTGACTGAAACAGTTAATGAAGCACCAATTGAAGTGCAAAAGGTTGGAGA
ATCTGATTCTAGGACTGGCGAAATTCCAAAGAGATCTTATGCATCAATTGTGAAGGTTATGAAAGA
AAATGCTGCACCAATGTCTGCTTCGAGAACTCCAACAAAGGTGGAACCAAAGAAACAAGAAGATCA
AGCCATTCATATCCCTCTACCAACACCATTGTCTGAGAAATCAGATTCAGGAGCAAATGTTGCTGT
```

FIGURE 5 (continued)

AAATGAGAACAATCAAGAGAATGAAAGAGCTCTAGGTCCATCCATCTATCTAAAGGGTTTACCCCT
TGATGCAACACCTGCCTTGCTTGAGAATGAGTTCCAGAAATTTGGACTTATTAGGACCAATGGAAT
TCAAGTGAGAAGCCAGAAGGGATTCTGTTTTGGTTTTGTTGAGTTTGAATCCGCAAGTTCCATGCA
AAGCGCTATCGAGGCATCACCTGTCATGCTCAATGGACACAAAGTTGTTGTGGAGGAAAAGCGATC
TACCGCAAGAGGGAACTATAGAGGACGTTCGACGTTTGGTGTAAACACAGGCTACAGAAACGAAGG
AGGAAGGGGTCGTGGGAGCTTTGGAGGTGGAAGAGGAGGATATGGCCGGACCGATTTCAACGGATA
TGGTAATAACAGGGGAAACAATAGAGGCGGATACGCAAACCGAGCAAATGGTGATGGTGGTGGGTT
CCCGAGGGCCAATGGTAACAATGGACGAGTAAGACGTGGTGGCGGAAATGATGCTAACAGAGCTAC
GAAACCCGTGGATGATGCTCCCCGTGTGTCTGTTGCTGCGTAAATGTGCTTTTGAAACAAAAAGCT
CTATTGGTTTTAGAGAGTTTAGGCGTAGAGCAATGGCAAAAAAAAACACTATTATTTTCTTTTCAC
TGTGTCGCCATTTTATTAATTGGAGTCAAAACTTGAGAGCAAGAGAGAGTTTCGTCGGTTCTTGCT
TGTCTATTTTTTCTTCACTGCTAATGAAATCTCTTTCTTCATGTGGCTC

SEQ ID NO: 15; NP_189151.2; nuclear transport factor 2 (NTF2) family protein / RNA recognition motif (RRM)-containing protein [Arabidopsis thaliana]
MAMLGAQQVPAAACTPDMVGNAFVPQYYHILHQSPEHVHRFYQEISKLGRPEENGLMSITSTLQAI
DKKIMALGYGVISAEIATVDTQESHGGGYIVLVTGYLTGKDSVRRTFSQTFFLAPQETGYFVLNDM
FRFIDEGTVVHGNQIPVNNVQAPVNTYQDTAAAKEIPDDFVQEKYVQENHAVKQTEVLSKSINEPE
KVFTPSEDEQVSAAEEALVTETVNEAPIEVQKVGESDSRTGEIPKRSYASIVKVMKENAAPMSASR
TPTKVEPKKQEDQAIHIPLPTPLSEKSDSGANVAVNENNQENERALGPSIYLKGLPLDATPALLEN
EFQKFGLIRTNGIQVRSQKGFCFGFVEFESASSMQSAIEASPVMLNGHKVVVEEKRSTARGNYRGR
STFGVNTGYRNEGGRGRGSFGGGRGGYGRTDFNGYGNNRGNNRGGYANRANGDGGGFPRANGNNGR
VRRGGGNDANRATKPVDDAPRVSVAA

SEQ ID NO: 16; NM_001059106.1; Oryza sativa (japonica cultivar-group) Os04g0372800 mRNA, complete cds
GAGCGAGAGAGGAGACAAACCCCTCTCCACCTCCCCCCAAAACCCTAACCCTTCCTCCTCCCACCT
TCCCGCCACGCCACCATGGCCTCGCCCCGCCGCCGCCGCCCTCCGCCGCCGCCCCGGATCGCCG
CCGTCGGCGCAAGTGGTGGGGAACGCGTTCGTGCACCAGTACTACAACATCCTGCACCAGTCGCCG
GATCTCGTCCACCGCTTCTACCAGGACGGGAGCCGCATCGGCCGCCCCGCCTCCCCGCCGCCGCC
GAGATGGACACCGTCACCACCATGGAGGCGATTAACGCGAAGATCGTGTCCATGGACATCGTGCGG
GCGGAGATCAAGGCGGTGGACGCGCAGGAGTCGCTGGGCGGGGCGTCACGGTGCTCGTCACGGGC
CACCTCACCGGGAGCGACGACGTGCGCAGGGAGTTCTCGCAGTCCTTCTTCCTCGCCGCAGGAG
AAGGGATACTTCGTGCTCAACGACATCCTGCGCTACGTCGGGGGGGAGGGGGATCAGGAGGTGGAG
CCGGAGCCGGAGCTGGAGCTGTCGTTTCCGCCGTCGCAGCAGCCGGATTCGGTGCCTGCTCCTTCG
GCGAATGGCACTAGCGTGCCGCGGGAACAGGAGGCCTTCTCGCAGCCGGAGCAGCATGTGGCTGAT
CCTGCACCCAATGCTCAGGAGGCTGATCTCAACGGCGAGGAGGTTTATAACCCACCGAACAACACA
GAGGGGCCTGTTGTGGAGGAAACGCCGATTCCTGAAGTTATAGATGAAGTGCCAAATAACGTAGCT
GTGGCTATGCCGACTCCGCCTGCCCCTGCCCCTGCCCCTGTACCACAAGAGGAGGCCCCCAAGAAG
TCGTATGCTTCAATTGTCAAAGTCATGAAAGAAATTCCACCACAAATATCTGCAATTCCTTCCAGG
CCGGCACCACCAAAACAAGAGAAGCAAGTTGCTCCTGCACCTGTTGCTCCGGTTGCTGATGCTCCA
ACTTTCAGTCCTAATCCTGAAAGCAGCAACATTCAAGAGGCTGAAGTTGATGCACATGCGATATAT
GTACGGAATCTGCCTTTAAGTGCCACGCCTGAACAATTAGAAGAAGCATTCAAGAAATTTGGCGCT
ATCAAGCCGGACGGAATCCAAGTTAGAAGTCACAAGATTCAAGGGTTCTGCTATGGGTTTGTAGAG
TTTGAAGATCCCAGTTCAGTTCAAAGTGCAATTGCGGGTTCTCCTGTGACGATTAGTGACCGGCAA
TGTTATGTGGAGGAAAAGAGAACTGCTGGTTCACGTGGTGGTGGCAGAGGAAGGTTTGCTCCTGGT
AGAGGTGGTAACTTCCGAGGTGAAGGCATGAGAGGCCGCGGGAATTACACCGGAGGGAGGGGCTAT

```
GGAAGGGGTGAGTTCAATTATCGATCCGACTATGGAGGCAGAGGCGCTGGTAGAGGTGGTTCATCA
CGTGGTGGTGATGTTGGCTACCAGCGGGTTGACCACTCTGCTGGTCGTGCTGCTCGGGCGCCATCG
GGCACTAGTGCCGTTGCAAAGTGAGCGAGTTAGTTGCTATGCCTCGGTTGCTATGCGTCGGTGAAA
AAGTTTGATATTTCGTGGGTTGGAATTATCAACATTCGGGAAGAGGGTATGTGTTGAGTTGGGTT
TATGTGAGAGATTATCAGCAAAAATCGGGTCATAAATTGAAGCTTCCCTTGTTTTGTGGCAAGGGA
GAGCAGTGGTGATATTGGTTTACTAATTGTAGCATATACGTCTATTCAGAATTTCAGATGTAGTCC
TGGTAAGCTTGGCCCTTTTTGGAGTACCTGATGTTTGTTTTTCCCCCTCTTTTTGTCCCTCTTTTC
TAGCAGGATCGATTCTATTACGAATGAGAGGTGATGAGTTATAGATTCC
```

SEQ ID NO: 17; NP_001052571.1; Os04g0372800 [Oryza sativa (japonica cultivar-group)]

```
MASPPPPPPSAAAPGSPPSAQVVGNAFVHQYYNILHQSPDLVHRFYQDGSRIGRPASPAAAEMDTV
TTMEAINAKIVSMDIVRAEIKAVDAQESLGGGVTVLVTGHLTGSDDVRREFSQSFFLAPQEKGYFV
LNDILRYVGGEGDQEVEPEPELELSFPPSQQPDSVPAPSANGTSVPREQEAFSQPEQHVADPAPNA
QEADLNGEEVYNPPNNTEGPVVEETPIPEVIDEVPNNVAVAMPTPPAPAPAPVPQEEAPKKSYASI
VKVMKEIPPQISAIPSRPAPPKQEKQVAPAPVAPVADAPTFSPNPESSNIQEAEVDAHAIYVRNLP
LSATPEQLEEAFKKFGAIKPDGIQVRSHKIQGFCYGFVEFEDPSSVQSAIAGSPVTISDRQCYVEE
KRTAGSRGGGRGRFAPGRGGNFRGEGMRGRGNYTGGRGYGRGEFNYRSDYGGRGAGRGGSSRGGDV
GYQRVDHSAGRAARAPSGTSAVAK
```

SEQ ID NO: 18; AB236770.1, Trifolium pratense RNA for putative ras-GTPase-activating protein SH3-domain binding protein, complete cds, clone: C1578

```
GGCACGAGGTTCTCTTTCTCTCTTTGATCTCTCCATCACACCAAGGAGAGATGGCAGTATCTGATG
GAGTCCAAACCCCAACCCCTCAGGTGGTTGGCAATGCTTTTGTCGAGCAGTATTACTCAATTCTTC
ACCAAGACCCGGATCAGGTTCATAAGTTTTACCACGAATCAAGTGTCTTGAGTCGACCTGAAGAAG
ACGGTACCATGACAACTGTCACTACCACTGCTGAAATTGATAAAAAGATACAATCTTTTGATTACA
CAAGCTATAGGGTAGAGGTTCTGAGTGCTGATGCTCAGCCTTCATATAATAGTGGGGTTGTGGTTG
TAGTGACTGGCTGCTTGACCGGAACTGACAATGTTAAACGCAAATTTGCTCAGTCCTTTTTCCTAG
CTCCACAGGACAAGGGCTTCTATGTTTTGAATGATGTTTTAGATATGTTGATGCGTATAAGTCTG
TTGATATTGAGACTGTACCAGCAAATGATGCTGATGAAAGTGCTCCATCAGAAGCTTTTACTCCAG
ATCCTGAGCCTATTCATGTTGCTGAAGACATTCCAACCATTCAACCTGTTATTGCTGATACTGACA
CTAACATCAGCAAAGAAGTGAGCTTACCACTGGAGAATGGAAAATTATCAGTTACTGAAAATGTGA
TTCCTGTTAATCATGTTAAAGAGTCAAGTCATCAGGAACAAATGGCAAGCATTGAGAAAGTTCCTT
CAAATACACAGGAGGATACTCCCAAAAAATCTTTTGCATCCATTGTGAGTGCCTATAAAGATAATT
CTGCTCCCTTCCTTTCGAGGACTTCTCCTGCAAAACCCGCTGTGCAACCACCCCGTGTACATAGCG
TGCCTGCTCCTGAAGCACCAGCCCCTAACATGGACATTCCATCGGAAAAGAATAATGAGAATGGAG
GTAGGGCTCATGCAATATTTGTTGCGAATTTGCCTATGACTGCAACAGTAGAGCAATTGGACCGGG
TTTTCAAGAAATTCGGGACCATTAAACGTGATGGTATTCAAGTTAGAAGTAACAAGGGATCTTGCT
TTGGTTTTGTGGAATTTGAATCTGCTGCTTCACTGCAAAGTGCCCTAGAGGCCTCCCCTCCTGTTA
TGTTGGACAACCGTAGGCTTTCCATTGAAGAAAGGCGAGGACGTGGTGGATACCGAAATGACAGAA
ATGATAACTTCAGGGGCCGTGGCAACTTTGGTGGCGGCCGTGGTGGTGGCTTTAACGGAAGGAATG
ATTTTGACAGGCGAGGCGAGTTCTCTGGCCGGCCTAGAGGAGGCAATAATACCGGTCGAAGCAATG
GAGATGCTGCGCCAAGGAGTTATCAGAATGGAGGAGGAAAAGTCGCTCGTCAACCGCCAGTGAAGG
CTCAGTAAAGTGCTTCTTTTGTCGGTAATTGAGTGGCAACGAGATTTTCTTAGTAGATAGAGGGA
GGCATTAGGGATTTTGGTTTGAATTTGAATTAGAGTCTTTTGCTTTGTAGTTTCTGTGATATTTTT
TCGTCAGAGTTCTTTGGTTAAATCAGGTTTTCTCCATACTGACTTCTTTTTTCTTAATCTCTTCCA
ATTTTGTTTCCTACTGTATCTAATTTTTCTGGTATGATTGTTTTGGAATTGGCCAGTTATATATCA
TTTTTGTTT
```

FIGURE 5 (continued)

SEQ ID NO: 19; BAE71222.1, putative ras-GTPase-activating protein
SH3-domain binding protein [Trifolium pratense]
MAVSDGVQTPTPQVVGNAFVEQYYSILHQDPDQVHKFYHESSVLSRPEEDGTMTTVTTTAEIDKKI
QSFDYTSYRVEVLSADAQPSYNSGVVVVVTGCLTGTDNVKRKFAQSFFLAPQDKGFYVLNDVFRYV
DAYKSVDIETVPANDADESAPSEAFTPDPEPIHVAEDIPTIQPVIADTDTNISKEVSLPLENGKLS
VTENVIPVNHVKESSHQEQMASIEKVPSNTQEDTPKKSFASIVSAYKDNSAPFLSRTSPAKPAVQP
PRVHSVPAPEAPAPNMDIPSEKNNENGGRAHAIFVANLPMTATVEQLDRVFKKFGTIKRDGIQVRS
NKGSCFGFVEFESAASLQSALEASPPVMLDNRRLSIEERRGRGGYRNDRNDNFRGRGNFGGGRGGG
FNGRNDFDRRGEFSGRPRGGNNTGRSNGDAAPRSYQNGGGKVARQPPVKAQ SEQ ID NO: 20; NM_125491.2; Arabidopsis thaliana nuclear transport
factor 2 (NTF2) family protein / RNA recognition motif (RRM)-
containing protein (AT5G60980) mRNA, complete cds
ACGGTTCCTTCTCTTCTCTCTCTCTCTTTCTCCGTCTGTCGCTGTCTCTCTCGTCCTCTCCTCTGT
TTCGTAGCTTCTGCAGCAGATCTCTCTTTGTCCTTCTCTCTCCCTCAGATCACTATGGCACAGCAG
GAAGCTAGTCCTTCCCCTGGTGCTGAGGTTGTTGGTCGTGCCTTTGTGGAGCAATACTATCATATT
CTTCACCAATCTCCCGGTTTAGTTCATCGGTTTTATCAAGATTCGAGCTTTTTAACCCGACCTGAT
GTTACCGGTGCTGTGACTACTGTCACAACTATGCAAGCGATCAACGACAAGATTCTGTCGTTGAAA
TATGAAGACTACACGGCTGAGATAGAAACTGCTGATGCTCAGGAGTCTCATGAGAGAGGTGTTATT
GTGCTGGTTACAGGACGCTTAACCGGGAACGATAATGTTAGGAAGAAGTTTAGTCAATCTTTTTTC
TTGGCTCCACAAGACAAAGGATACTTTGTCTTAAACGACGTGTTTCGATTCCTTGAGGAGAAAGAG
GTGACTGCACAAGCCCGCTCTGTCCCCATCAATGGAACCACTAGGGATGTTCAGGCTCCTATTGAA
CCAGAACGTGTTGTTGTTAGTCACGAGCCCGAGGTAGAACCCGAGCCAGTTGCTTCTATCGAGGAA
GAAGATCTTGACAATGTGGCGGAAGTGTATGATCCTTCTGATAAAGATGAAGGAGTTGTTGTTGAC
GTTGAGCCTATTGAACCTCCCACTCAAATAAGTCATAATGAAATCTTATCAGTGCCTCAAGGAGAT
GCTCCTAAGCATTCTTATGCTTCAATCCTCAAGCAGATGAAAAGCAGTCCAGCACCAACAACACAC
GTTGCTAGAAACAAGCCAAGACCAGCTCCAGTCAACCAGAAGCTGACCGCGCCTCCTGCTGAGCCT
GCAGCAAGACCCGAGGCTTCAGCTCATGAGAATGTTCCGAATAGTAGCCATGTTGATGTGGAAGAT
GATGGTCATTCGATTTATGTTCGAAATTTGCCGTTTGACTCCACACCAACACAACTTGAAGAGGTG
TTCAAGAACTTTGGTGCAATCAAGCATGAGGGGATTCAAGTCAGAAGCAACAAGCAGCAAGGTTTC
TGTTTTGGTTTTGTGGAATTTGAAACATCTAGCGGAAAGCAAAGTGCCCTCGAGGCCTCACCAGTT
ACAATTGGAGATCGTCAAGCTGTTGTAGAGGAGAAGAAAACAAATAGTCGAGGAGGAGGCAACAAT
GGAGGTAGCAGGGGAAGGTACTTTTCCGGAAGAGGAAGTTTCCGAAATGAAAGCTTCAAAGGAGGA
CGCGGTGGTGGGGAAGAGGAGGCTATGGAAGAGGAGGAGGTGAGTTTTCTGGTAGACCAAAGAGC
TCAAACCCACGAAATGGAGGAGAAGGTTACCAAAGGGTTCCTCAAAACGGAGGAGGTGGAAGAGGA
GGCCGCGGAGAAGGAGGTCGTGGTGGAGCTCGAGGTGGTGGTTCATCTTGACTTTGCTTTTAACGC
TCCTCTACAAGAGAGTAGTTTTAATTTTTGTTTTGCGTCTTTCTTTTTGCCTACTACTTGAGTTGA
TGTGGTATTGGCTTTTTTGTCGGTCTAGTTTTTCAATATTCTTGCTTTTTTTCCTCTCTTTTTTGT
TTTTCATCTTTCAATCTTTCTTTGGGGTAATGTACTCTTCATAAACAAACATTCAATTTCATAAGG
AATCCATTATAGAGTTGTGTTCTTTACGC SEQ ID NO: 21; NP_200906.2; nuclear transport factor 2 (NTF2)
family protein / RNA recognition motif (RRM)-containing protein
[Arabidopsis thaliana]
MAQQEASPSPGAEVVGRAFVEQYYHILHQSPGLVHRFYQDSSFLTRPDVTGAVTTVTTMQAINDKI
LSLKYEDYTAEIETADAQESHERGVIVLVTGRLTGNDNVRKKFSQSFFLAPQDKGYFVLNDVFRFL
EEKEVTAQARSVPINGTTRDVQAPIEPERVVVSHEPEVEPEPVASIEEEDLDNVAEVYDPSDKDEG
VVVDVEPIEPPTQISHNEILSVPQGDAPKHSYASILKQMKSSPAPTTHVARNKPRPAPVNQKLTAP FIGURE 5 (continued)

PAEPAARPEASAHENVPNSSHVDVEDDGHSIYVRNLPFDSTPTQLEEVFKNFGAIKHEGIQVRSNK
QQGFCFGFVEFETSSGKQSALEASPVTIGDRQAVVEEKKTNSRGGGNNGGSRGRYFSGRGSFRNES
FKGGRGGGGRGGYGRGGGEFSGRPKSSNPRNGGEGYQRVPQNGGGGRGGRGEGGRGGARGGGSS

SEQ ID NO: 22; XM_001110514.1 XM_001110514 name|PREDICTED: Macaca mulatta Ras-GTPase-activating protein SH3-domain-binding protein, transcript variant 2 (G3BP), coding sequence
ATGGTGATGGAGAAGCCTAGTCCCCTGCTGGTCGGGCGGGAATTTGTGAGACAATATTACACACTG
CTGAACCAGGCCCCAGACATGCTGCATAGATTTTATGGAAAGAACTCTTCTTATGTCCATGGGGA
TTGGATTCAAATGGAAAGCCAGCAGATGCAGTCTACGGACAGAAAGAAATCCACAGGAAAGTGATG
TCACAAAATTTCACCAACTGCCACACCAAGATTCGCCATGTTGATGCTCATGCCACGCTAAATGAT
GGTGTGGTAGTCCAGGTGATGGGCTTCTCTCTAACAACAACCAGGCTTTGAGGAGATTCATGCAA
ACGTTTGTCCTTGCTCCTGAGGGGTCTGTTGCAAATAAATTCTATGTTCACAATGATATCTTCAGA
TACCAAGATGAGGTCTTTGGTGGGTTTGTCACTGAGCCTCAGGAGGAATCTGAAGAAGAAGTAGAG
GAACCTGAAGAAAGACAGCAAACACCTGAGGTGGTACCTGATGATTCTGGAACTTTCTATGATCAG
GCAGTTGTCAGTAATGACATGGAAGAACATTTAGAGGAGCCTGTTGCTGAACCAGAGCCTGATCCT
GAACCAGAACCAGAACAAGAACCTGTATCTGAAATCCAAGAGGAAAAGCCTGAGCCAGTATTAGAA
GAAACTGCTCCTGAGGATACTCAGAAGAGTTCTTCTCCAGCACCTGCAGACATAGCTCAGACAGTA
CAGGAAGACTTGAGGACGTTTTCTTGGGCATCTGTGACCAGTAAGAACCTTCCACCCAGTGGAGCT
GTTCCAGTTACTGGGATACCACCTCATGTTGTTAAAGTACCAGCTTCACAGCCCCGTCCAGAGTCT
AAGCCTGAATCTCAGATTCCACCACAGAGACCAGTCCGTGAGGCTGGTGAGCAAGGTGACATTGAA
CCCCGAAGAATGGTGAGACACCCTGACAGTCACCAACTCTTCATTGGCAACCTGCCTCATGAAGTG
GACAAATCAGAGCTTAAAGATTTCTTTCAAAATTATGGGAACGTGGTGGAGTTGCGCATTAACAGT
GGTGGGAAATTACCCAATTTTGGTTTTGTTGTGTTTGATGATTCTGAGCCTGTTCAGAAGGTCCTT
AGCAACAGGCCTATCATGTTCAGAGGTGAGGTCCGTCTGAATGTCGAAGAGAAGAAGACTCGAGCT
GCCAGGGAAGGCGACCGACGAGATAATCGCCTTCGGGGACCTGGAGGCCCTCGAGGTGGCTGGGT
GGTGGAATGAGAGGCCCTCCCCGTGGAGGCATGGTGCAGAAACCAGGATTTGGAGTGGGAAGGGGG
CTTGCGCCACGGCAGTGA

SEQ ID NO: 23; XP_001110514 Ras-GTPase-activating protein SH3-domain-binding protein isoform 2 [Macaca mulatta] organism|macaca mulatta (rhesus monkey)
MVMEKPSPLLVGREFVRQYYTLLNQAPDMLHRFYGKNSSYVHGGLDSNGKPADAVYGQKEIHRKVM
SQNFTNCHTKIRHVDAHATLNDGVVVQVMGLLSNNNQALRRFMQTFVLAPEGSVANKFYVHNDIFR
YQDEVFGGFVTEPQEESEEEVEEPEERQQTPEVVPDDSGTFYDQAVVSNDMEEHLEEPVAEPEPDP
EPEPEQEPVSEIQEEKPEPVLEETAPEDTQKSSSPAPADIAQTVQEDLRTFSWASVTSKNLPPSGA
VPVTGIPPHVVKVPASQPRPESKPESQIPPQRPVREAGEQGDIEPRRMVRHPDSHQLFIGNLPHEV
DKSELKDFFQNYGNVVELRINSGGKLPNFGFVVFDDSEPVQKVLSNRPIMFRGEVRLNVEEKKTRA
AREGDRRDNRLRGPGGPRGGLGGGMRGPPRGGMVQKPGFGVGRGLAPRQ

SEQ ID NO: 24; AB236847 Trifolium pratense RNA for hypothetical protein, clone: C465.
ATGGCGTCTTCGTATCCTGGTTCCGTTAGTGCCGCTCAGGTTGGTTCTTACTTCGTTGGACAGTAC
TATCAAGTTCTTCGTCAACAACCTGATCTTGTTCATCAGTTTTACTCTGATTCCAGTTCCATGATT
CGTGTTGATGGTGATTATTCTGAGACTGCATCTGATGTGTTGCATATTCATAATATTGTGACATCA
CTGAATTTTTCGACAATTGAGATCAAGACGATCAATTCTCTTGACTCTTGGATGGAGGAGTGATT
GTGATGGTCACGGGTGTTGTTAAGATCAAGGATGTGAACAGGAAGCAGAAGTTTGTTCAGACTTTC
TTCCTTGCCCCTCAGGAGAAGGGTTATTTTGTGCTCAACGATATATTTCAATTTGTTCATGAGGAA FIGURE 5 (continued)

```
GTAGTGCATCCAAATCTGGTACCGGTGACCTCTGAAAAGATTGACTCACAGCCACATGTGTCTGCT
TCTTTTGCTGAGCCACCAGCTTCAGACTATGGTTTTGAGGAAGAAGCAAGGGAATATGTCAACTCA
GTTCATATAGACGATGATCCGGTGGACAAGTATAGTCTTCCTGAGCAGCATCAGCAGCTACAAGAA
GATTTCGAATCTGAAGTTGTGGTGGAGGAAACTCCTGCACAGGAGGCATCTCCACAGGTGTATAGT
GTTGCACAAACTATCCGTGAAACCCCTGTTGCTCATGTGGAAGAGTCGTATGAGGAGCCTGCTAAG
AAAACTTATGCATCTATTTTACGTGTCGCCAAAGGCCAATCAGTGGTGTCCGCTGCACCACAACAT
GCTCCACAGCATTCTTTTAAAAGTGCTCCTCCTCCTTCCGATTTTAATCATGTCACACAGCCTGCT
GTTCAGCAGTCAGTGGTGCAGCCTGCGTTTCAGCAGTCAAGATCAGCATCTACATATGTTTCAGAG
TCTGGGGCTGAGGCAACAGAAGAAAGCTACAAATTTGAAGAAGAAGAAGTAACATCTGTCTATGTG
AGAAACCTGCCTGGTGATATTACCGAAGCGGAGATTGAGGAGGAGTTCAAGAGTTTCGGCAGAATT
AAGCCAGATGGAATATTTGAAATTGGAGTTTGCTATGCATTTGTTGAATTCGAAGACGTTGTTGGC
GTTCAAAATGCACTTCAGGCTTCTCCCATACAATTGGCTGGTAGACAAATATACATAGAGGAGCGA
AGACCAAGCAGCGGCGGTGCAGCTCGAGGAGGAAGAGGAAGGGGAAGAGGCAGAGGCGGTTATCCA
ACAGATGCTCCAAGAGGGCGTTTTGGTGGCAGGAGCTCGGGAAGGGGTTATTATCAGGATACCTCA
GACTATACCAGGAGCTCGGGAAGAGGTGATGGTTATCTTCAGCGCGGTTCACGATAG
```

SEQ ID NO: 25; BAE71299.1, Trifolium pratense RNA for hypothetical protein
```
MASSYPGSVSAAQVGSYFVGQYYQVLRQQPDLVHQFYSDSSSMIRVDGDYSETASDVLHIHNIVTS
LNFSTIEIKTINSLDSWDGGVIVMVTGVVKIKDVNRKQKFVQTFFLAPQEKGYFVLNDIFQFVHEE
VVHPNLVPVTSEKIDSQPHVSASFAEPPASDYGFEEEAREYVNSVHIDDDPVDKYSLPEQHQQLQE
DFESEVVEETPAQEASPQVYSVAQTIRETPVAHVEESYEEPAKKTYASILRVAKGQSVVSAAPQH
APQHSFKSAPPPSDFNHVTQPAVQQSVVQPAFQQSRSASTYVSESGAEATEESYKFEEEEVTSVYV
RNLPGDITEAEIEEEFKSFGRIKPDGIFEIGVCYAFVEFEDVVGVQNALQASPIQLAGRQIYIEER
RPSSGGAARGGRGRGRGRGGYPTDAPRGRFGGRSSGRGYYQDTSDYTRSSGRGDGYLQRGSR
```

SEQ ID NO: 26; XM_473137.1 Oryza sativa (japonica cultivar-group), GSBP-like coding sequence
```
ATGGGGGGGCGGTACCACATGGAGATGCCCACCGGGATGAGGGAGCTGGACCGCGTGCAGCAGCAG
ATCGCCAGCCACCCCTACGCCTTCGAGGTGTGCTCCTACTTCTTGCAGGGGTACTACAACGTGCTC
GCGAACAGCCCGGAGCTGGCGTGCCAATTCTACACGGATTACAGCACCGCCGTGAGGCTGGACTGC
CAGACGATGAAATCCTCGTTCGGGGAGACTGTTGAGGAAATCAATGACATGATCATATCCATGAAT
GTACACAAGATTGAGGTTAAGACAGCTAATTTCGTGCAGTCATGGGTGGGGCTCTCCAGATGTTG
GTTACTGGCCTAGTGCAATTAAAGGACTACCCTGTTCGCAAGAGATTTGCTCAGACTATGCTTCTT
GCTCCTCAGGATAATGGATATTATGTATTCAGTGACATCTTTAAGCTTATCTGTGATGAATATGAT
TACTATGAAGGGGCTGATTACAGTCACACTGACAACATTCTCCAGATGGATGCTCATAATACCATG
ACTGAAACAGCGTCTGATTGTATGCCTGAAGAACTTGAGGCAAAGGAAGCTTTAGCTCCTGCTGAT
ATTGAGGAAGGGGTCCTGCTTTTATGCCTGAAAATCATGAAGTTCAGCAGCAAGATCCTTTGGAA
TATGGGGTTGTGATCGACGATGATTCTCCTTCTGAAGAGCTTACTCCTTCGTTCCCCAGTTCTACT
GACAGTAAACAGGATGCACCTCTTGGCCCCATTGTCCATCCTTCTGTAACTACCCCTGAGGAAGAG
CCTATGGGAGAACCAGCCAAACAAACATACGCTTCAGTGCTGCGAACAAAAGGACACCCTAGCCAT
CAGGCTATTCACTCCATTCCTCTCAACAAGGCCACGGCAAGTAGTGTGGAGTCACAACTGAATGGA
CATATGACTAAGCAGGTGCAGCCTGTGCATGAAAAAGCCAACCTGGACACCCGTTATGATGCTAGC
GGCCCTGAGGATGAAGAAGAGTTTTTGTCAGTTTATATCGGGAACCTTTCTCCATCTACTTCAGTC
TTTGATCTTGAGAAGGTATTCCAGGCTTTTGGAAGAATTAAACCTGACGGGGTTGCTATACGGAGC
CGCAAGGAGGCTGGAATTTTCTTTGGCTTTGTTGAGTACGAAGACATGTCTGGTATCCATAATGCT
```

FIGURE 5 (continued)

TTGAGGGCATCTCCAATAGAGCTGAATGGCCGCTTAATACATGTTGAAGAGAGGAGGCAAATCTAT
CGGGGAGGTGGAGCAAGACGGGGGAGAGGAAGACCTGCTGACTTCTCTAGGGGTCAATCGGGTGGG
CGGTATGATGGGGATTATGCTACTCGGTCAAAGGGAAATGGGTACCAAAGAAGGGTTTGA

SEQ ID NO: 27; genpept|50926380, CAE03370, Oryza sativa (japonica cultivar-group),GSBP-like
MGGRYHMEMPTGMRELDRVQQQIASHPYAFEVCSYFLQGYYNVLANSPELACQFYTDYSTAVRLDC
QTMKSSFGETVEEINDMIISMNVHKIEVKTANFVQSWGGALQMLVTGLVQLKDYPVRKRFAQTMLL
APQDNGYYVFSDIFKLICDEYDYYEGADYSHTDNILQMDAHNTMTETASDCMPEELEAKEALAPAD
IEERGPAFMPENHEVQQQDPLEYGVVIDDDSPSEELTPSFPSSTDSKQDAPLGPIVHPSVTTPEEE
PMGEPAKQTYASVLRTKGHPSHQAIHSIPLNKATASSVESQLNGHMTKQVQPVHEKANLDTRYDAS
GPEDEEEFLSVYIGNLSPSTSVFDLEKVFQAFGRIKPDGVAIRSRKEAGIFFGFVEYEDMSGIHNA
LRASPIELNGRLIHVEERRQIYRGGGARRGRGRPADFSRGQSGGRYDGDYATRSKGNGYQRRV SEQ ID NO: 28; (gi|44886170:53494-53634, 54497-54803, 55118-55407, 55491-55644, 55761-55882, 55973-56032, 56266-56320, 56591-56829) Medicago truncatula clone mth2-99p24, complete sequence
ATGGTTGGCAATGCTTTTGTGGAGCAGTATTACTCAATTCTGCACCGCGACCCGGATCAGGTTCAT
AGGTTTTACCACGACTCAAGTGTCATGAGTCGACCTGAGGAGGATGGTACCATGACAACTGTCACC
ACCACTGCAGAAATTGATAAAAAGATACAATCTCTCGAGTACACAAGCTTTAGGGTGGAGGTTCTG
AGTGCTGATGCTCAGCCTTCATATAATAATGGAGTGATGGTTGTAGTGACTGGCTGCTTGACTGGA
ACTGACAATATTAAACGCAAGTTTGCGCAGTCATTTTTCCTGGCTCCACAGGACAAGGGCTTCTAT
GTTTTGAATGATGTTTTTAGATATGTTGATGCGTATAAGTCAATTGATATCGAGTCTGTGCCAGCA
AATGATGCTGATGAAAGTGCTCCATCAGAAGCTATTATTACACCCGAGCCTGAGCCTGTTCATGTT
CCTGAAGTCATTCCACCCACTCAAACTGTTATTCCAACTGCTCAAACTGTTATTCCACCCACTCAA
ACTGTTATTGCTGATACTGAAACTATCATCAGTAAAGAAGTGAGCTTGCCACTGGAGAATGGAAAA
TTATCAGTTACTGAAAATGTGATTCCTGTTAATCATGTTAAAGAGTCAAGTCATCATGTTAAGGAA
CCGGAACAACCCACAAGCATTGAGAAAGTTGCTTCCAATACACAGGAGGATACTCCAAAAAAGTCC
TTTGCATCCATTGTGAATGCCTTGAAAGATAATTCCGCTCCCTTCCATTTGAGGGCTTCTCCTGCT
AAACCAGCTGTGCACCCACCCCGTGTACATAGCGTGCCTGCTCCTGAAGCACCAACCCCTAACATG
GACATTCCATTGGAAAAGAATAATGAGAATGCAGGTAGGGCTCATGCAATATTTGTTGCAAATTTG
CCTATGAGTGCAACAGTAGAGCAATTGGATCGGGCTTTCAAGAAATTCGGGCCCATTAAGCGTGAT
GGTATTCAAGTCAGAAGTAACAAGGGGTCTTGTTTTGGTTTTGTGGAGTTTGAATCTGCTGCTTCA
ATGCAAAGTGCCCTAGAGGCCTCTCCTCCTGTTATGTTGGACAACCGTAGACTTTCCATTGAAGAA
AGGAGAGGGCGTAGTGGATACCGAAATGACAGAAATGATAACTTCAGGGGCCGTGGCAACTTTGGT
GGCGGCCGTGGGGGTGGCTTTAACGGAAGGAACGATTTTGAGAGGCGAGGAGGTGAGTTCTCTGGC
CGATCTCGAGGAGGCCAGAATGCCGGGCGAAGCAATGGAGATGCTGTGCCAAGGAGTTATCAGAAT
GGAGGAGGAAAAGTCGCTGCTCGTCAACCACCAGTGAAAGTTCAATAA SEQ ID NO: 29; Q1SBN7_MEDTR|Q1SBN7 RNA-binding protein-like Medicago truncatula
MVGNAFVEQYYSILHRDPDQVHRFYHDSSVMSRPEEDGTMTTVTTTAEIDKKIQSLEYTSFRVEVL
SADAQPSYNNGVMVVVTGCLTGTDNIKRKFAQSFFLAPQDKGFYVLNDVFRYVDAYKSIDIESVPA
NDADESAPSEAIITPEPEPVHVPEVIPPTQTVIPTAQTVIPPTQTVIADTETIISKEVSLPLENGK
LSVTENVIPVNHVKESSHHVKEPEQPTSIEKVASNTQEDTPKKSFASIVNALKDNSAPFHLRASPA
KPAVHPPRVHSVPAPEAPTPNMDIPLEKNNENAGRAHAIFVANLPMSATVEQLDRAFKKFGPIKRD
GIQVRSNKGSCFGFVEFESAASMQSALEASPPVMLDNRRLSIEERRGRSGYRNDRNDNFRGRGNFG
GGRGGGFNGRNDFERRGGEFSGRSRGGQNAGRSNGDAVPRSYQNGGGKVAARQPPVKVQ FIGURE 5 (continued)

SEQ ID NO: 30; gi|38327550:172-1572 Homo sapiens GTPase activating
protein (SH3 domain) binding protein 1 (G3BP1), transcript variant
1, mRNA (encodes a shorter version of SEQ ID NO: 31)
ATGGTGATGGAGAAGCCTAGTCCCCTGCTGGTCGGGCGGGAATTTGTGAGACAGTATTACACACTG
CTGAACCAGGCCCCAGACATGCTGCATAGATTTTATGGAAAGAACTCTTCTTATGTCCATGGGGA
TTGGATTCAAATGGAAAGCCAGCAGATGCAGTCTACGGACAGAAAGAAATCCACAGGAAAGTGATG
TCACAAAACTTCACCAACTGCCACACCAAGATTCGCCATGTTGATGCTCATGCCACGCTAAATGAT
GGTGTGGTAGTCCAGGTGATGGGGCTTCTCTCTAACAACAACCAGGCTTTGAGGAGATTCATGCAA
ACGTTTGTCCTTGCTCCTGAGGGTCTGTTGCAAATAAATTCTATGTTCACAATGATATCTTCAGA
TACCAAGATGAGGTCTTTGGTGGGTTTGTCACTGAGCCTCAGGAGGAGTCTGAAGAAGAAGTAGAG
GAACCTGAAGAAAGACAGCAAACACCTGAGGTGGTACCTGATGATTCTGGAACTTTCTATGATCAG
GCAGTTGTCAGTAATGACATGGAAGAACATTTAGAGGAGCCTGTTGCTGAACCAGAGCCTGATCCT
GAACCAGAACCAGAACAAGAACCTGTATCTGAAATCCAAGAGGAAAAGCCTGAGCCAGTATTAGAA
GAAACTGCCCCTGAGGATGCTCAGAAGAGTTCTTCTCCAGCACCTGCAGACATAGCTCAGACAGTA
CAGGAAGACTTGAGGACATTTTCTTGGGCATCTGTGACCAGTAAGAATCTTCCACCCAGTGGAGCT
GTTCCAGTTACTGGGATACCACCTCATGTTGTTAAAGTACCAGCTTCACAGCCCCGTCCAGAGTCT
AAGCCTGAATCTCAGATTCCACCACAAAGACCTCAGCGGGATCAAAGAGTGCGAGAACAACGAATA
AATATTCCTCCCCAAAGGGGACCCAGACCAATCCGTGAGGCTGGTGAGCAAGGTGACATTGAACCC
CGAAGAATGGTGAGACACCCTGACAGTCACCAACTCTTCATTGGCAACCTGCCTCATGAAGTGGAC
AAATCAGAGCTTAAAGATTTCTTTCAAAGTTATGGAAACGTGGTGGAGTTGCGCATTAACAGTGGT
GGGAAATTACCCAATTTTGGTTTTGTTGTGTTTGATGATTCTGAGCCTGTTCAGAAAGTCCTTAGC
AACAGGCCCATCATGTTCAGAGGTGAGGTCCGTCTGAATGTCGAAGAGAAGAAGACTCGAGCTGCC
AGGGAAGGCGACCGACGAGATAATCGCCTTCGGGGACCTGGAGGCCCTCGAGGTGGGCTGGGTGGT
GGAATGAGAGGCCCTCCCCGTGGAGGCATGGTGCAGAAACCAGGATTTGGAGTGGGAAGGGGGCTT
GCGCCACGGCAGTGA SEQ ID NO: 31; EAW61662.1| Ras-GTPase-activating protein SH3-
domain-binding protein, isoform CRA_c [Homo sapiens]
MQLQPTSHCSFMRASELEPLGQAVPKFLTLRNCVELTKAMVMEKPSPLLVGREFVRQYYTLLNQAP
DMLHRFYGKNSSYVHGGLDSNGKPADAVYGQKEIHRKVMSQNFTNCHTKIRHVDAHATLNDGVVVQ
VMGLLSNNNQALRRFMQTFVLAPEGSVANKFYVHNDIFRYQDEVFGGFVTEPQEESEEEVEEPEER
QQTPEVVPDDSGTFYDQAVVSNDMEEHLEEPVAEPEPDPEPEPEQEPVSEIQEEKPEPVLEETAPE
DAQKSSSPAPADIAQTVQEDLRTFSWASVTSKNLPPSGAVPVTGIPPHVVKVPASQPRPESKPESQ
IPPQRPQRDQRVREQRINIPPQRGPRPIREAGEQGDIEPRRMVRHPDSHQLFIGNLPHEVDKSELK
DFFQSYGNVVELRINSGGKLPNFGFVVFDDSEPVQKVLSNRPIMFRGEVRLNVEEKKTRAAREGDR
RDNRLRGPGGPRGGLGGGMRGPPRGGMVQKPGFGVGRGLAPRQ SEQ ID NO: 32, gi|57015207:c>15550296-15550273, c15550161-
15549828, c15549739-15549487, c15548780-15548668, c15548583-
15548462, c15548369-15548304, c15546867-15546801, c15546375-
<15546125) Oryza sativa (indica cultivar-group) chromosome 4,
whole genome shotgun sequence
ATGGACACCGTCACCACCATGGAGGCGATTAACGCGAAGATCGTGTCCATGGACATCGTGCGGGCG
GAGATCAAGGCGGTGGACGCGCAGGAGTCGCTGGGCGGGGCGTCACGGTGCTCGTCACGGGCCAC
CTCACCGGGAGCGACGACGTGCGCAGGGAGTTCTCGCAGTCCTTCTTCCTCGCCGCAGGAGAAG
GGATACTTCGTGCTCAACGACATCCTGCGCTACGTCGGGGGGAGGGGATCAGGAGGTGGAGCCG
GAGCCGGAGCTGGAGCTGTCGTTTCCGCCGTCGCAGCAGCCGGATTCGGTGCCTGCTCCTTCGGCG
AATGGCACTAGCGTGCCGCGGGAACAGGAGGCCTTCTCGCAGCCGGAGCAGCATGTGGCTGATCCT FIGURE 5 (continued)

```
GCACCCAATGCTCAGGAGGCTGATCTCAACGGCGAGGAGGTTTATAACCCACCGAACAACACAGAG
GGGCCTGTTGTGGAGGAAACGCCGATTCCTGAAGTTATAGATGAAGTGCCAAATAACGTAGCTGTG
GCTATGCCGACTCCGTCTGCCCTGCCCCTGCCCCTGCCCCTGTACCACAAGAGGAGGCCCCCAAGA
AGTCGTATGCTTCAATTGCCGGCACCACCAAAACAAGAGAAGCAAGTTGCTCCTGCACCTGTTGCT
CCGGTTGCTGATGCTCCAACTTTCAGTCCTAATCCTGAAAGCAGCAACATTCAAGAGGCTGAAGTT
GATGCACATGCGATATATGTACGGAATCTGCCTTTAAGTGCCACGCCTGAACAATTAGAAGAAGCA
TTCAAGAAATTTGGCGCTATCAAGCCGGACGGAATCCAAGTTAGAAGTCACAAGATTCAAGGGTTC
TGCTATGGGTTTGTAGAGTTTGAAGATCCCAGTTCAGTTCAAAGTGCAATTGCGGGTTCTCCTGTG
ACGATTAGTGACCGGCAATGTTATGTGGAGGAAAAGAGAACTGCTGGTTCACGTGGTGGTGGCAGA
GGAAGGTTTGCTCCTGGTAGAGGTGGTAACTTCCGAGGTGAAGGCATGAGAGGCCGCGGGAATTAC
ACCGGAGGGAGGGGCTATGGAAGGGGTGAGTTCAATTATCGATCCGACTATGGAGGCAGAGGCGCT
GGTAGAGGTGGTTCATCACGTGGTGGTGATGTTGGCTACCAGCGGGTTGACCACTCTGCTGGTCGT
GCTGCTCGGGCGCCATCGGGCACTAGTGCCGTTGCAAAGTGA
```

SEQ ID NO: 33; A2XSG1_ORYSI|A2XSG1 EAY93771, Hypothetical protein Oryza sativa (indica cultivar-group)
```
MDTVTTMEAINAKIVSMDIVRAEIKAVDAQESLGGGVTVLVTGHLTGSDDVRREFSQSFFLAPQEK
GYFVLNDILRYVGGEGDQEVEPEPELELSFPPSQQPDSVPAPSANGTSVPREQEAFSQPEQHVADP
APNAQEADLNGEEVYNPPNNTEGPVVEETPIPEVIDEVPNNVAVAMPTPSALPLPLPLYHKRRPPR
SRMLQLPAPPKQEKQVAPAPVAPVADAPTFSPNPESSNIQEAEVDAHAIYVRNLPLSATPEQLEEA
FKKFGAIKPDGIQVRSHKIQGFCYGFVEFEDPSSVQSAIAGSPVTISDRQCYVEEKRTAGSRGGGR
GRFAPGRGGNFRGEGMRGRGNYTGGRGYGRGEFNYRSDYGGRGAGRGGSSRGGDVGYQRVDHSAGR
AARAPSGTSAVAK
```

SEQ ID NO: 34; conserved motif 1
GIQVR

SEQ ID NO: 35; conserved motif 2
(V/I)EE(K/R)(R/K)

SEQ ID NO: 36; conserved motif 3
(C/F/N)(F/Y/I)(G/A)F(I/V)(E/A/V)(F/Y)(E/D)

SEQ ID NO: 37; conserved motif 4
F(K/R/Q)(K/S/A/N)(F/Y)G(A/L/T/P/R/N)(I/V)(K/R/V)

SEQ ID NO: 38; conserved motif 5
(S/A/Q)(V/I/L)(F/Y)(V/L/I)(K/R/A/G)(S/H/N/G)L(P/S)

SEQ ID NO: 39; conserved motif 6
(Y/F)(V/F/Y)V(L/F/H)(N/S)D(I/M/V/T)(F/L)(R/Q/K)(F/Y/L)

SEQ ID NO: 40; conserved motif 7
F(T/S/A/V/M)Q(S/T)(F/M)(F/L/V)L(A/V)(P/S)

SEQ ID NO: 41; conserved motif 8 (wherein X may be any amino acid, preferably one of L, H, T, I, V, M, or Q)
(G/A)(V/L/Y)X(I/V/T/M)(V/L/M/Q)V(T/M)G FIGURE 5 (continued)

SEQUENCE LISTING

```
<160> NUMBER OF SEQ ID NOS: 47

<210> SEQ ID NO 1
<211> LENGTH: 1515
<212> TYPE: DNA
<213> ORGANISM: Oryza sativa

<400> SEQUENCE: 1
gtacaaaaaa gcaggcttaa acaatggcag tgcaagctgg aacccagct  actcctataa      60 gcccccaagt gattagtggt gcatttgttc agcaatatta ccacattcta catgagacac     120
cagatcaggt ctataagttc tatcaagatg caagtattgt tggtcggcct gattctaatg     180
```

```
gagtcatgaa atatgtatca acaactgctg atatcaacaa acaatcttg tctatggact    240
tcagcaacta cttaacagag atagagactg cagatgcaca gttatctcac caggatggtg    300
tgctcattgt tgttactgga tctttgacat ctgaaggcat atgccgtaga tttacacagt    360
cattcttcct tgcaccacaa gaatctggtg gctatgttgt tctcaatgat atttttagat    420
ttatagtgga aaggccacca gttgcaataa gtcaagttag tcaagaaaat gagaacaatc    480
agaacactgc cactcttcct gaaactgatc ctaatccagc gggagatggt atgatctcag    540
agcctgtggc agtggaaaat aatgttgcgg aggggggaagt gacaaattcc acggttgatg   600
gcactagtat tgaaaataat gctactgctg ctgtcgaacc acctgtacaa atgacgaaag    660
aggagcccag gaagatctct gttgctgctc ctccccctcc agctcagaag gatgtaacga    720
agaagtccta tgcgtcgatt gtgaaggtta tgaaggaggt gtcactaacc ccagttgtca    780
aacctaagcc agctccaaaa catgtggtta agactgttga agcttcagag aaaccttctg    840
ttaaaagttc tcaaactgtt gaaatcactc cgaatgataa caacgatgct gaaaataaca    900
cttctaatga tgagcaaggt tactcagttt ttgtgaagag tttgcctcac aatgtgacag    960
tccagacggt tgaggaagag ttcaagaaat ttggcgctat caagccaggt ggcatccaag   1020
ttaggaacaa caagattgac cggttctgct ttggtttat tgagtttgag tcccagcaat    1080
ctatgcaggc agcaattgag gcatctccga ttcatgggtg gggaaagaa gtatttgttg    1140
aggagaaaag aaccactacc cgagttgtga atggtgttgt catcacgcgt ggtgataatg    1200
ggaatgctgg tggaggcgga cgttaccaat ctggaagggg aggctaccgc ggtgataatt    1260
tcaggggacg gggtggtggc tatgcgaaca gcggaaacta ccgtggaggt gataacttca    1320
gcaggaggaa cgacttgaga aatcgcaacg agttttcagg tcgtggtcga gggccaccgc    1380
ctgggaatgg ctatcagaac aacggattcc atccagcaag gccgttccag aacggaaatg    1440
ggaggttcac ccgagtcaac ggccctaggc aaacaccggt tgcggcatag aggagggcaa    1500
tgatgaccca gctttt                                                   1515
```

<210> SEQ ID NO 2
<211> LENGTH: 488
<212> TYPE: PRT
<213> ORGANISM: Oryza sativa

<400> SEQUENCE: 2

```
Met Ala Val Gln Ala Gly Thr Pro Ala Thr Pro Ile Ser Pro Gln Val
1               5                   10                  15

Ile Ser Gly Ala Phe Val Gln Gln Tyr Tyr His Ile Leu His Glu Thr
                20                  25                  30

Pro Asp Gln Val Tyr Lys Phe Tyr Gln Asp Ala Ser Ile Val Gly Arg
            35                  40                  45

Pro Asp Ser Asn Gly Val Met Lys Tyr Val Ser Thr Thr Ala Asp Ile
        50                  55                  60

Asn Lys Thr Ile Leu Ser Met Asp Phe Ser Asn Tyr Leu Thr Glu Ile
65                  70                  75                  80

Glu Thr Ala Asp Ala Gln Leu Ser His Gln Asp Gly Val Leu Ile Val
                85                  90                  95

Val Thr Gly Ser Leu Thr Ser Glu Gly Ile Cys Arg Arg Phe Thr Gln
            100                 105                 110

Ser Phe Phe Leu Ala Pro Gln Glu Ser Gly Gly Tyr Val Val Leu Asn
        115                 120                 125

Asp Ile Phe Arg Phe Ile Val Glu Arg Pro Pro Val Ala Ile Ser Gln
```

```
                130                 135                 140
Val Ser Gln Glu Asn Glu Asn Gln Asn Thr Ala Thr Leu Pro Glu
145                 150                 155                 160

Thr Asp Pro Asn Pro Ala Gly Asp Gly Met Ile Ser Glu Pro Val Ala
                165                 170                 175

Val Glu Asn Asn Val Ala Glu Gly Glu Val Thr Asn Ser Thr Val Asp
                180                 185                 190

Gly Thr Ser Ile Glu Asn Asn Ala Thr Ala Ala Val Glu Pro Pro Val
                195                 200                 205

Gln Met Thr Lys Glu Glu Pro Arg Lys Ile Ser Val Ala Ala Pro Pro
210                 215                 220

Pro Pro Ala Gln Lys Asp Val Thr Lys Lys Ser Tyr Ala Ser Ile Val
225                 230                 235                 240

Lys Val Met Lys Glu Val Ser Leu Thr Pro Val Lys Pro Lys Pro
                245                 250                 255

Ala Pro Lys His Val Val Lys Thr Val Glu Ala Ser Glu Lys Pro Ser
                260                 265                 270

Val Lys Ser Ser Gln Thr Val Glu Ile Thr Pro Asn Asp Asn Asn Asp
                275                 280                 285

Ala Glu Asn Asn Thr Ser Asn Asp Glu Gln Gly Tyr Ser Val Phe Val
                290                 295                 300

Lys Ser Leu Pro His Asn Val Thr Val Gln Thr Val Glu Glu Phe
305                 310                 315                 320

Lys Lys Phe Gly Ala Ile Lys Pro Gly Gly Ile Gln Val Arg Asn Asn
                325                 330                 335

Lys Ile Asp Arg Phe Cys Phe Gly Phe Ile Glu Phe Glu Ser Gln Gln
                340                 345                 350

Ser Met Gln Ala Ala Ile Glu Ala Ser Pro Ile His Met Gly Gly Lys
                355                 360                 365

Glu Val Phe Val Glu Glu Lys Arg Thr Thr Arg Val Val Asn Gly
                370                 375                 380

Val Val Ile Thr Arg Gly Asp Asn Gly Asn Ala Gly Gly Gly Arg
385                 390                 395                 400

Tyr Gln Ser Gly Arg Gly Gly Tyr Arg Gly Asp Asn Phe Arg Gly Arg
                405                 410                 415

Gly Gly Gly Tyr Ala Asn Ser Gly Asn Tyr Arg Gly Gly Asp Asn Phe
                420                 425                 430

Ser Arg Arg Asn Asp Leu Arg Asn Arg Asn Glu Phe Ser Gly Arg Gly
                435                 440                 445

Arg Gly Pro Pro Pro Gly Asn Gly Tyr Gln Asn Asn Gly Phe His Pro
450                 455                 460

Ala Arg Pro Phe Gln Asn Gly Asn Gly Arg Phe Thr Arg Val Asn Gly
465                 470                 475                 480

Pro Arg Gln Thr Pro Val Ala Ala
                485

<210> SEQ ID NO 3
<211> LENGTH: 2194
<212> TYPE: DNA
<213> ORGANISM: Oryza sativa

<400> SEQUENCE: 3
aatccgaaaa gtttctgcac cgttttcacc ccctaactaa caatataggg aacgtgtgct      60
aaatataaaa tgagacctta tatatgtagc gctgataact agaactatgc aagaaaaact     120
```

| | |
|---|---|
| catccaccta ctttagtggc aatcgggcta aataaaaaag agtcgctaca ctagtttcgt | 180 |
| tttccttagt aattaagtgg gaaaatgaaa tcattattgc ttagaatata cgttcacatc | 240 |
| tctgtcatga agttaaatta ttcgaggtag ccataattgt catcaaactc ttcttgaata | 300 |
| aaaaaatctt tctagctgaa ctcaatgggt aaagagagag atttttttta aaaaaataga | 360 |
| atgaagatat tctgaacgta ttggcaaaga tttaaacata taattatata attttatagt | 420 |
| ttgtgcattc gtcatatcgc acatcattaa ggacatgtct tactccatcc caattttat | 480 |
| ttagtaatta aagacaattg acttatttt attatttatc ttttttcgat tagatgcaag | 540 |
| gtacttacgc acacactttg tgctcatgtg catgtgtgag tgcacctcct caatacacgt | 600 |
| tcaactagca acacatctct aatatcactc gcctatttaa tacatttagg tagcaatatc | 660 |
| tgaattcaag cactccacca tcaccagacc acttttaata atatctaaaa tacaaaaaat | 720 |
| aattttacag aatagcatga aagtatgaa acgaactatt taggttttc acatacaaaa | 780 |
| aaaaaaagaa ttttgctcgt gcgcgagcgc caatctccca tattgggcac acaggcaaca | 840 |
| acagagtggc tgcccacaga caacccaca aaaaacgatg atctaacgga ggacagcaag | 900 |
| tccgcaacaa ccttttaaca gcaggctttg cggccaggag agaggaggag aggcaaagaa | 960 |
| aaccaagcat cctccttctc ccatctataa attcctcccc ccttttcccc tctctatata | 1020 |
| ggaggcatcc aagccaagaa gagggagagc accaaggaca cgcgactagc agaagccgag | 1080 |
| cgaccgcctt ctcgatccat atcttccggt cgagttcttg gtcgatctct cccctcctcc | 1140 |
| acctcctcct cacagggtat gtgcctccct tcggttgttc ttggatttat tgttctaggt | 1200 |
| tgtgtagtac gggcgttgat gttaggaaag gggatctgta tctgtgatga ttcctgttct | 1260 |
| tggatttggg atagaggggt tcttgatgtt gcatgttatc ggttcggttt gattagtagt | 1320 |
| atggttttca atcgtctgga gagctctatg gaaatgaaat ggtttaggga tcggaatctt | 1380 |
| gcgattttgt gagtaccttt tgtttgaggt aaaatcagag caccggtgat tttgcttggt | 1440 |
| gtaataaagt acggttgttt ggtcctcgat tctggtagtg atgcttctcg atttgacgaa | 1500 |
| gctatccttt gtttattccc tattgaacaa aaataatcca acttgaaga cggtcccgtt | 1560 |
| gatgagattg aatgattgat tcttaagcct gtccaaaatt tcgcagctgg cttgtttaga | 1620 |
| tacagtagtc cccatcacga aattcatgga aacagttata atcctcagga cagggggatt | 1680 |
| ccctgttctt ccgatttgct ttagtcccag aattttttt cccaaatatc ttaaaaagtc | 1740 |
| actttctggt tcagttcaat gaattgattg ctacaaataa tgcttttata gcgttatcct | 1800 |
| agctgtagtt cagttaatag gtaataccc tatagtttag tcaggagaag aacttatccg | 1860 |
| atttctgatc tccattttta attatatgaa atgaactgta gcataagcag tattcatttg | 1920 |
| gattattttt tttattagct ctcacccctt cattattctg agctgaaagt ctggcatgaa | 1980 |
| ctgtcctcaa ttttgttttc aaattcacat cgattatcta tgcattatcc tcttgtatct | 2040 |
| acctgtagaa gttctttttt ggttattcct tgactgcttg attacagaaa gaaatttatg | 2100 |
| aagctgtaat cgggatagtt atactgcttg ttcttatgat tcatttcctt tgtgcagttc | 2160 |
| ttggtgtagc ttgccacttt caccagcaaa gttc | 2194 |

<210> SEQ ID NO 4
<211> LENGTH: 1264
<212> TYPE: DNA
<213> ORGANISM: Oryza sativa

<400> SEQUENCE: 4

| | |
|---|---|
| tcgacgctac tcaagtggtg ggaggccacc gcatgttcca acgaagcgcc aaagaaagcc | 60 |

```
ttgcagactc taatgctatt agtcgcctag gatatttgga atgaaaggaa ccgcagagtt      120
tttcagcacc aagagcttcc ggtggctagt ctgatagcca aaattaagga ggatgccaaa      180
acatgggtct tggcgggcgc gaaacacctt gataggtggc ttaccttta acatgttcgg      240 gccaaaggcc ttgagacggt aaagttttct atttgcgctt gcgcatgtac aattttattc      300
ctctattcaa tgaaattggt ggctcactgg ttcattaaaa aaaaagaat ctagcctgtt       360 cgggaagaag aggattttgt tcgtgagaga gagagagaga gagagagaga gagagagaga      420
gaaggaggag gaggattttc aggcttcgca ttgcccaacc tctgcttctg ttggcccaag      480
aagaatccca ggcgcccatg ggctggcagt ttaccacgga cctacctagc ctaccttagc      540
tatctaagcg ggccgaccta gtagccacgt gcctagtgta gattaaagtt gccgggccag      600
caggaagcca cgctgcaatg gcatcttccc ctgtccttcg cgtacgtgaa aacaaaccca      660
ggtaagctta gaatcttctt gcccgttgga ctgggacacc caccaatccc accatgcccc      720
gatattcctc cggtctcggt tcatgtgatg tcctctcttg tgtgatcacg gagcaagcat      780
tcttaaacgg caaaagaaaa tcaccaactt gctcacgcag tcacgctgca ccgcgcgaag      840
cgacgcccga taggccaaga tcgcgagata aataacaac caatgatcat aaggaaacaa       900
gcccgcgatg tgtcgtgtgc agcaatcttg gtcatttgcg ggatcgagtg cttcacagct      960
aaccaaatat tcggccgatg atttaacaca ttatcagcgt agatgtacgt acgatttgtt      1020
aattaatcta cgagccttgc tagggcaggt gttctgccag ccaatccaga tcgccctcgt      1080
atgcacgctc acatgatggc agggcagggt tcacatgagc tctaacggtc gattaattaa      1140
tcccggggct cgactataaa tacctcccta atcccatgat caaaaccatc tcaagcagcc      1200
taatcatctc cagctgatca agagctctta attagctagc tagtgattag ctgcgcttgt      1260
gatc                                                                  1264
```

<210> SEQ ID NO 5
<211> LENGTH: 54
<212> TYPE: DNA
<213> ORGANISM: Artificial sequence
<220> FEATURE:
<223> OTHER INFORMATION: primer: prm8784

<400> SEQUENCE: 5

```
ggggacaagt ttgtacaaaa aagcaggctt aaacaatggc agtgcaagct ggaa            54
```

<210> SEQ ID NO 6
<211> LENGTH: 50
<212> TYPE: DNA
<213> ORGANISM: Artificial sequence
<220> FEATURE:
<223> OTHER INFORMATION: primer: prm8783

<400> SEQUENCE: 6

```
ggggaccact ttgtacaaga aagctgggtc atcattgccc tcctctatgc                 50
```

<210> SEQ ID NO 7
<211> LENGTH: 496
<212> TYPE: PRT
<213> ORGANISM: Oryza sativa

<400> SEQUENCE: 7

```
Met Ala Val Gln Ala Gly Thr Pro Ala Thr Pro Ile Ser Pro Gln Val
1               5                   10                  15

Ile Ser Gly Ala Phe Val Gln Gln Tyr Tyr His Ile Leu His Glu Thr
            20                  25                  30
```

-continued

Pro Asp Gln Val Tyr Lys Phe Tyr Gln Asp Ala Ser Ile Val Gly Arg
    35                  40                  45

Pro Asp Ser Asn Gly Val Met Lys Tyr Val Ser Thr Thr Ala Asp Ile
    50                  55                  60

Asn Lys Ile Ile Leu Ser Met Asp Phe Ser Asn Tyr Leu Thr Glu Ile
65                  70                  75                  80

Glu Thr Ala Asp Ala Gln Leu Ser His Gln Asp Gly Val Leu Ile Val
                85                  90                  95

Val Thr Gly Ser Leu Thr Ser Glu Gly Ile Cys Arg Arg Phe Thr Gln
            100                 105                 110

Ser Phe Phe Leu Ala Pro Gln Glu Ser Gly Tyr Val Val Leu Asn
            115                 120                 125

Asp Ile Phe Arg Phe Ile Val Glu Arg Pro Val Ala Ile Ser Gln
    130                 135                 140

Val Ser Gln Glu Asn Glu Asn Gln Asn Thr Ala Thr Leu Pro Glu
145                 150                 155                 160

Thr Asp Pro Asn Pro Ala Gly Asp Gly Met Ile Ser Glu Pro Val Ala
                    165                 170                 175

Val Glu Asn Asn Val Ala Glu Gly Glu Val Thr Asn Ser Thr Val Asp
            180                 185                 190

Gly Thr Ser Ile Glu Asn Asn Ala Thr Ala Val Glu Pro Pro Val
            195                 200                 205

Gln Met Thr Lys Glu Glu Pro Arg Lys Ile Ser Val Ala Ala Pro Pro
    210                 215                 220

Pro Pro Ala Gln Lys Asp Val Thr Lys Ser Tyr Ala Ser Ile Thr
225                 230                 235                 240

Leu Thr Met Ile Ala Leu Gln Val Lys Val Met Lys Glu Val Ser Leu
                245                 250                 255

Thr Pro Val Val Lys Pro Lys Pro Ala Pro Lys His Val Val Lys Thr
                260                 265                 270

Val Glu Ala Ser Glu Lys Pro Ser Val Lys Ser Ser Gln Thr Val Glu
    275                 280                 285

Ile Thr Pro Asn Asp Asn Asn Asp Ala Glu Asn Asn Thr Ser Asn Asp
    290                 295                 300

Glu Gln Gly Tyr Ser Val Phe Val Lys Ser Leu Pro His Asn Val Thr
305                 310                 315                 320

Val Gln Thr Val Glu Glu Phe Lys Lys Phe Gly Ala Ile Lys Pro
            325                 330                 335

Gly Gly Ile Gln Val Arg Asn Asn Lys Ile Asp Arg Phe Cys Phe Gly
            340                 345                 350

Phe Ile Glu Phe Glu Ser Gln Gln Ser Met Gln Ala Ala Ile Glu Ala
        355                 360                 365

Ser Pro Ile His Met Gly Gly Lys Glu Val Phe Val Glu Glu Lys Arg
    370                 375                 380

Thr Thr Thr Arg Val Val Asn Gly Val Val Ile Thr Arg Gly Asp Asn
385                 390                 395                 400

Gly Asn Ala Gly Gly Gly Arg Tyr Gln Ser Gly Arg Gly Gly Tyr
            405                 410                 415

Arg Gly Asp Asn Phe Arg Gly Arg Gly Gly Tyr Ala Asn Ser Gly
        420                 425                 430

Asn Tyr Arg Gly Gly Asp Asn Phe Ser Arg Arg Asn Asp Leu Arg Asn
        435                 440                 445

Arg Asn Glu Phe Ser Gly Arg Gly Arg Gly Pro Pro Gly Asn Gly
450                 455                 460

-continued

Tyr Gln Asn Asn Gly Phe His Pro Ala Arg Pro Phe Gln Asn Gly Asn
465                 470                 475                 480

Gly Arg Phe Thr Arg Val Asn Gly Pro Arg Gln Thr Pro Val Ala Ala
            485                 490                 495

<210> SEQ ID NO 8
<211> LENGTH: 583
<212> TYPE: PRT
<213> ORGANISM: Oryza sativa

<400> SEQUENCE: 8

Met Pro Ser Arg Met Met Gln Ala Phe Ala Gln Glu Ala Ser Asp Phe
1               5                   10                  15

Asp Arg Gln Met Gly Cys Met Ala Gly Met Phe Gln Ile Phe Asp Arg
                20                  25                  30

Arg Arg Leu Leu Thr Ala Arg Gln Arg Gly Gly Ala Arg Gly Thr Ala
            35                  40                  45

Pro Pro Gly His Val Leu Pro Asn Ser Asn Ser Asn Val Ser Ile Gln
    50                  55                  60

Asn Pro Val Ala Ser Asn Asn Thr Leu Val Tyr Asp Asp Ala Arg
65                  70                  75                  80

Asp Gly Ala Ile Gly Phe Pro Met Ala Val Gln Ala Gly Thr Pro Ala
                85                  90                  95

Thr Pro Ile Ser Pro Gln Val Ile Ser Gly Ala Phe Val Gln Gln Tyr
            100                 105                 110

Tyr His Ile Leu His Glu Thr Pro Asp Gln Val Tyr Lys Phe Tyr Gln
        115                 120                 125

Asp Ala Ser Ile Val Gly Arg Pro Asp Ser Asn Gly Val Met Lys Tyr
130                 135                 140

Val Ser Thr Thr Ala Asp Ile Asn Lys Ile Ile Leu Ser Met Asp Phe
145                 150                 155                 160

Ser Asn Tyr Leu Thr Glu Ile Glu Thr Ala Asp Ala Gln Leu Ser His
                165                 170                 175

Gln Asp Gly Val Leu Ile Val Val Thr Gly Ser Leu Thr Ser Glu Gly
            180                 185                 190

Ile Cys Arg Arg Phe Thr Gln Ser Phe Phe Leu Ala Pro Gln Glu Ser
        195                 200                 205

Gly Gly Tyr Val Val Leu Asn Asp Ile Phe Arg Phe Ile Val Glu Arg
210                 215                 220

Pro Pro Val Ala Ile Ser Gln Val Ser Gln Glu Asn Glu Asn Asn Gln
225                 230                 235                 240

Asn Thr Ala Thr Leu Pro Glu Thr Asp Pro Asn Pro Ala Gly Asp Gly
                245                 250                 255

Met Ile Ser Glu Pro Val Ala Val Glu Asn Asn Val Ala Glu Gly Glu
            260                 265                 270

Val Thr Asn Ser Thr Val Asp Gly Thr Ser Ile Glu Asn Asn Ala Thr
        275                 280                 285

Ala Ala Val Glu Pro Pro Val Gln Met Thr Lys Glu Glu Pro Arg Lys
290                 295                 300

Ile Ser Val Ala Ala Pro Pro Pro Ala Gln Lys Asp Val Thr Lys
305                 310                 315                 320

Lys Ser Tyr Ala Ser Ile Thr Leu Thr Met Ile Ala Leu Gln Val Lys
                325                 330                 335

Val Met Lys Glu Val Ser Leu Thr Pro Val Val Lys Pro Lys Pro Ala
            340                 345                 350

Pro Lys His Val Val Lys Thr Val Glu Ala Ser Glu Lys Pro Ser Val
            355                 360                 365

Lys Ser Ser Gln Thr Val Glu Ile Thr Pro Asn Asp Asn Asn Asp Ala
        370                 375                 380

Glu Asn Asn Thr Ser Asn Asp Glu Gln Gly Tyr Ser Val Phe Val Lys
385                 390                 395                 400

Ser Leu Pro His Asn Val Thr Val Gln Thr Val Glu Glu Phe Lys
                405                 410                 415

Lys Phe Gly Ala Ile Lys Pro Gly Ile Gln Val Arg Asn Asn Lys
            420                 425                 430

Ile Asp Arg Phe Cys Phe Gly Phe Ile Glu Phe Glu Ser Gln Gln Ser
                435                 440                 445

Met Gln Ala Ala Ile Glu Ala Ser Pro Ile His Met Gly Gly Lys Glu
            450                 455                 460

Val Phe Val Glu Glu Lys Arg Thr Thr Thr Arg Val Val Asn Gly Val
465                 470                 475                 480

Val Ile Thr Arg Gly Asp Asn Gly Asn Ala Gly Gly Gly Arg Tyr
                485                 490                 495

Gln Ser Gly Arg Gly Gly Tyr Arg Gly Asp Asn Phe Arg Gly Arg Gly
            500                 505                 510

Gly Gly Tyr Ala Asn Ser Gly Asn Tyr Arg Gly Asp Asn Phe Ser
                515                 520                 525

Arg Arg Asn Asp Leu Arg Asn Arg Asn Glu Phe Ser Gly Arg Gly Arg
            530                 535                 540

Gly Pro Pro Pro Gly Asn Gly Tyr Gln Asn Asn Gly Phe His Pro Ala
545                 550                 555                 560

Arg Pro Phe Gln Asn Gly Asn Gly Arg Phe Thr Arg Val Asn Gly Pro
                565                 570                 575

Arg Gln Thr Pro Val Ala Ala
            580

<210> SEQ ID NO 9
<211> LENGTH: 2150
<212> TYPE: DNA
<213> ORGANISM: Oryza sativa

<400> SEQUENCE: 9
ctcctctctc cgtctcgctt cggttccttc ctcgagtcga aacctcgcga agccgccgcc      60
gccgccgccg actctcgcta gggctagggt tttcctcccg ccgccgggag cccctccccc     120
tgcaaccgcg caagggatgg ctatgcaagt tggggaatca gttgctcctt taagtccaca     180
aatgattgga aatgcgtttg ttcaacaata ctacaatgtt ctccatagtt caccgggtca     240
agtttgtaag ttctatcatg attcaagcac ccttggtcga ccagattcta atggaaccat     300
gacatctgta accacattga ctgctatcaa cgatgaattt ctctctacgg acttcagtag     360
ctgtttgatt aagttagaga atgtggatgc acagttatcc ctcaatggtg gtgtgcacat     420
tttggtaact ggatctattg gacacaatgg cactatgagg catagattta gccagtcatt     480
cttccttgct ccacaagaaa gcggaggcta ttttgttctg aatgatatgc taagatatga     540
ttctctgcaa gaaacactgt tgactgagac aaatgattct ccacaagaaa gactgttgac     600
tgagataaat gattctctgc taaccatgt tgatgataac actcacagtg tcacatttac      660
atctgagcca gagacttcag gcaatgtcaa tgagactgca gacttggagc ttccatctgc     720
agagaatgtc aatgacaatg ttgagaatct gcctgccaat gacagttctc ccgaagaaaa     780

```
tgttcttgtt gaggcatgca cggaagtggt tagttcgtgt gcagagaaca ttcctgcagc    840
tgcacctgca cctgctcctc gtgcctcgac tcagaaggat gttactaaac agtcatatgc    900
atcagttgtt aaggttacaa aggagggcac accaactcca cctgttgcaa agcccaagcc    960
caaacccaaa ccaaagccaa ctgcaaaagt gactgacaat gtggagaaag ctgtgtcctc   1020
acctgtgaaa cctactaatg cagctgatac acatctcca aatgacaaaa atgttcttgt    1080
tgagcaaggg tattctgttt atgtaaagca cttaccttat gaatgtacca cgaaagatgt   1140
tgaggaaaag ttcaggaaat tggtgctat caggcctggt ggtattcaag ttcgacaccg    1200
tcagcccgat ggattctgct ttggctttgt tgaatttgag tctcggcaat ccatgctagc   1260
agcaattgag gcctctccag tttctattgg ctcaaaagca tccattgttg aggagaaacg   1320
aactacaact cgagttgtta atggtgtcac ccatattgaa acaatggca atgctcgggg    1380
tggtcggttc cagcaagaca acagaggtgg tggataccgt ggggacaact tcaggggacg   1440
agaagcaggt ttcgtgaaca atggtaacta ccgtgatggt gataacatga ggaacggatt   1500
cagaaatcag aacgagtact cagggcgtgg tcgtgggcct caggggaatg gttaccatca   1560
gaatggtaac ggtggtggtt accatcagaa tggaaatgga taccatcaga acggtgatgg   1620
ataccatcag aatgggaaca gatacaatca gaacgggaac agataccatc agaacggaga   1680
tgagtactat cagaacggca atggcaatgg acatcggcag aatgggtctg gatactatca   1740
tcagaatggg aatggctatc gtcaggaccg catcttccac aatgggaatg gaaatgggcg   1800
gcctgctcgc ttcaatggac ccaggcaaac accggttcaa gcgtaggcgt ttcttgaata   1860
tccaaaaaat ccttttgtca atcctaggat cgccttattt atctgtgttc ttttgcaccc   1920
cattcggctg cgacaaagtt cagtcccagc ccttcgtttt gcctcgatgc ttttgctgac   1980
tagttggcat gttctggatg tacttggtga ccaggaag tgtaattttg gaaaggttgg     2040
gagcttactg caaggttcgt gacttcatgt cgagacatgc tatctaatat atgcattagt   2100
atttatggca cgcagatgga tgaaggatct gttgtgtgct tttccttatg                2150
```

<210> SEQ ID NO 10
<211> LENGTH: 569
<212> TYPE: PRT
<213> ORGANISM: Oryza sativa

<400> SEQUENCE: 10

```
Met Ala Met Gln Val Gly Glu Ser Val Ala Pro Leu Ser Pro Gln Met
1               5                   10                  15

Ile Gly Asn Ala Phe Val Gln Gln Tyr Tyr Asn Val Leu His Ser Ser
            20                  25                  30

Pro Gly Gln Val Cys Lys Phe Tyr His Asp Ser Ser Thr Leu Gly Arg
        35                  40                  45

Pro Asp Ser Asn Gly Thr Met Thr Ser Val Thr Thr Leu Thr Ala Ile
    50                  55                  60

Asn Asp Glu Phe Leu Ser Thr Asp Phe Ser Ser Cys Leu Ile Lys Leu
65                  70                  75                  80

Glu Asn Val Asp Ala Gln Leu Ser Leu Asn Gly Gly Val His Ile Leu
                85                  90                  95

Val Thr Gly Ser Ile Gly His Asn Gly Thr Met Arg His Arg Phe Ser
            100                 105                 110

Gln Ser Phe Phe Leu Ala Pro Gln Glu Ser Gly Gly Tyr Phe Val Leu
        115                 120                 125

Asn Asp Met Leu Arg Tyr Asp Ser Leu Gln Glu Thr Leu Leu Thr Glu
    130                 135                 140
```

```
Thr Asn Asp Ser Pro Gln Glu Arg Leu Leu Thr Glu Ile Asn Asp Ser
145                 150                 155                 160

Leu Pro Asn His Val Asp Asp Asn Thr His Ser Val Thr Phe Thr Ser
            165                 170                 175

Glu Pro Glu Thr Ser Gly Asn Val Asn Glu Thr Ala Asp Leu Glu Leu
            180                 185                 190

Pro Ser Ala Glu Asn Val Asn Asp Asn Val Glu Asn Leu Pro Ala Asn
        195                 200                 205

Asp Ser Ser Pro Glu Glu Asn Val Leu Val Glu Ala Cys Thr Glu Val
    210                 215                 220

Val Ser Ser Cys Ala Glu Asn Ile Pro Ala Ala Pro Ala Pro Ala
225                 230                 235                 240

Pro Arg Ala Ser Thr Gln Lys Asp Val Thr Lys Gln Ser Tyr Ala Ser
            245                 250                 255

Val Val Lys Val Thr Lys Glu Gly Thr Pro Thr Pro Val Ala Lys
            260                 265                 270

Pro Lys Pro Lys Pro Lys Pro Thr Ala Lys Val Thr Asp Asn
    275                 280                 285

Val Glu Lys Ala Val Ser Ser Pro Val Lys Pro Thr Asn Ala Ala Asp
    290                 295                 300

Thr Thr Ser Pro Asn Asp Lys Asn Val Leu Val Glu Gln Gly Tyr Ser
305                 310                 315                 320

Val Tyr Val Lys His Leu Pro Tyr Glu Cys Thr Thr Lys Asp Val Glu
                325                 330                 335

Glu Lys Phe Arg Lys Phe Gly Ala Ile Arg Pro Gly Gly Ile Gln Val
                340                 345                 350

Arg His Arg Gln Pro Asp Gly Phe Cys Phe Gly Phe Val Glu Phe Glu
    355                 360                 365

Ser Arg Gln Ser Met Leu Ala Ala Ile Glu Ala Ser Pro Val Ser Ile
    370                 375                 380

Gly Ser Lys Ala Ser Ile Val Glu Glu Lys Arg Thr Thr Arg Val
385                 390                 395                 400

Val Asn Gly Val Thr His Ile Glu Asn Asn Gly Asn Ala Arg Gly Gly
                405                 410                 415

Arg Phe Gln Gln Asp Asn Arg Gly Gly Gly Tyr Arg Gly Asp Asn Phe
            420                 425                 430

Arg Gly Arg Glu Ala Gly Phe Val Asn Asn Gly Asn Tyr Arg Asp Gly
            435                 440                 445

Asp Asn Met Arg Asn Gly Phe Arg Asn Gln Asn Glu Tyr Ser Gly Arg
    450                 455                 460

Gly Arg Gly Pro Gln Gly Asn Gly Tyr His Gln Asn Gly Asn Gly Gly
465                 470                 475                 480

Gly Tyr His Gln Asn Gly Asn Gly Tyr His Gln Asn Gly Asp Gly Tyr
            485                 490                 495

His Gln Asn Gly Asn Arg Tyr Asn Gln Asn Gly Asn Arg Tyr His Gln
                500                 505                 510

Asn Gly Asp Glu Tyr Tyr Gln Asn Gly Asn Gly Asn Gly His Arg Gln
            515                 520                 525

Asn Gly Ser Gly Tyr Tyr His Gln Asn Gly Asn Gly Tyr Arg Gln Asp
        530                 535                 540

Arg Ile Phe His Asn Gly Asn Gly Asn Gly Arg Pro Ala Arg Phe Asn
545                 550                 555                 560

Gly Pro Arg Gln Thr Pro Val Gln Ala
```

565

```
<210> SEQ ID NO 11
<211> LENGTH: 569
<212> TYPE: PRT
<213> ORGANISM: Oryza sativa

<400> SEQUENCE: 11
```

| Met | Ala | Met | Gln | Val | Gly | Glu | Ser | Val | Ala | Pro | Leu | Ser | Pro | Gln | Thr |
|---|---|---|---|---|---|---|---|---|---|---|---|---|---|---|---|
| 1 | | | | 5 | | | | | 10 | | | | | 15 | |

| Ile | Gly | Asn | Ala | Phe | Val | Gln | Gln | Tyr | Tyr | Asn | Val | Leu | His | Ser | Ser |
|---|---|---|---|---|---|---|---|---|---|---|---|---|---|---|---|
| | | | 20 | | | | | 25 | | | | | 30 | | |

| Pro | Gly | Gln | Val | Cys | Lys | Phe | Tyr | His | Asp | Ser | Ser | Thr | Leu | Gly | Arg |
|---|---|---|---|---|---|---|---|---|---|---|---|---|---|---|---|
| | | 35 | | | | | 40 | | | | | 45 | | | |

| Pro | Asp | Ser | Asn | Gly | Thr | Met | Thr | Ser | Val | Thr | Leu | Thr | Ala | Ile |
|---|---|---|---|---|---|---|---|---|---|---|---|---|---|---|
| | 50 | | | | | 55 | | | | | 60 | | | |

Pro Asp Ser Asn Gly Thr Met Thr Ser Val Thr Leu Thr Ala Ile
          50                      55                      60

Asn Asp Glu Phe Leu Ser Thr Asp Phe Ser Ser Cys Leu Ile Lys Leu
65                  70                  75                  80

Glu Asn Val Asp Ala Gln Leu Ser Leu Asn Gly Gly Val His Ile Leu
                85                  90                  95

Val Thr Gly Ser Ile Gly His Asn Gly Thr Met Arg His Arg Phe Ser
            100                 105                 110

Gln Ser Phe Phe Leu Ala Pro Gln Glu Ser Gly Gly Tyr Phe Val Leu
        115                 120                 125

Asn Asp Met Leu Arg Tyr Asp Ser Leu Gln Glu Thr Leu Leu Thr Glu
130                 135                 140

Thr Asn Asp Ser Pro Gln Glu Arg Leu Leu Thr Glu Ile Asn Asp Ser
145                 150                 155                 160

Leu Pro Asn His Val Asp Asp Asn Thr His Ser Val Thr Phe Thr Ser
                165                 170                 175

Glu Pro Glu Thr Ser Gly Asn Val Asn Glu Thr Ala Asp Leu Glu Leu
            180                 185                 190

Pro Ser Ala Glu Asn Val Asn Asp Asn Val Glu Asn Leu Pro Ala Asn
        195                 200                 205

Asp Ser Ser Pro Glu Glu Asn Val Leu Val Glu Ala Cys Thr Glu Val
210                 215                 220

Val Ser Ser Cys Ala Glu Asn Ile Pro Ala Ala Pro Ala Pro Ala
225                 230                 235                 240

Pro Arg Ala Ser Thr Gln Lys Asp Val Thr Lys Gln Ser Tyr Ala Ser
                245                 250                 255

Val Val Lys Val Thr Lys Glu Gly Thr Pro Thr Pro Val Ala Lys
            260                 265                 270

Pro Lys Pro Lys Pro Lys Pro Lys Pro Thr Ala Lys Val Thr Asp Asn
        275                 280                 285

Val Glu Lys Ala Val Ser Ser Pro Val Lys Pro Thr Asn Ala Ala Asp
        290                 295                 300

Thr Thr Ser Pro Asn Asp Lys Asn Val Leu Val Glu Gln Gly Tyr Ser
305                 310                 315                 320

Val Tyr Val Lys His Leu Pro Tyr Glu Cys Thr Ala Lys Asp Val Glu
                325                 330                 335

Glu Lys Phe Arg Lys Phe Gly Ala Ile Arg Pro Gly Gly Ile Gln Val
            340                 345                 350

Arg His Arg Gln Pro Asp Gly Phe Cys Phe Gly Phe Val Glu Phe Glu
        355                 360                 365

Ser Arg Gln Ser Met Leu Ala Ala Ile Glu Ala Ser Pro Val Ser Ile

```
                370             375             380
Gly Ser Lys Ala Ser Ile Val Glu Glu Lys Arg Thr Thr Thr Arg Val
385                 390                 395                 400

Val Asn Gly Val Thr His Ile Glu Asn Gly Asn Ala Trp Gly Gly
                405                 410                 415

Arg Phe Gln Gln Asp Asn Arg Gly Gly Gly Tyr Arg Gly Asp Asn Phe
                420                 425                 430

Arg Gly Arg Glu Ala Gly Phe Val Asn Asn Gly Asn Tyr Arg Asp Gly
                435                 440                 445

Asp Asn Leu Arg Asn Arg Phe Arg Asn Gln Asn Glu Tyr Ser Gly Arg
            450                 455                 460

Gly Arg Gly Pro Gln Gly Asn Gly Tyr His Gln Asn Gly Asn Gly Gly
465                 470                 475                 480

Gly Tyr His Gln Asn Gly Asn Gly Tyr His Gln Asn Gly Asp Gly Tyr
                485                 490                 495

His Gln Asn Gly Asn Arg Tyr Asn Gln Asn Gly Asn Arg Tyr His Gln
                500                 505                 510

Asn Gly Asp Glu Tyr Tyr Gln Asn Gly Asn Gly Asn Gly His Arg Gln
                515                 520                 525

Asn Gly Ser Gly Tyr Tyr His Gln Asn Gly Asn Gly Tyr Arg Gln Asp
            530                 535                 540

Arg Ile Phe His Asn Gly Asn Gly Asn Gly Arg Pro Ala Arg Phe Asn
545                 550                 555                 560

Gly Pro Arg Gln Thr Pro Val Gln Ala
                565
```

```
<210> SEQ ID NO 12
<211> LENGTH: 1562
<212> TYPE: DNA
<213> ORGANISM: Arabidopsis thaliana

<400> SEQUENCE: 12
caccttcctt ctctccttca ctctaattgc gattgattct cctgtcttct ccaatttatc    60
agagaaattg cagagatgac acctgaatca aacgctccct cagtagatcc acaatttgta   120
ggcaatgggt tgttcaaga atactataac cacctttatg attcaacctc ggaagtacac    180
aaattctatc tcgaggatag tatgatttca cggcctggtc tcgatggtga atagttact    240
atcaaatcct tgaaagggat taatgatcag ataatgtcca ttgactacaa agctcaagg    300
atcgagattc taactgctga ttctcaatca actttaaaga atggtgttgt aactctagtc    360
acgggtttag tgatcgggaa cgatggagga aggaggaaat tttctcagag tttctttctt    420
gtgtcgcgga atgaagcta ctttgtgctg aatgataccct ttaggtatgt gtctgatgag    480
tttgttgaac agaagctac caaggaggtt gaggagagtc agtcaacaaa tgctatcact    540
gagcctgcaa atgaaagtgt agaggcggtt attgtcccta ctgaagctaa aactacggtg    600
acgaagccag caagtgccat accaaacgga catgcgaaag tccctgagga gaaagttgtg    660
aatgaaaaca gtagcttacc taagctgctg aagcaaaaac ttcaagagga ggttcccaag    720
aaatcgtttg cattaattgt tcaatctctg gctcaaagcg ctggtacttt acaggttaaa    780
gcctcgccgg tcaagcgtaa acctgtcgaa aaaccggttg ctgctccgga gcgcaaagct    840
ccttccccaa ttcgtaaaca ggcttctgct gaaagcatta accacaagc tcagggtagt    900
tccatatttg ttgcaaactt gcctatggat gcgactattg agcaacttta tgaaacattt    960
aaaagttttg gagctattag aaaggatggt atccaagtca gaagttaccc ggaaaaaaag   1020
```

```
aactgtattg ggtttgtggc attcgaaaat ggtgaagcag taaaaaatgt ctttcaggct   1080
cacagggaat caccaatcag aatcggaaac cgaagagcat ctatagaaga aaagcgagga   1140
ggtaacaatc aaaatggcaa cagagtctct acaagaaaca acagtggtta taaaaatgag   1200
gatggtttca gacgtgatgg atacaaacct aggggcagtg gcgtcaatgg aggacgaggc   1260
tatgggagac ggaacagtga gtctaatggg gatggtaaag cataccagaa caatggccat   1320
ggcaatactg aggccaaaaa ctagattagt ttttcttct tctaagcttt gctcatggtt    1380
gagaatctga ggttgtaggc gatgttaaaa caaattttg tttccgtgga tatcttaggt    1440
gttgatcttt tcgatttgtg atattgtttg gggataaatc tagaacattt ttcttcactc   1500
tttgatctct gtatcttctc atgaacaaag cagagaacaa aatcgaattg atttaaggtt   1560
ct                                                                 1562

<210> SEQ ID NO 13
<211> LENGTH: 422
<212> TYPE: PRT
<213> ORGANISM: Arabidopsis thaliana

<400> SEQUENCE: 13

Met Thr Pro Glu Ser Asn Ala Pro Ser Val Asp Pro Gln Phe Val Gly
1               5                   10                  15

Asn Gly Phe Val Gln Glu Tyr Tyr Asn His Leu Tyr Asp Ser Thr Ser
            20                  25                  30

Glu Val His Lys Phe Tyr Leu Glu Asp Ser Met Ile Ser Arg Pro Gly
        35                  40                  45

Leu Asp Gly Glu Ile Val Thr Ile Lys Ser Leu Lys Gly Ile Asn Asp
    50                  55                  60

Gln Ile Met Ser Ile Asp Tyr Lys Ser Ser Arg Ile Glu Ile Leu Thr
65                  70                  75                  80

Ala Asp Ser Gln Ser Thr Leu Lys Asn Gly Val Val Thr Leu Val Thr
                85                  90                  95

Gly Leu Val Ile Gly Asn Asp Gly Gly Arg Arg Lys Phe Ser Gln Ser
            100                 105                 110

Phe Phe Leu Val Ser Arg Asn Gly Ser Tyr Phe Val Leu Asn Asp Thr
        115                 120                 125

Phe Arg Tyr Val Ser Asp Glu Phe Val Glu Pro Glu Ala Thr Lys Glu
    130                 135                 140

Val Glu Glu Ser Gln Ser Thr Asn Ala Ile Thr Glu Pro Ala Asn Glu
145                 150                 155                 160

Ser Val Glu Ala Val Ile Val Pro Thr Glu Ala Lys Thr Thr Val Thr
                165                 170                 175

Lys Pro Ala Ser Ala Ile Pro Asn Gly His Ala Lys Val Pro Glu Glu
            180                 185                 190

Lys Val Val Asn Glu Asn Ser Ser Leu Pro Lys Ala Ala Glu Ala Lys
        195                 200                 205

Leu Gln Glu Glu Val Pro Lys Lys Ser Phe Ala Leu Ile Val Gln Ser
    210                 215                 220

Leu Ala Gln Ser Ala Gly Thr Leu Gln Val Lys Ala Ser Pro Val Lys
225                 230                 235                 240

Arg Lys Pro Val Glu Lys Pro Val Ala Ala Pro Glu Arg Lys Ala Pro
                245                 250                 255

Ser Pro Ile Arg Lys Gln Ala Ser Ala Glu Ser Ile Lys Pro Gln Ala
            260                 265                 270

Gln Gly Ser Ser Ile Phe Val Ala Asn Leu Pro Met Asp Ala Thr Ile
```

```
                275                 280                 285
Glu Gln Leu Tyr Glu Thr Phe Lys Ser Phe Gly Ala Ile Arg Lys Asp
        290                 295                 300
Gly Ile Gln Val Arg Ser Tyr Pro Glu Lys Lys Asn Cys Ile Gly Phe
305                 310                 315                 320
Val Ala Phe Glu Asn Gly Glu Ala Val Lys Asn Val Phe Gln Ala His
                325                 330                 335
Arg Glu Ser Pro Ile Arg Ile Gly Asn Arg Ala Ser Ile Glu Glu
                340                 345                 350
Lys Arg Gly Gly Asn Asn Gln Asn Gly Asn Arg Val Ser Thr Arg Asn
        355                 360                 365
Asn Ser Gly Tyr Lys Asn Glu Asp Gly Phe Arg Arg Asp Gly Tyr Lys
        370                 375                 380
Pro Arg Gly Ser Gly Val Asn Gly Gly Arg Gly Tyr Gly Arg Arg Asn
385                 390                 395                 400
Ser Glu Ser Asn Gly Asp Gly Lys Ala Tyr Gln Asn Asn Gly His Gly
                405                 410                 415
Asn Thr Glu Ala Lys Asn
            420

<210> SEQ ID NO 14
<211> LENGTH: 1831
<212> TYPE: DNA
<213> ORGANISM: Arabidopsis thaliana

<400> SEQUENCE: 14 ttttttttctt cttcttccat ttttttgttc tcacgtcgct ctctcttttt ttcgagattc    60
agctgtaaaa ccctaactag cgccatagcc aaggaagctt tcctcagatc gtctctccga   120
aattttccgg ttaatcgtca gttaagggga aaattaggct atggcgatgt taggtgcaca   180
gcaagttcca gcagcagctt gtactccaga tatggttggg aatgcttttg tgccccagta   240
ttatcacata ttgcatcaat cacctgagca tgttcacaga ttttaccaag agattagcaa   300
gttaggtcgt cctgaagaga atggtttaat gagcatcact tctaccttgc aagctattga   360
caagaagata atggcgcttg gttacggtgt aatcagtgca gagatagcta ctgtggacac   420
acaagaatct catggaggtg gttatattgt actggtgact gggtatttga cgggaaaaga   480
cagtgtcagg aggacgttta gtcagacctt cttccttgct ccacaggaga caggatactt   540
tgtcttgaat gatatgtttc gattcattga tgaaggcact gtcgtacatg gaaatcagat   600
tccagtgaac aacgtccaag ctcctgtcaa cacttaccag gacacagctg ctgcgaagga   660
aattccagat gactttgttc aggagaaata tgtccaagag aatcatgctg ttaagcaaac   720
cgaggtgttg tccaagagca ttaatgagcc tgaaaaagtg ttcacgccct ctgaagatga   780
acaagtatca gctgcagaag aagctctggt gactgaaaca gttaatgaag caccaattga   840
agtgcaaaag gttggagaat ctgattctag gactggcgaa attccaaaga gatcttatgc   900
atcaattgtg aaggttatga agaaaaatgc tgcaccaatg tctgcttcga gaactccaac   960
aaaggtggaa ccaaagaaac aagaagatca agccattcat atccctctac caacaccatt  1020
gtctgagaaa tcagattcag gagcaaatgt tgctgtaaat gagaacaatc aagagaatga  1080
aagagctcta ggtccatcca tctatctaaa gggtttaccc cttgatgcaa cacctgcctt  1140
gcttgagaat gagttccaga aatttggact tattaggacc aatggaattc aagtgagaag  1200
ccagaaggga ttctgttttg gttttgttga gtttgaatcc gcaagttcca tgcaaagcgc  1260
tatcgaggca tcacctgtca tgctcaatgg acacaaagtt gttgtggagg aaaagcgatc  1320
```

```
taccgcaaga gggaactata gaggacgttc gacgtttggt gtaaacacag gctacagaaa    1380
cgaaggagga aggggtcgtg ggagctttgg aggtggaaga ggaggatatg gccggaccga    1440
tttcaacgga tatggtaata acaggggaaa caatagaggc ggatacgcaa accgagcaaa    1500
tggtgatggt ggtgggttcc cgagggccaa tggtaacaat ggacgagtaa gacgtggtgg    1560
cggaaatgat gctaacagag ctacgaaacc cgtggatgat gctccccgtg tgtctgttgc    1620
tgcgtaaatg tgcttttgaa acaaaaagct ctattggttt tagagagttt aggcgtagag    1680
caatggcaaa aaaaaacact attattttct tttcactgtg tcgccatttt attaattgga    1740
gtcaaaactt gagagcaaga gagagtttcg tcggttcttg cttgtctatt ttttcttcac    1800
tgctaatgaa atctctttct tcatgtggct c    1831
```

<210> SEQ ID NO 15
<211> LENGTH: 488
<212> TYPE: PRT
<213> ORGANISM: Arabidopsis thaliana

<400> SEQUENCE: 15

```
Met Ala Met Leu Gly Ala Gln Gln Val Pro Ala Ala Cys Thr Pro
1               5                   10                  15

Asp Met Val Gly Asn Ala Phe Val Pro Gln Tyr Tyr His Ile Leu His
            20                  25                  30

Gln Ser Pro Glu His Val His Arg Phe Tyr Gln Glu Ile Ser Lys Leu
        35                  40                  45

Gly Arg Pro Glu Glu Asn Gly Leu Met Ser Ile Thr Ser Thr Leu Gln
    50                  55                  60

Ala Ile Asp Lys Lys Ile Met Ala Leu Gly Tyr Gly Val Ile Ser Ala
65                  70                  75                  80

Glu Ile Ala Thr Val Asp Thr Gln Glu Ser His Gly Gly Gly Tyr Ile
                85                  90                  95

Val Leu Val Thr Gly Tyr Leu Thr Gly Lys Asp Ser Val Arg Arg Thr
            100                 105                 110

Phe Ser Gln Thr Phe Phe Leu Ala Pro Gln Glu Thr Gly Tyr Phe Val
        115                 120                 125

Leu Asn Asp Met Phe Arg Phe Ile Asp Glu Gly Thr Val Val His Gly
    130                 135                 140

Asn Gln Ile Pro Val Asn Asn Val Gln Ala Pro Val Asn Thr Tyr Gln
145                 150                 155                 160

Asp Thr Ala Ala Ala Lys Glu Ile Pro Asp Phe Val Gln Glu Lys
                165                 170                 175

Tyr Val Gln Glu Asn His Ala Val Lys Gln Thr Glu Val Leu Ser Lys
            180                 185                 190

Ser Ile Asn Glu Pro Glu Lys Val Phe Thr Pro Ser Glu Asp Glu Gln
        195                 200                 205

Val Ser Ala Ala Glu Glu Ala Leu Val Thr Glu Thr Val Asn Glu Ala
    210                 215                 220

Pro Ile Glu Val Gln Lys Val Gly Glu Ser Asp Ser Arg Thr Gly Glu
225                 230                 235                 240

Ile Pro Lys Arg Ser Tyr Ala Ser Ile Val Lys Val Met Lys Glu Asn
                245                 250                 255

Ala Ala Pro Met Ser Ala Ser Arg Thr Pro Thr Lys Val Glu Pro Lys
            260                 265                 270

Lys Gln Glu Asp Gln Ala Ile His Ile Pro Leu Pro Thr Pro Leu Ser
        275                 280                 285
```

```
Glu Lys Ser Asp Ser Gly Ala Asn Val Ala Val Asn Glu Asn Gln
    290                 295                 300
Glu Asn Glu Arg Ala Leu Gly Pro Ser Ile Tyr Leu Lys Gly Leu Pro
305                 310                 315                 320
Leu Asp Ala Thr Pro Ala Leu Leu Glu Asn Glu Phe Gln Lys Phe Gly
                325                 330                 335
Leu Ile Arg Thr Asn Gly Ile Gln Val Arg Ser Gln Lys Gly Phe Cys
            340                 345                 350
Phe Gly Phe Val Glu Phe Glu Ser Ala Ser Ser Met Gln Ser Ala Ile
        355                 360                 365
Glu Ala Ser Pro Val Met Leu Asn Gly His Lys Val Val Glu Glu
    370                 375                 380
Lys Arg Ser Thr Ala Arg Gly Asn Tyr Arg Gly Arg Ser Thr Phe Gly
385                 390                 395                 400
Val Asn Thr Gly Tyr Arg Asn Glu Gly Arg Gly Arg Gly Ser Phe
                405                 410                 415
Gly Gly Gly Arg Gly Gly Tyr Gly Arg Thr Asp Phe Asn Gly Tyr Gly
            420                 425                 430
Asn Asn Arg Gly Asn Asn Arg Gly Gly Tyr Ala Asn Arg Ala Asn Gly
        435                 440                 445
Asp Gly Gly Gly Phe Pro Arg Ala Asn Gly Asn Asn Gly Arg Val Arg
    450                 455                 460
Arg Gly Gly Gly Asn Asp Ala Asn Arg Ala Thr Lys Pro Val Asp Asp
465                 470                 475                 480
Ala Pro Arg Val Ser Val Ala Ala
                485

<210> SEQ ID NO 16
<211> LENGTH: 1897
<212> TYPE: DNA
<213> ORGANISM: Oryza sativa

<400> SEQUENCE: 16
gagcgagaga ggagacaaac ccctctccac ctccccccaa aaccctaacc cttcctcctc      60
ccaccttccc gccacgccac catggcctcg ccccgccgc cgccgccctc cgccgccgcc     120 cccgatcgc cgccgtcggc gcaagtggtg gggaacgcgt tcgtgcacca gtactacaac     180
atcctgcacc agtcgccgga tctcgtccac cgcttctacc aggacgggag ccgcatcggc     240
cgccccgcct ccccgccgc cgccgagatg gacaccgtca ccaccatgga ggcgattaac     300
gcgaagatcg tgtccatgga catcgtgcgg gcggagatca aggcggtgga cgcgcaggag     360
tcgctgggcg gggcgtcac ggtgctcgtc acgggccacc tcaccgggag cgacgacgtg     420
cgcagggagt tctcgcagtc cttcttcctc gcgccgcagg agaagggata cttcgtgctc     480
aacgacatcc tgcgctacgt cggggggggag gggatcagg aggtgagcc ggagccggag     540 ctggagctgt cgtttccgcc gtcgcagcag ccggattcgg tgcctgctcc ttcggcgaat     600
ggcactagcg tgccgcggga acaggaggcc ttctcgcagc cggagcagca tgtggctgat     660
cctgcaccca atgctcagga ggctgatctc aacggcgagg aggtttataa cccaccgaac     720
aacacagagg ggcctgttgt ggaggaaacg ccgattcctg aagttataga tgaagtgcca     780
aataacgtag ctgtggctat gccgactccg cctgcccctg ccctgcccc tgtaccacaa     840 gaggaggccc ccaagaagtc gtatgcttca attgtcaaag tcatgaaaga aattccacca     900
caaatatctg caattccttc caggccggca ccaccaaaac aagagaagca agttgctcct     960
```

| | | |
|---|---|---|
| gcacctgttg ctccggttgc tgatgctcca actttcagtc ctaatcctga aagcagcaac | 1020 | |
| attcaagagg ctgaagttga tgcacatgcg atatatgtac ggaatctgcc tttaagtgcc | 1080 | |
| acgcctgaac aattagaaga agcattcaag aaatttggcg ctatcaagcc ggacggaatc | 1140 | |
| caagttagaa gtcacaagat tcaagggttc tgctatgggt tgtagagtt tgaagatccc | 1200 | |
| agttcagttc aaagtgcaat tgcgggttct cctgtgacga ttagtgaccg caatgttat | 1260 | |
| gtggaggaaa agaaactgc tggttcacgt ggtggtggca gaggaaggtt tgctcctggt | 1320 | |
| agaggtggta acttccgagg tgaaggcatg agaggccgcg ggaattacac cggagggagg | 1380 | |
| ggctatggaa ggggtgagtt caattatcga tccgactatg gaggcagagg cgctggtaga | 1440 | |
| ggtggttcat cacgtggtgg tgatgttggc taccagcggg ttgaccactc tgctggtcgt | 1500 | |
| gctgctcggg cgccatcggg cactagtgcc gttgcaaagt gagcgagtta gttgctatgc | 1560 | |
| ctcggttgct atgcgtcggt gaaaaagttt gatattttcg tgggttggaa ttatcaacat | 1620 | |
| tcgggaagag ggtatgtgtt gagttgggtt tatgtgagag attatcagca aaaatcgggt | 1680 | |
| cataaattga agcttccctt gttttgtggc aagggagagc agtggtgata ttggtttact | 1740 | |
| aattgtagca atacgtcta ttcagaattc cagatgtagt cctggtaagc ttggcccttt | 1800 | |
| ttggagtacc tgatgtttgt ttttcccct cttttgtcc ctcttttcta gcaggatcga | 1860 | |
| ttctattacg aatgagaggt gatgagttat agattcc | 1897 | |

<210> SEQ ID NO 17
<211> LENGTH: 486
<212> TYPE: PRT
<213> ORGANISM: Oryza sativa

<400> SEQUENCE: 17

Met Ala Ser Pro Pro Pro Pro Pro Ser Ala Ala Pro Gly Ser
1               5                   10                  15

Pro Pro Ser Ala Gln Val Val Gly Asn Ala Phe Val His Gln Tyr Tyr
            20                  25                  30

Asn Ile Leu His Gln Ser Pro Asp Leu Val His Arg Phe Tyr Gln Asp
        35                  40                  45

Gly Ser Arg Ile Gly Arg Pro Ala Ser Pro Ala Ala Ala Glu Met Asp
    50                  55                  60

Thr Val Thr Thr Met Glu Ala Ile Asn Ala Lys Ile Val Ser Met Asp
65                  70                  75                  80

Ile Val Arg Ala Glu Ile Lys Ala Val Asp Ala Gln Glu Ser Leu Gly
                85                  90                  95

Gly Gly Val Thr Val Leu Val Thr Gly His Leu Thr Gly Ser Asp Asp
            100                 105                 110

Val Arg Arg Glu Phe Ser Gln Ser Phe Phe Leu Ala Pro Gln Glu Lys
        115                 120                 125

Gly Tyr Phe Val Leu Asn Asp Ile Leu Arg Tyr Val Gly Gly Glu Gly
    130                 135                 140

Asp Gln Glu Val Glu Pro Glu Pro Leu Glu Leu Ser Phe Pro Pro
145                 150                 155                 160

Ser Gln Gln Pro Asp Ser Val Pro Ala Pro Ser Ala Asn Gly Thr Ser
                165                 170                 175

Val Pro Arg Glu Gln Glu Ala Phe Ser Gln Pro Glu Gln His Val Ala
            180                 185                 190

Asp Pro Ala Pro Asn Ala Gln Glu Ala Asp Leu Asn Gly Glu Glu Val
        195                 200                 205

Tyr Asn Pro Pro Asn Asn Thr Glu Gly Pro Val Val Glu Glu Thr Pro

```
          210                 215                 220
Ile Pro Glu Val Ile Asp Glu Val Pro Asn Asn Val Ala Val Ala Met
225                 230                 235                 240

Pro Thr Pro Pro Ala Pro Ala Pro Ala Pro Val Pro Gln Glu Glu Ala
                245                 250                 255

Pro Lys Lys Ser Tyr Ala Ser Ile Val Lys Val Met Lys Glu Ile Pro
                260                 265                 270

Pro Gln Ile Ser Ala Ile Pro Ser Arg Pro Ala Pro Lys Gln Glu
            275                 280                 285

Lys Gln Val Ala Pro Ala Pro Val Ala Pro Val Ala Asp Ala Pro Thr
290                 295                 300

Phe Ser Pro Asn Pro Glu Ser Ser Asn Ile Gln Glu Ala Glu Val Asp
305                 310                 315                 320

Ala His Ala Ile Tyr Val Arg Asn Leu Pro Leu Ser Ala Thr Pro Glu
                325                 330                 335

Gln Leu Glu Glu Ala Phe Lys Lys Phe Gly Ala Ile Lys Pro Asp Gly
                340                 345                 350

Ile Gln Val Arg Ser His Lys Ile Gln Gly Phe Cys Tyr Gly Phe Val
            355                 360                 365

Glu Phe Glu Asp Pro Ser Ser Val Gln Ser Ala Ile Ala Gly Ser Pro
370                 375                 380

Val Thr Ile Ser Asp Arg Gln Cys Tyr Val Glu Lys Arg Thr Ala
385                 390                 395                 400

Gly Ser Arg Gly Gly Arg Gly Arg Phe Ala Pro Gly Arg Gly Gly
                405                 410                 415

Asn Phe Arg Gly Glu Gly Met Arg Gly Arg Gly Asn Tyr Thr Gly Gly
                420                 425                 430

Arg Gly Tyr Gly Arg Gly Glu Phe Asn Tyr Arg Ser Asp Tyr Gly Gly
            435                 440                 445

Arg Gly Ala Gly Arg Gly Ser Ser Arg Gly Gly Asp Val Gly Tyr
                450                 455                 460

Gln Arg Val Asp His Ser Ala Gly Arg Ala Ala Arg Ala Pro Ser Gly
465                 470                 475                 480

Thr Ser Ala Val Ala Lys
                485

<210> SEQ ID NO 18
<211> LENGTH: 1659
<212> TYPE: DNA
<213> ORGANISM: Trifolium pratense

<400> SEQUENCE: 18
ggcacgaggt tctctttctc tctttgatct ctccatcaca ccaaggagag atggcagtat      60
ctgatggagt ccaaacccca acccctcagg tggttggcaa tgcttttgtc gagcagtatt     120
actcaattct tcaccaagac ccggatcagg ttcataagtt ttaccacgaa tcaagtgtct     180
tgagtcgacc tgaagaagac ggtaccatga caactgtcac taccactgct gaaattgata     240
aaaagataca atcttttgat tacacaagct atagggtaga ggttctgagt gctgatgctc     300
agccttcata taatagtggg gttgtggttg tagtgactgg ctgcttgacc ggaactgaca     360
atgttaaacg caaatttgct cagtcctttt tcctagctcc acaggacaag gcttctatg      420 ttttgaatga tgttttaga tatgttgatg cgtataagtc tgttgatatt gagactgtac     480
cagcaaatga tgctgatgaa agtgctccat cagaagcttt tactccagat cctgagccta     540
ttcatgttgc tgaagacatt ccaaccattc aacctgttat tgctgatact gacactaaca     600
```

```
tcagcaaaga agtgagctta ccactggaga atggaaaatt atcagttact gaaaatgtga    660
ttcctgttaa tcatgttaaa gagtcaagtc atcaggaaca aatggcaagc attgagaaag    720
ttccttcaaa tacacaggag gatactccca aaaaatcttt tgcatccatt gtgagtgcct    780
ataaagataa ttctgctccc ttcctttcga ggacttctcc tgcaaaaccc gctgtgcaac    840
caccccgtgt acatagcgtg cctgctcctg aagcaccagc ccctaacatg gacattccat    900
cggaaaagaa taatgagaat ggaggtaggg ctcatgcaat atttgttgcg aatttgccta    960
tgactgcaac agtagagcaa ttggaccggg ttttcaagaa attcgggacc attaaacgtg   1020
atggtattca agttagaagt aacaagggat cttgctttgg ttttgtggaa tttgaatctg   1080
ctgcttcact gcaaagtgcc ctagaggcct cccctcctgt tatgttggac aaccgtaggc   1140
tttccattga agaaaggcga ggacgtggtg ataccgaaa tgacagaaat gataacttca    1200
ggggccgtgg caactttggt ggcggccgtg gtggtggctt taacggaagg aatgattttg   1260
acaggcgagg cgagttctct ggccggccta gaggaggcaa taataccggt cgaagcaatg   1320
gagatgctgc gccaaggagt tatcagaatg gaggaggaaa agtcgctcgt caaccgccag   1380
tgaaggctca gtaaagtgct tcttttttgtc ggtaattgag tggcaacgag atttctcttag  1440 tagatagagg gaggcattag ggattttggt ttgaatttga attagagtct tttgctttgt   1500 agttctgtg atatttttc gtcagagttc tttggttaaa tcaggttttc tccatactga   1560
cttctttttt cttaatctct tccaattttg tttcctactg tatctaattt ttctggtatg   1620
attgttttgg aattggccag ttatatatca tttttgttt                         1659

<210> SEQ ID NO 19
<211> LENGTH: 447
<212> TYPE: PRT
<213> ORGANISM: Trifolium pratense

<400> SEQUENCE: 19

Met Ala Val Ser Asp Gly Val Gln Thr Pro Thr Pro Gln Val Val Gly
1               5                   10                  15

Asn Ala Phe Val Glu Gln Tyr Tyr Ser Ile Leu His Gln Asp Pro Asp
            20                  25                  30

Gln Val His Lys Phe Tyr His Glu Ser Ser Val Leu Ser Arg Pro Glu
        35                  40                  45

Glu Asp Gly Thr Met Thr Thr Val Thr Thr Thr Ala Glu Ile Asp Lys
    50                  55                  60

Lys Ile Gln Ser Phe Asp Tyr Thr Ser Tyr Arg Val Glu Val Leu Ser
65                  70                  75                  80

Ala Asp Ala Gln Pro Ser Tyr Asn Ser Gly Val Val Val Val Val Thr
                85                  90                  95

Gly Cys Leu Thr Gly Thr Asp Asn Val Lys Arg Lys Phe Ala Gln Ser
            100                 105                 110

Phe Phe Leu Ala Pro Gln Asp Lys Gly Phe Tyr Val Leu Asn Asp Val
        115                 120                 125

Phe Arg Tyr Val Asp Ala Tyr Lys Ser Val Asp Ile Glu Thr Val Pro
    130                 135                 140

Ala Asn Asp Ala Asp Glu Ser Ala Pro Ser Glu Ala Phe Thr Pro Asp
145                 150                 155                 160

Pro Glu Pro Ile His Val Ala Glu Asp Ile Pro Thr Ile Gln Pro Val
                165                 170                 175

Ile Ala Asp Thr Asp Thr Asn Ile Ser Lys Glu Val Ser Leu Pro Leu
            180                 185                 190
```

```
Glu Asn Gly Lys Leu Ser Val Thr Glu Asn Val Ile Pro Val Asn His
            195                 200                 205

Val Lys Glu Ser Ser His Gln Glu Gln Met Ala Ser Ile Glu Lys Val
        210                 215                 220

Pro Ser Asn Thr Gln Glu Asp Thr Pro Lys Lys Ser Phe Ala Ser Ile
225                 230                 235                 240

Val Ser Ala Tyr Lys Asp Asn Ser Ala Pro Phe Leu Ser Arg Thr Ser
                245                 250                 255

Pro Ala Lys Pro Ala Val Gln Pro Pro Arg Val His Ser Val Pro Ala
            260                 265                 270

Pro Glu Ala Pro Ala Pro Asn Met Asp Ile Pro Ser Glu Lys Asn Asn
        275                 280                 285

Glu Asn Gly Gly Arg Ala His Ala Ile Phe Val Ala Asn Leu Pro Met
    290                 295                 300

Thr Ala Thr Val Glu Gln Leu Asp Arg Val Phe Lys Lys Phe Gly Thr
305                 310                 315                 320

Ile Lys Arg Asp Gly Ile Gln Val Arg Ser Asn Lys Gly Ser Cys Phe
                325                 330                 335

Gly Phe Val Glu Phe Glu Ser Ala Ala Ser Leu Gln Ser Ala Leu Glu
            340                 345                 350

Ala Ser Pro Pro Val Met Leu Asp Asn Arg Arg Leu Ser Ile Glu Glu
        355                 360                 365

Arg Arg Gly Arg Gly Gly Tyr Arg Asn Asp Arg Asn Asp Asn Phe Arg
    370                 375                 380

Gly Arg Gly Asn Phe Gly Gly Arg Gly Gly Phe Asn Gly Arg
385                 390                 395                 400

Asn Asp Phe Asp Arg Arg Gly Glu Phe Ser Gly Arg Pro Arg Gly Gly
                405                 410                 415

Asn Asn Thr Gly Arg Ser Asn Gly Asp Ala Ala Pro Arg Ser Tyr Gln
            420                 425                 430

Asn Gly Gly Gly Lys Val Ala Arg Gln Pro Pro Val Lys Ala Gln
        435                 440                 445

<210> SEQ ID NO 20
<211> LENGTH: 1745
<212> TYPE: DNA
<213> ORGANISM: Arabidopsis thaliana

<400> SEQUENCE: 20
acggttcctt ctcttctctc tctctctttc tccgtctgtc gctgtctctc tcgtcctctc      60
ctctgtttcg tagcttctgc agcagatctc tctttgtcct tctctctccc tcagatcact     120
atggcacagc aggaagctag tccttcccct ggtgctgagg ttgttggtcg tgcctttgtg     180
gagcaatact atcatattct tcaccaatct cccggtttag ttcatcggtt ttatcaagat     240
tcgagctttt taacccgacc tgatgttacc ggtgctgtga ctactgtcac aactatgcaa     300
gcgatcaacg acaagattct gtcgttgaaa tatgaagact acacggctga gatagaaact     360
gctgatgctc aggagtctca tgagagaggt gttattgtgc tggttacagg acgcttaacc     420
gggaacgata atgttaggaa gaagtttagt caatcttttt tcttggctcc acaagacaaa     480
ggatactttg tcttaaacga cgtgtttcga ttccttgagg agaaagaggt gactgcacaa     540
gcccgctctg tccccatcaa tggaaccact agggatgttc aggctcctat tgaaccagaa     600
cgtgttgttg ttagtcacga gcccgaggta gaacccgagc cagttgcttc tatcgaggaa     660
gaagatcttg acaatgtggc ggaagtgtat gatccttctg ataaagatga aggagttgtt     720
```

```
gttgacgttg agcctattga acctcccact caaataagtc ataatgaaat cttatcagtg    780
cctcaaggag atgctcctaa gcattcttat gcttcaatcc tcaagcagat gaaaagcagt    840
ccagcaccaa caacacacgt tgctagaaac aagccaagac cagctccagt caaccagaag    900
ctgaccgcgc tcctgctga gcctgcagca agacccgagg cttcagctca tgagaatgtt    960
ccgaatagta gccatgttga tgtggaagat gatggtcatt cgatttatgt tcgaaatttg   1020
ccgtttgact ccacaccaac acaacttgaa gaggtgttca agaactttgg tgcaatcaag   1080
catgagggga ttcaagtcag aagcaacaag cagcaaggtt tctgttttgg ttttgtggaa   1140
tttgaaacat ctagcggaaa gcaaagtgcc ctcgaggcct caccagttac aattggagat   1200
cgtcaagctg ttgtagagga gaagaaaaca aatagtcgag gaggaggcaa caatggaggt   1260
agcaggggaa ggtactttc cggaagagga agtttccgaa atgaaagctt caaggagga    1320 cgcggtggtg ggggaagagg aggctatgga agaggaggag gtgagttttc tggtagacca   1380
aagagctcaa acccacgaaa tggaggagaa ggttaccaaa gggttcctca aaacggagga   1440
ggtggaagag gaggccgcgg agaaggaggt cgtggtggag ctcgaggtgg tggttcatct   1500
tgactttgct tttaacgctc ctctacaaga gagtagtttt aatttttgtt ttgcgtcttt   1560
ctttttgcct actacttgag ttgatgtggt attggctttt ttgtcggtct agttttcaa   1620 tattcttgct ttttttcctc tctttttgt tttcatctt tcaatctttc tttggggtaa   1680
tgtactcttc ataaacaaac attcaatttc ataaggaatc cattatagag ttgtgttctt   1740
tacgc                                                              1745

<210> SEQ ID NO 21
<211> LENGTH: 460
<212> TYPE: PRT
<213> ORGANISM: Arabidopsis thaliana

<400> SEQUENCE: 21

Met Ala Gln Gln Glu Ala Ser Pro Ser Pro Gly Ala Glu Val Val Gly
1               5                   10                  15

Arg Ala Phe Val Glu Gln Tyr Tyr His Ile Leu His Gln Ser Pro Gly
            20                  25                  30

Leu Val His Arg Phe Tyr Gln Asp Ser Ser Phe Leu Thr Arg Pro Asp
        35                  40                  45

Val Thr Gly Ala Val Thr Thr Val Thr Thr Met Gln Ala Ile Asn Asp
    50                  55                  60

Lys Ile Leu Ser Leu Lys Tyr Glu Asp Tyr Thr Ala Glu Ile Glu Thr
65                  70                  75                  80

Ala Asp Ala Gln Glu Ser His Glu Arg Gly Val Ile Val Leu Val Thr
                85                  90                  95

Gly Arg Leu Thr Gly Asn Asp Asn Val Arg Lys Lys Phe Ser Gln Ser
            100                 105                 110

Phe Phe Leu Ala Pro Gln Asp Lys Gly Tyr Phe Val Leu Asn Asp Val
        115                 120                 125

Phe Arg Phe Leu Glu Glu Lys Glu Val Thr Ala Gln Ala Arg Ser Val
    130                 135                 140

Pro Ile Asn Gly Thr Thr Arg Asp Val Gln Ala Pro Ile Glu Pro Glu
145                 150                 155                 160

Arg Val Val Val Ser His Glu Pro Glu Val Glu Pro Glu Pro Val Ala
                165                 170                 175

Ser Ile Glu Glu Glu Asp Leu Asp Asn Val Ala Glu Val Tyr Asp Pro
            180                 185                 190
```

Ser Asp Lys Asp Glu Gly Val Val Asp Val Glu Pro Ile Glu Pro
        195                 200                 205

Pro Thr Gln Ile Ser His Asn Glu Ile Leu Ser Val Pro Gln Gly Asp
    210                 215                 220

Ala Pro Lys His Ser Tyr Ala Ser Ile Leu Lys Gln Met Lys Ser Ser
225                 230                 235                 240

Pro Ala Pro Thr Thr His Val Ala Arg Asn Lys Pro Arg Pro Ala Pro
                245                 250                 255

Val Asn Gln Lys Leu Thr Ala Pro Pro Ala Glu Pro Ala Ala Arg Pro
            260                 265                 270

Glu Ala Ser Ala His Glu Asn Val Pro Asn Ser Ser His Val Asp Val
        275                 280                 285

Glu Asp Asp Gly His Ser Ile Tyr Val Arg Asn Leu Pro Phe Asp Ser
    290                 295                 300

Thr Pro Thr Gln Leu Glu Glu Val Phe Lys Asn Phe Gly Ala Ile Lys
305                 310                 315                 320

His Glu Gly Ile Gln Val Arg Ser Asn Lys Gln Gln Gly Phe Cys Phe
                325                 330                 335

Gly Phe Val Glu Phe Glu Thr Ser Ser Gly Lys Gln Ser Ala Leu Glu
            340                 345                 350

Ala Ser Pro Val Thr Ile Gly Asp Arg Gln Ala Val Glu Glu Lys
        355                 360                 365

Lys Thr Asn Ser Arg Gly Gly Asn Asn Gly Gly Ser Arg Gly Arg
    370                 375                 380

Tyr Phe Ser Gly Arg Gly Ser Phe Arg Asn Glu Ser Phe Lys Gly Gly
385                 390                 395                 400

Arg Gly Gly Gly Arg Gly Gly Tyr Gly Arg Gly Gly Glu Phe
                405                 410                 415

Ser Gly Arg Pro Lys Ser Ser Asn Pro Arg Asn Gly Gly Glu Gly Tyr
            420                 425                 430

Gln Arg Val Pro Gln Asn Gly Gly Gly Arg Gly Gly Arg Gly Glu
        435                 440                 445

Gly Gly Arg Gly Gly Ala Arg Gly Gly Gly Ser Ser
    450                 455                 460

<210> SEQ ID NO 22
<211> LENGTH: 1338
<212> TYPE: DNA
<213> ORGANISM: Macaca mulatta

<400> SEQUENCE: 22
atggtgatgg agaagcctag tccoctgctg gtcgggcggg aatttgtgag acaatattac      60
acactgctga accaggcccc agacatgctg catagatttt atggaaagaa ctcttcttat     120
gtccatgggg gattggattc aaatggaaag ccagcagatg cagtctacgg acagaaagaa     180
atccacagga aagtgatgtc acaaaatttc accaactgcc acaccaagat tcgccatgtt     240
gatgctcatg ccacgctaaa tgatggtgtg gtagtccagg tgatgggct tctctctaac     300 aacaaccagg ctttgaggag attcatgcaa acgtttgtcc ttgctcctga ggggtctgtt     360
gcaaataaat tctatgttca caatgatatc ttcagatacc aagatgaggt ctttggtggg     420
tttgtcactg agcctcagga ggaatctgaa gaagaagtag aggaacctga gaaagacag      480 caaacacctg aggtggtacc tgatgattct ggaactttct atgatcaggc agttgtcagt     540
aatgacatgg aagaacattt agaggagcct gttgctgaac cagagcctga tcctgaacca     600

```
gaaccagaac aagaacctgt atctgaaatc caagaggaaa agcctgagcc agtattagaa    660
gaaactgctc ctgaggatac tcagaagagt tcttctccag cacctgcaga catagctcag    720
acagtacagg aagacttgag gacgttttct tgggcatctg tgaccagtaa gaaccttcca    780
cccagtggga ctgttccagt tactgggata ccacctcatg ttgttaaagt accagcttca    840
cagccccgtc cagagtctaa gcctgaatct cagattccac cacagagacc agtccgtgag    900
gctggtgagc aaggtgacat tgaaccccga gaatggtga  cacccctga cagtcaccaa    960
ctcttcattg caacctgcc tcatgaagtg acaaatcag  agcttaaaga tttctttcaa   1020
aattatggga acgtggtgga gttgcgcatt aacagtggtg ggaaattacc caattttggt   1080
tttgttgtgt tgatgattc tgagcctgtt cagaaggtcc ttagcaacag gcctatcatg   1140
ttcagaggtg aggtccgtct gaatgtcgaa gagaagaaga ctcgagctgc cagggaaggc   1200
gaccgacgag ataatcgcct tcggggacct ggaggccctc gaggtgggct gggtggtgga   1260
atgagaggcc ctccccgtgg aggcatggtg cagaaaccag gatttggagt gggaaggggg   1320
cttgcgccac ggcagtga                                                 1338
```

<210> SEQ ID NO 23
<211> LENGTH: 445
<212> TYPE: PRT
<213> ORGANISM: Macaca mulatta

<400> SEQUENCE: 23

```
Met Val Met Glu Lys Pro Ser Pro Leu Leu Val Gly Arg Glu Phe Val
1               5                   10                  15

Arg Gln Tyr Tyr Thr Leu Leu Asn Gln Ala Pro Asp Met Leu His Arg
            20                  25                  30

Phe Tyr Gly Lys Asn Ser Ser Tyr Val His Gly Gly Leu Asp Ser Asn
        35                  40                  45

Gly Lys Pro Ala Asp Ala Val Tyr Gly Gln Lys Glu Ile His Arg Lys
    50                  55                  60

Val Met Ser Gln Asn Phe Thr Asn Cys His Thr Lys Ile Arg His Val
65                  70                  75                  80

Asp Ala His Ala Thr Leu Asn Asp Gly Val Val Gln Val Met Gly
                85                  90                  95

Leu Leu Ser Asn Asn Asn Gln Ala Leu Arg Arg Phe Met Gln Thr Phe
            100                 105                 110

Val Leu Ala Pro Glu Gly Ser Val Ala Asn Lys Phe Tyr Val His Asn
        115                 120                 125

Asp Ile Phe Arg Tyr Gln Asp Glu Val Phe Gly Gly Phe Val Thr Glu
    130                 135                 140

Pro Gln Glu Glu Ser Glu Glu Val Glu Glu Pro Glu Glu Arg Gln
145                 150                 155                 160

Gln Thr Pro Glu Val Val Pro Asp Asp Ser Gly Thr Phe Tyr Asp Gln
            165                 170                 175

Ala Val Val Ser Asn Asp Met Glu Glu His Leu Glu Glu Pro Val Ala
        180                 185                 190

Glu Pro Glu Pro Asp Pro Glu Pro Glu Pro Glu Gln Glu Pro Val Ser
    195                 200                 205

Glu Ile Gln Glu Glu Lys Pro Glu Pro Val Leu Glu Glu Thr Ala Pro
    210                 215                 220

Glu Asp Thr Gln Lys Ser Ser Pro Ala Pro Ala Asp Ile Ala Gln
225                 230                 235                 240

Thr Val Gln Glu Asp Leu Arg Thr Phe Ser Trp Ala Ser Val Thr Ser
```

|  |  |  | 245 |  |  | 250 |  |  |  | 255 |  |
|---|---|---|---|---|---|---|---|---|---|---|---|

Lys Asn Leu Pro Pro Ser Gly Ala Val Pro Val Thr Gly Ile Pro Pro
            260                 265                 270

His Val Lys Val Pro Ala Ser Gln Pro Arg Pro Glu Ser Lys Pro
        275                 280                 285

Glu Ser Gln Ile Pro Pro Gln Arg Pro Val Arg Glu Ala Gly Glu Gln
        290                 295                 300

Gly Asp Ile Glu Pro Arg Arg Met Val Arg His Pro Asp Ser His Gln
305                 310                 315                 320

Leu Phe Ile Gly Asn Leu Pro His Glu Val Asp Lys Ser Glu Leu Lys
                325                 330                 335

Asp Phe Phe Gln Asn Tyr Gly Asn Val Val Glu Leu Arg Ile Asn Ser
            340                 345                 350

Gly Gly Lys Leu Pro Asn Phe Gly Phe Val Val Phe Asp Asp Ser Glu
        355                 360                 365

Pro Val Gln Lys Val Leu Ser Asn Arg Pro Ile Met Phe Arg Gly Glu
        370                 375                 380

Val Arg Leu Asn Val Glu Glu Lys Lys Thr Arg Ala Ala Arg Glu Gly
385                 390                 395                 400

Asp Arg Arg Asp Asn Arg Leu Arg Gly Pro Gly Pro Arg Gly Gly
                405                 410                 415

Leu Gly Gly Gly Met Arg Gly Pro Pro Arg Gly Met Val Gln Lys
            420                 425                 430

Pro Gly Phe Gly Val Gly Arg Gly Leu Ala Pro Arg Gln
        435                 440                 445

<210> SEQ ID NO 24
<211> LENGTH: 1377
<212> TYPE: DNA
<213> ORGANISM: Trifolium pratense

<400> SEQUENCE: 24
atggcgtctt cgtatcctgg ttccgttagt gccgctcagg ttggttctta cttcgttgga      60
cagtactatc aagttcttcg tcaacaacct gatcttgttc atcagttta ctctgattcc     120
agttccatga ttcgtgttga tggtgattat tctgagactg catctgatgt gttgcatatt     180
cataatattg tgacatcact gaattttcg acaattgaga tcaagacgat caattctctt     240
gactcttggg atggaggagt gattgtgatg gtcacgggtg ttgttaagat caaggatgtg     300
aacaggaagc agaagtttgt tcagactttc ttccttgccc ctcaggagaa gggttatttt     360
gtgctcaacg atatatttca atttgttcat gaggaagtag tgcatccaaa tctggtaccg     420
gtgacctctg aaaagattga ctcacagcca catgtgtctg cttcttttgc tgagccacca     480
gcttcagact atggttttga ggaagaagca agggaatatg tcaactcagt tcatatagac     540
gatgatccgg tggacaagta tagtcttcct gagcagcatc agcagctaca agaagattc     600
gaatctgaag ttgtggtgga ggaaactcct gcacaggagg catctccaca ggtgtatagt     660
gttgcacaaa ctatccgtga aacccctgtt gctcatgtgg aagagtcgta tgaggagcct     720
gctaagaaaa cttatgcatc tatttttacgt gtcgccaaag ccaatcagt ggtgtccgct     780
gcaccacaac atgctccaca gcattctttt aaaagtgctc ctcctcttc cgattttaat     840
catgtcacac agcctgctgt tcagcagtca gtggtgcagc ctgcgtttca gcagtcaaga     900
tcagcatcta catatgtttc agagtctggg gctgaggcaa cagaagaaag ctacaaattt     960
gaagaagaag aagtaacatc tgtctatgtg agaaacctgc ctggtgatat taccgaagcg    1020

-continued

```
gagattgagg aggagttcaa gagtttcggc agaattaagc cagatggaat atttgaaatt    1080
ggagtttgct atgcatttgt tgaattcgaa gacgttgttg gcgttcaaaa tgcacttcag    1140
gcttctccca tacaattggc tggtagacaa atatacatag aggagcgaag accaagcagc    1200
ggcggtgcag ctcgaggagg aagaggaagg ggaagaggca gaggcggtta tccaacagat    1260
gctccaagag ggcgttttgg tggcaggagc tcgggaaggg gttattatca ggatacctca    1320
gactatacca ggagctcggg aagaggtgat ggttatcttc agcgcggttc acgatag      1377
```

```
<210> SEQ ID NO 25
<211> LENGTH: 458
<212> TYPE: PRT
<213> ORGANISM: Trifolium pratense

<400> SEQUENCE: 25
```

| | | | | | | | | | | | | | | |
|---|---|---|---|---|---|---|---|---|---|---|---|---|---|---|
| Met | Ala | Ser | Ser | Tyr | Pro | Gly | Ser | Val | Ser | Ala | Ala | Gln | Val | Gly | Ser |
| 1 | | | | 5 | | | | | 10 | | | | | 15 | |

Tyr Phe Val Gly Gln Tyr Tyr Gln Val Leu Arg Gln Gln Pro Asp Leu
            20                  25                  30

Val His Gln Phe Tyr Ser Asp Ser Ser Met Ile Arg Val Asp Gly
 35                  40                  45

Asp Tyr Ser Glu Thr Ala Ser Asp Val Leu His Ile His Asn Ile Val
 50                  55                  60

Thr Ser Leu Asn Phe Ser Thr Ile Glu Ile Lys Thr Ile Asn Ser Leu
65                  70                  75                  80

Asp Ser Trp Asp Gly Gly Val Ile Val Met Val Thr Gly Val Val Lys
                85                  90                  95

Ile Lys Asp Val Asn Arg Lys Gln Lys Phe Val Gln Thr Phe Phe Leu
            100                 105                 110

Ala Pro Gln Glu Lys Gly Tyr Phe Val Leu Asn Asp Ile Phe Gln Phe
        115                 120                 125

Val His Glu Glu Val Val His Pro Asn Leu Val Pro Thr Ser Glu
    130                 135                 140

Lys Ile Asp Ser Gln Pro His Val Ser Ala Ser Phe Ala Glu Pro Pro
145                 150                 155                 160

Ala Ser Asp Tyr Gly Phe Glu Glu Ala Arg Glu Tyr Val Asn Ser
                165                 170                 175

Val His Ile Asp Asp Pro Val Asp Lys Tyr Ser Leu Pro Glu Gln
            180                 185                 190

His Gln Gln Leu Gln Glu Asp Phe Glu Ser Glu Val Val Val Glu Glu
        195                 200                 205

Thr Pro Ala Gln Glu Ala Ser Pro Gln Val Tyr Ser Val Ala Gln Thr
    210                 215                 220

Ile Arg Glu Thr Pro Val Ala His Val Glu Glu Ser Tyr Glu Glu Pro
225                 230                 235                 240

Ala Lys Lys Thr Tyr Ala Ser Ile Leu Arg Val Ala Lys Gly Gln Ser
                245                 250                 255

Val Val Ser Ala Ala Pro Gln His Ala Pro Gln His Ser Phe Lys Ser
            260                 265                 270

Ala Pro Pro Pro Ser Asp Phe Asn His Val Thr Gln Pro Ala Val Gln
        275                 280                 285

Gln Ser Val Val Gln Pro Ala Phe Gln Gln Ser Arg Ser Ala Ser Thr
    290                 295                 300

Tyr Val Ser Glu Ser Gly Ala Glu Ala Thr Glu Glu Ser Tyr Lys Phe
305                 310                 315                 320

-continued

```
Glu Glu Glu Glu Val Thr Ser Val Tyr Val Arg Asn Leu Pro Gly Asp
            325                 330                 335

Ile Thr Glu Ala Glu Ile Glu Glu Phe Lys Ser Phe Gly Arg Ile
        340                 345                 350

Lys Pro Asp Gly Ile Phe Glu Ile Gly Val Cys Tyr Ala Phe Val Glu
            355                 360                 365

Phe Glu Asp Val Val Gly Val Gln Asn Ala Leu Gln Ala Ser Pro Ile
        370                 375                 380

Gln Leu Ala Gly Arg Gln Ile Tyr Ile Glu Glu Arg Arg Pro Ser Ser
385                 390                 395                 400

Gly Gly Ala Ala Arg Gly Gly Arg Gly Arg Gly Arg Gly Arg Gly Gly
            405                 410                 415

Tyr Pro Thr Asp Ala Pro Arg Gly Arg Phe Gly Gly Arg Ser Ser Gly
            420                 425                 430

Arg Gly Tyr Tyr Gln Asp Thr Ser Asp Tyr Thr Arg Ser Ser Gly Arg
            435                 440                 445

Gly Asp Gly Tyr Leu Gln Arg Gly Ser Arg
            450                 455
```

<210> SEQ ID NO 26
<211> LENGTH: 1380
<212> TYPE: DNA
<213> ORGANISM: Oryza sativa

<400> SEQUENCE: 26

```
atggggggc ggtaccacat ggagatgccc accgggatga gggagctgga ccgcgtgcag      60
cagcagatcg ccagccaccc ctacgccttc gaggtgtgct cctacttctt gcagggtac    120
tacaacgtgc tcgcgaacag cccggagctg gcgtgccaat tctacacgga ttacagcacc    180
gccgtgaggc tggactgcca gacgatgaaa tcctcgttcg gggagactgt tgaggaaatc    240
aatgacatga tcatatccat gaatgtacac aagattgagg ttaagacagc taatttcgtg    300
cagtcatggg gtggggctct ccagatgttg ttactggcc tagtgcaatt aaaggactac    360
cctgttcgca agagatttgc tcagactatg cttcttgctc ctcaggataa tggatattat    420
gtattcagtg acatctttaa gcttatctgt gatgaatatg attactatga aggggctgat    480
tacagtcaca ctgacaacat tctccagatg gatgctcata taccatgac tgaaacagcg    540
tctgattgta tgcctgaaga acttgaggca aaggaagctt tagctcctgc tgatattgag    600
gaaaggggtc ctgctttat gcctgaaaat catgaagttc agcagcaaga tcctttggaa    660
tatgggggtttg tgatcgacga tgattctcct tctgaagagc ttactccttc gttccccagt    720
tctactgaca gtaaacagga tgcacctctt ggccccattg tccatccttc tgtaactacc    780
cctgaggaag agcctatggg agaaccagcc aaacaaacat acgcttcagt gctgcgaaca    840
aaaggacacc ctagccatca ggctattcac tccattcctc tcaacaaggc cacggcaagt    900
agtgtggagt cacaactgaa tggacatatg actaagcagg tgcagcctgt gcatgaaaaa    960
gccaacctgg acacccgtta tgatgctagc ggccctgagg atgaagaaga gttttttgtca   1020
gtttatatcg ggaaccttc tccatctact tcagtctttg atcttgagaa ggtattccag   1080
gcttttggaa gaattaaacc tgacggggtt gctatacgga gccgcaagga ggctggaatt   1140
ttctttggct ttgttgagta cgaagacatg tctggtatcc ataatgcttt gagggcatct   1200
ccaatagagc tgaatggccg cttaatacat gttgaagaga ggaggcaaat ctatcgggga   1260
ggtgagcaa gacggggagag aggaagacct gctgacttct ctaggggtca atcgggtggg   1320
cggtatgatg gggattatgc tactcggtca aagggaaatg ggtaccaaag aagggtttga   1380
```

<210> SEQ ID NO 27
<211> LENGTH: 459
<212> TYPE: PRT
<213> ORGANISM: Oryza sativa

<400> SEQUENCE: 27

Met Gly Gly Arg Tyr His Met Glu Met Pro Thr Gly Met Arg Glu Leu
1               5                   10                  15

Asp Arg Val Gln Gln Gln Ile Ala Ser His Pro Tyr Ala Phe Glu Val
            20                  25                  30

Cys Ser Tyr Phe Leu Gln Gly Tyr Tyr Asn Val Leu Ala Asn Ser Pro
        35                  40                  45

Glu Leu Ala Cys Gln Phe Tyr Thr Asp Tyr Ser Thr Ala Val Arg Leu
    50                  55                  60

Asp Cys Gln Thr Met Lys Ser Ser Phe Gly Glu Thr Val Glu Glu Ile
65                  70                  75                  80

Asn Asp Met Ile Ile Ser Met Asn Val His Lys Ile Glu Val Lys Thr
                85                  90                  95

Ala Asn Phe Val Gln Ser Trp Gly Gly Ala Leu Gln Met Leu Val Thr
            100                 105                 110

Gly Leu Val Gln Leu Lys Asp Tyr Pro Val Arg Lys Arg Phe Ala Gln
        115                 120                 125

Thr Met Leu Leu Ala Pro Gln Asp Asn Gly Tyr Tyr Val Phe Ser Asp
    130                 135                 140

Ile Phe Lys Leu Ile Cys Asp Glu Tyr Asp Tyr Tyr Glu Gly Ala Asp
145                 150                 155                 160

Tyr Ser His Thr Asp Asn Ile Leu Gln Met Asp Ala His Asn Thr Met
                165                 170                 175

Thr Glu Thr Ala Ser Asp Cys Met Pro Glu Glu Leu Glu Ala Lys Glu
            180                 185                 190

Ala Leu Ala Pro Ala Asp Ile Glu Glu Arg Gly Pro Ala Phe Met Pro
        195                 200                 205

Glu Asn His Glu Val Gln Gln Gln Asp Pro Leu Glu Tyr Gly Val Val
    210                 215                 220

Ile Asp Asp Asp Ser Pro Ser Glu Glu Leu Thr Pro Ser Phe Pro Ser
225                 230                 235                 240

Ser Thr Asp Ser Lys Gln Asp Ala Pro Leu Gly Pro Ile Val His Pro
                245                 250                 255

Ser Val Thr Thr Pro Glu Glu Glu Pro Met Gly Glu Pro Ala Lys Gln
            260                 265                 270

Thr Tyr Ala Ser Val Leu Arg Thr Lys Gly His Pro Ser His Gln Ala
        275                 280                 285

Ile His Ser Ile Pro Leu Asn Lys Ala Thr Ala Ser Ser Val Glu Ser
    290                 295                 300

Gln Leu Asn Gly His Met Thr Lys Gln Val Gln Pro Val His Glu Lys
305                 310                 315                 320

Ala Asn Leu Asp Thr Arg Tyr Asp Ala Ser Gly Pro Glu Asp Glu Glu
                325                 330                 335

Glu Phe Leu Ser Val Tyr Ile Gly Asn Leu Ser Pro Ser Thr Ser Val
            340                 345                 350

Phe Asp Leu Glu Lys Val Phe Gln Ala Phe Gly Arg Ile Lys Pro Asp
        355                 360                 365

Gly Val Ala Ile Arg Ser Arg Lys Glu Ala Gly Ile Phe Phe Gly Phe
    370                 375                 380

Val Glu Tyr Glu Asp Met Ser Gly Ile His Asn Ala Leu Arg Ala Ser
385                 390                 395                 400

Pro Ile Glu Leu Asn Gly Arg Leu Ile His Val Glu Glu Arg Arg Gln
            405                 410                 415

Ile Tyr Arg Gly Gly Gly Ala Arg Arg Gly Arg Gly Arg Pro Ala Asp
            420                 425                 430

Phe Ser Arg Gly Gln Ser Gly Gly Arg Tyr Asp Gly Asp Tyr Ala Thr
            435                 440                 445

Arg Ser Lys Gly Asn Gly Tyr Gln Arg Arg Val
    450                 455

<210> SEQ ID NO 28
<211> LENGTH: 1368
<212> TYPE: DNA
<213> ORGANISM: Medicago truncatula

<400> SEQUENCE: 28

| | | |
|---|---|---|
| atggttggca atgcttttgt ggagcagtat tactcaattc tgcaccgcga cccggatcag | 60 |
| gttcataggt tttaccacga ctcaagtgtc atgagtcgac ctgaggagga tggtaccatg | 120 |
| acaactgtca ccaccactgc agaaattgat aaaaagatac aatctctcga gtacacaagc | 180 |
| tttagggtgg aggttctgag tgctgatgct cagccttcat ataataatgg agtgatggtt | 240 |
| gtagtgactg gctgcttgac tggaactgac aatattaaac gcaagtttgc gcagtcattt | 300 |
| ttcctggctc cacaggacaa gggcttctat gttttgaatg atgttttag atatgttgat | 360 |
| gcgtataagt caattgatat cgagtctgtg ccagcaaatg atgctgatga agtgctcca | 420 |
| tcagaagcta ttattacacc cgagcctgag cctgttcatg ttcctgaagt cattccaccc | 480 |
| actcaaactg ttattccaac tgctcaaact gttattccac ccactcaaac tgttattgct | 540 |
| gatactgaaa ctatcatcag taagaagtg agcttgccac tggagaatgg aaaattatca | 600 |
| gttactgaaa atgtgattcc tgttaatcat gttaaagagt caagtcatca tgttaaggaa | 660 |
| ccggaacaac ccacaagcat tgagaaagtt gcttccaata cacaggagga tactccaaaa | 720 |
| aagtcctttg catccattgt gaatgccttg aaagataatt ccgctccctt ccatttgagg | 780 |
| gcttctcctg ctaaaccagc tgtgcaccca ccccgtgtac atagcgtgcc tgctcctgaa | 840 |
| gcaccaaccc ctaacatgga cattccattg gaaaagaata tgagaatgc aggtagggct | 900 |
| catgcaatat tgttgcaaa tttgcctatg agtgcaacag tagagcaatt ggatcgggct | 960 |
| ttcaagaaat tcgggcccat taagcgtgat ggtattcaag tcagaagtaa caggggtct | 1020 |
| tgttttggtt ttgtggagtt tgaatctgct gcttcaatgc aaagtgccct agaggcctct | 1080 |
| cctcctgtta tgttggacaa ccgtagactt tccattgaag aaaggagagg gcgtagtgga | 1140 |
| taccgaaatg acagaaatga taacttcagg ggccgtggca actttggtgg cggccgtggg | 1200 |
| ggtggcttta acgaaggaa cgattttgag aggcgaggag gtgagttctc tggccgatct | 1260 |
| cgaggaggcc agaatgccgg cgaagcaat ggagatgctg tgccaaggag ttatcagaat | 1320 |
| ggaggaggaa aagtcgctgc tcgtcaacca ccagtgaaag ttcaataa | 1368 |

<210> SEQ ID NO 29
<211> LENGTH: 455
<212> TYPE: PRT
<213> ORGANISM: Medicago truncatula

<400> SEQUENCE: 29

Met Val Gly Asn Ala Phe Val Glu Gln Tyr Tyr Ser Ile Leu His Arg
1               5                   10                  15

```
Asp Pro Asp Gln Val His Arg Phe Tyr His Asp Ser Ser Val Met Ser
            20                  25                  30

Arg Pro Glu Glu Asp Gly Thr Met Thr Thr Val Thr Thr Thr Ala Glu
            35                  40                  45

Ile Asp Lys Lys Ile Gln Ser Leu Glu Tyr Thr Ser Phe Arg Val Glu
50                  55                  60

Val Leu Ser Ala Asp Ala Gln Pro Ser Tyr Asn Asn Gly Val Met Val
65                  70                  75                  80

Val Val Thr Gly Cys Leu Thr Gly Thr Asp Asn Ile Lys Arg Lys Phe
                85                  90                  95

Ala Gln Ser Phe Phe Leu Ala Pro Gln Asp Lys Gly Phe Tyr Val Leu
            100                 105                 110

Asn Asp Val Phe Arg Tyr Val Asp Ala Tyr Lys Ser Ile Asp Ile Glu
            115                 120                 125

Ser Val Pro Ala Asn Asp Ala Asp Glu Ser Ala Pro Ser Glu Ala Ile
            130                 135                 140

Ile Thr Pro Glu Pro Glu Pro Val His Val Pro Glu Val Ile Pro Pro
145                 150                 155                 160

Thr Gln Thr Val Ile Pro Thr Ala Gln Thr Val Ile Pro Pro Thr Gln
                165                 170                 175

Thr Val Ile Ala Asp Thr Glu Thr Ile Ile Ser Lys Glu Val Ser Leu
            180                 185                 190

Pro Leu Glu Asn Gly Lys Leu Ser Val Thr Glu Asn Val Ile Pro Val
            195                 200                 205

Asn His Val Lys Glu Ser Ser His Val Lys Glu Pro Glu Gln Pro
210                 215                 220

Thr Ser Ile Glu Lys Val Ala Ser Asn Thr Gln Glu Asp Thr Pro Lys
225                 230                 235                 240

Lys Ser Phe Ala Ser Ile Val Asn Ala Leu Lys Asp Asn Ser Ala Pro
                245                 250                 255

Phe His Leu Arg Ala Ser Pro Ala Lys Pro Ala Val His Pro Pro Arg
            260                 265                 270

Val His Ser Val Pro Ala Pro Glu Ala Pro Thr Pro Asn Met Asp Ile
            275                 280                 285

Pro Leu Glu Lys Asn Asn Glu Asn Ala Gly Arg Ala His Ala Ile Phe
            290                 295                 300

Val Ala Asn Leu Pro Met Ser Ala Thr Val Glu Gln Leu Asp Arg Ala
305                 310                 315                 320

Phe Lys Lys Phe Gly Pro Ile Lys Arg Asp Gly Ile Gln Val Arg Ser
                325                 330                 335

Asn Lys Gly Ser Cys Phe Gly Phe Val Glu Phe Glu Ser Ala Ala Ser
            340                 345                 350

Met Gln Ser Ala Leu Glu Ala Ser Pro Pro Val Met Leu Asp Asn Arg
            355                 360                 365

Arg Leu Ser Ile Glu Glu Arg Gly Arg Ser Gly Tyr Arg Asn Asp
370                 375                 380

Arg Asn Asp Asn Phe Arg Gly Arg Gly Asn Phe Gly Gly Arg Gly
385                 390                 395                 400

Gly Gly Phe Asn Gly Arg Asn Asp Phe Glu Arg Gly Gly Glu Phe
            405                 410                 415

Ser Gly Arg Ser Arg Gly Gly Gln Asn Ala Gly Arg Ser Asn Gly Asp
            420                 425                 430

Ala Val Pro Arg Ser Tyr Gln Asn Gly Gly Gly Lys Val Ala Ala Arg
```

```
                435                 440                 445

Gln Pro Pro Val Lys Val Gln
    450                 455

<210> SEQ ID NO 30
<211> LENGTH: 1401
<212> TYPE: DNA
<213> ORGANISM: Homo sapiens

<400> SEQUENCE: 30
atggtgatgg agaagcctag tcccctgctg gtcgggcggg aatttgtgag acagtattac      60
acactgctga accaggcccc agacatgctg catagatttt atggaaagaa ctcttcttat     120
gtccatgggg gattggattc aaatggaaag ccagcagatg cagtctacgg acagaaagaa     180
atccacagga aagtgatgtc acaaaacttc accaactgcc acaccaagat tcgccatgtt     240
gatgctcatg ccacgctaaa tgatggtgtg gtagtccagg tgatgggct  tctctctaac     300 aacaaccagg ctttgaggag attcatgcaa acgtttgtcc ttgctcctga gggtctgtt      360 gcaaataaat tctatgttca caatgatatc ttcagatacc aagatgaggt ctttggtggg     420
tttgtcactg agcctcagga ggagtctgaa gaagaagtag aggaacctga agaaagacag     480
caaacacctg aggtggtacc tgatgattct ggaactttct atgatcaggc agttgtcagt     540
aatgacatgg aagaacattt agaggagcct gttgctgaac agagagctga tcctgaacca     600
gaaccagaac aagaacctgt atctgaaatc aagaggaaa  agcctgagcc agtattagaa     660
gaaactgccc ctgaggatgc tcagaagagt tcttctccag cacctgcaga catagctcag     720
acagtacagg aagacttgag gacatttctct tgggcatctg tgaccagtaa gaatcttcca     780
cccagtggga ctgttccagt tactgggata ccacctcatg ttgttaaagt accagcttca     840
cagccccgtc cagagtctaa gcctgaatct cagattccac cacaaagacc tcagcgggat     900
caaagagtgc gagaacaacg aataaatatt cctccccaaa ggggacccag accaatccgt     960
gaggctggtg agcaaggtga cattgaaccc cgaagaatgg tgagacaccc tgacagtcac    1020
caactcttca ttggcaacct gcctcatgaa gtggacaaat cagagcttaa agatttcttt    1080
caaagttatg gaaacgtggt ggagttgcgc attaacagtg gtgggaaatt acccaatttt    1140
ggttttgttg tgtttgatga ttctgagcct gttcagaaag tccttagcaa caggcccatc    1200
atgttcagag gtgaggtccg tctgaatgtc gaagagaaga agactcgagc tgccagggaa    1260
ggcgaccgac gagataatcg ccttcgggga cctggaggcc ctcgaggtgg gctgggtggt    1320
ggaatgagag gccctccccg tggaggcatg gtgcagaaac caggatttgg agtgggaagg    1380
gggcttgcgc cacggcagtg a                                             1401

<210> SEQ ID NO 31
<211> LENGTH: 505
<212> TYPE: PRT
<213> ORGANISM: Homo sapiens

<400> SEQUENCE: 31

Met Gln Leu Gln Pro Thr Ser His Cys Ser Phe Met Arg Ala Ser Glu
 1               5                  10                  15

Leu Glu Pro Leu Gly Gln Ala Val Pro Lys Phe Leu Thr Leu Arg Asn
            20                  25                  30

Cys Val Glu Leu Thr Lys Ala Met Val Met Glu Lys Pro Ser Pro Leu
        35                  40                  45

Leu Val Gly Arg Glu Phe Val Arg Gln Tyr Tyr Thr Leu Leu Asn Gln
     50                  55                  60
```

```
Ala Pro Asp Met Leu His Arg Phe Tyr Gly Lys Asn Ser Ser Tyr Val
 65                  70                  75                  80

His Gly Gly Leu Asp Ser Asn Gly Lys Pro Ala Asp Ala Val Tyr Gly
             85                  90                  95

Gln Lys Glu Ile His Arg Lys Val Met Ser Gln Asn Phe Thr Asn Cys
            100                 105                 110

His Thr Lys Ile Arg His Val Asp Ala His Ala Thr Leu Asn Asp Gly
            115                 120                 125

Val Val Val Gln Val Met Gly Leu Leu Ser Asn Asn Gln Ala Leu
130                 135                 140

Arg Arg Phe Met Gln Thr Phe Val Leu Ala Pro Glu Gly Ser Val Ala
145                 150                 155                 160

Asn Lys Phe Tyr Val His Asn Asp Ile Phe Arg Tyr Gln Asp Glu Val
                165                 170                 175

Phe Gly Gly Phe Val Thr Glu Pro Gln Glu Glu Ser Glu Glu Glu Val
                180                 185                 190

Glu Glu Pro Glu Glu Arg Gln Gln Thr Pro Glu Val Val Pro Asp Asp
            195                 200                 205

Ser Gly Thr Phe Tyr Asp Gln Ala Val Val Ser Asn Asp Met Glu Glu
            210                 215                 220

His Leu Glu Glu Pro Val Ala Glu Pro Glu Pro Asp Pro Glu Pro Glu
225                 230                 235                 240

Pro Glu Gln Glu Pro Val Ser Glu Ile Gln Glu Glu Lys Pro Glu Pro
                245                 250                 255

Val Leu Glu Glu Thr Ala Pro Glu Asp Ala Gln Lys Ser Ser Ser Pro
                260                 265                 270

Ala Pro Ala Asp Ile Ala Gln Thr Val Gln Glu Asp Leu Arg Thr Phe
            275                 280                 285

Ser Trp Ala Ser Val Thr Ser Lys Asn Leu Pro Pro Ser Gly Ala Val
            290                 295                 300

Pro Val Thr Gly Ile Pro Pro His Val Lys Val Pro Ala Ser Gln
305                 310                 315                 320

Pro Arg Pro Glu Ser Lys Pro Glu Ser Gln Ile Pro Pro Gln Arg Pro
                325                 330                 335

Gln Arg Asp Gln Arg Val Arg Glu Gln Arg Ile Asn Ile Pro Pro Gln
            340                 345                 350

Arg Gly Pro Arg Pro Ile Arg Glu Ala Gly Glu Gln Gly Asp Ile Glu
            355                 360                 365

Pro Arg Arg Met Val Arg His Pro Asp Ser His Gln Leu Phe Ile Gly
370                 375                 380

Asn Leu Pro His Glu Val Asp Lys Ser Glu Leu Lys Asp Phe Phe Gln
385                 390                 395                 400

Ser Tyr Gly Asn Val Val Glu Leu Arg Ile Asn Ser Gly Gly Lys Leu
                405                 410                 415

Pro Asn Phe Gly Phe Val Val Phe Asp Asp Ser Glu Pro Val Gln Lys
            420                 425                 430

Val Leu Ser Asn Arg Pro Ile Met Phe Arg Gly Glu Val Arg Leu Asn
            435                 440                 445

Val Glu Glu Lys Lys Thr Arg Ala Ala Arg Glu Gly Asp Arg Arg Asp
            450                 455                 460

Asn Arg Leu Arg Gly Pro Gly Pro Arg Gly Gly Leu Gly Gly Gly
465                 470                 475                 480

Met Arg Gly Pro Pro Arg Gly Gly Met Val Gln Lys Pro Gly Phe Gly
```

Val Gly Arg Gly Leu Ala Pro Arg Gln
              500                 505

<210> SEQ ID NO 32
<211> LENGTH: 1230
<212> TYPE: DNA
<213> ORGANISM: Oryza sativa

<400> SEQUENCE: 32

```
atggacaccg tcaccaccat ggaggcgatt aacgcgaaga tcgtgtccat ggacatcgtg    60
cgggcggaga tcaaggcggt ggacgcgcag gagtcgctgg gcgggggcgt cacggtgctc   120
gtcacgggcc acctcaccgg gagcgacgac gtgcgcaggg agttctcgca gtccttcttc   180
ctcgcgccgc aggagaaggg atacttcgtg ctcaacgaca tcctgcgcta cgtcgggggg   240
gagggggatc aggaggtgga gccggagccg agctggagc tgtcgtttcc gccgtcgcag    300
cagccggatt cggtgcctgc tccttcggcg aatggcacta gcgtgccgcg gaacaggag    360
gccttctcgc agccggagca gcatgtggct gatcctgcac ccaatgctca ggaggctgat   420
ctcaacggcg aggaggttta acccaccg aacaacacag aggggcctgt tgtggaggaa     480
acgccgattc ctgaagttat agatgaagtg ccaaataacg tagctgtggc tatgccgact   540
ccgtctgccc tgcccctgcc cctgcccctg taccacaaga ggaggccccc aagaagtcgt   600
atgcttcaat tgccggcacc accaaaacaa gagaagcaag ttgctcctgc acctgttgct   660
ccggttgctg atgctccaac tttcagtcct aatcctgaaa gcagcaacat tcaagaggct   720
gaagttgatg cacatgcgat atatgtacgg aatctgcctt taagtgccac gcctgaacaa   780
ttagaagaag cattcaagaa atttggcgct atcaagccgg acggaatcca agttagaagt   840
cacaagattc aagggttctg ctatgggttt gtagagtttg aagatcccag ttcagttcaa   900
agtgcaattg cggttctcc tgtgacgatt agtgaccggc aatgttatgt ggaggaaaag   960
agaactgctg gttcacgtgg tggtggcaga ggaaggtttg ctcctggtag aggtggtaac  1020
ttccgaggtg aaggcatgag aggccgcggg aattacaccg agggagggg ctatggaagg   1080
ggtgagttca attatcgatc cgactatgga ggcagaggcg ctggtagagg tggttcatca  1140
cgtggtggtg atgttggcta ccagcgggtt gaccactctg ctggtcgtgc tgctcgggcg  1200
ccatcgggca ctagtgccgt tgcaaagtga                                   1230
```

<210> SEQ ID NO 33
<211> LENGTH: 409
<212> TYPE: PRT
<213> ORGANISM: Oryza sativa

<400> SEQUENCE: 33

Met Asp Thr Val Thr Thr Met Glu Ala Ile Asn Ala Lys Ile Val Ser
1               5                  10                  15

Met Asp Ile Val Arg Ala Glu Ile Lys Ala Val Asp Ala Gln Glu Ser
             20                  25                  30

Leu Gly Gly Gly Val Thr Val Leu Val Thr Gly His Leu Thr Gly Ser
         35                  40                  45

Asp Asp Val Arg Arg Glu Phe Ser Gln Ser Phe Phe Leu Ala Pro Gln
     50                  55                  60

Glu Lys Gly Tyr Phe Val Leu Asn Asp Ile Leu Arg Tyr Val Gly Gly
65                  70                  75                  80

Glu Gly Asp Gln Glu Val Glu Pro Glu Pro Glu Leu Glu Leu Ser Phe
                 85                  90                  95

```
Pro Pro Ser Gln Gln Pro Asp Ser Val Pro Ala Pro Ser Ala Asn Gly
            100                 105                 110

Thr Ser Val Pro Arg Glu Gln Glu Ala Phe Ser Gln Pro Glu Gln His
            115                 120                 125

Val Ala Asp Pro Ala Pro Asn Ala Gln Glu Ala Asp Leu Asn Gly Glu
130                 135                 140

Glu Val Tyr Asn Pro Pro Asn Asn Thr Glu Gly Pro Val Val Glu Glu
145                 150                 155                 160

Thr Pro Ile Pro Glu Val Ile Asp Glu Val Pro Asn Asn Val Ala Val
                165                 170                 175

Ala Met Pro Thr Pro Ser Ala Leu Pro Leu Pro Leu Pro Leu Tyr His
            180                 185                 190

Lys Arg Arg Pro Pro Arg Ser Arg Met Leu Gln Leu Pro Ala Pro Pro
            195                 200                 205

Lys Gln Glu Lys Gln Val Ala Pro Ala Pro Val Ala Pro Val Ala Asp
210                 215                 220

Ala Pro Thr Phe Ser Pro Asn Pro Glu Ser Ser Asn Ile Gln Glu Ala
225                 230                 235                 240

Glu Val Asp Ala His Ala Ile Tyr Val Arg Asn Leu Pro Leu Ser Ala
                245                 250                 255

Thr Pro Glu Gln Leu Glu Glu Ala Phe Lys Lys Phe Gly Ala Ile Lys
            260                 265                 270

Pro Asp Gly Ile Gln Val Arg Ser His Lys Ile Gln Gly Phe Cys Tyr
            275                 280                 285

Gly Phe Val Glu Phe Glu Asp Pro Ser Ser Val Gln Ser Ala Ile Ala
            290                 295                 300

Gly Ser Pro Val Thr Ile Ser Asp Arg Gln Cys Tyr Val Glu Glu Lys
305                 310                 315                 320

Arg Thr Ala Gly Ser Arg Gly Gly Arg Gly Arg Phe Ala Pro Gly
                325                 330                 335

Arg Gly Gly Asn Phe Arg Gly Glu Gly Met Arg Gly Arg Gly Asn Tyr
            340                 345                 350

Thr Gly Gly Arg Gly Tyr Gly Arg Gly Glu Phe Asn Tyr Arg Ser Asp
            355                 360                 365

Tyr Gly Gly Arg Gly Ala Gly Arg Gly Gly Ser Ser Arg Gly Gly Asp
            370                 375                 380

Val Gly Tyr Gln Arg Val Asp His Ser Ala Gly Arg Ala Ala Arg Ala
385                 390                 395                 400

Pro Ser Gly Thr Ser Ala Val Ala Lys
            405

<210> SEQ ID NO 34
<211> LENGTH: 5
<212> TYPE: PRT
<213> ORGANISM: Artificial sequence
<220> FEATURE:
<223> OTHER INFORMATION: conserved motif 1

<400> SEQUENCE: 34

Gly Ile Gln Val Arg
1               5

<210> SEQ ID NO 35
<211> LENGTH: 5
<212> TYPE: PRT
<213> ORGANISM: Artificial sequence
<220> FEATURE:
```

```
<223> OTHER INFORMATION: conserved motif 2
<220> FEATURE:
<221> NAME/KEY: VARIANT
<222> LOCATION: (1)..(1)
<223> OTHER INFORMATION: Xaa is Val or Ile
<220> FEATURE:
<221> NAME/KEY: VARIANT
<222> LOCATION: (4)..(4)
<223> OTHER INFORMATION: Xaa is Lys or Arg
<220> FEATURE:
<221> NAME/KEY: VARIANT
<222> LOCATION: (5)..(5)
<223> OTHER INFORMATION: Xaa is Arg or Lys

<400> SEQUENCE: 35

Xaa Glu Glu Xaa Xaa
1               5

<210> SEQ ID NO 36
<211> LENGTH: 8
<212> TYPE: PRT
<213> ORGANISM: Artificial sequence
<220> FEATURE:
<223> OTHER INFORMATION: conserved motif 3
<220> FEATURE:
<221> NAME/KEY: VARIANT
<222> LOCATION: (1)..(1)
<223> OTHER INFORMATION: Xaa is Cys, Phe, or Asn
<220> FEATURE:
<221> NAME/KEY: VARIANT
<222> LOCATION: (2)..(2)
<223> OTHER INFORMATION: Xaa is Phe, Tyr, or Ile
<220> FEATURE:
<221> NAME/KEY: VARIANT
<222> LOCATION: (3)..(3)
<223> OTHER INFORMATION: Xaa is Gly or Ala
<220> FEATURE:
<221> NAME/KEY: VARIANT
<222> LOCATION: (5)..(5)
<223> OTHER INFORMATION: Xaa is Ile or Val
<220> FEATURE:
<221> NAME/KEY: VARIANT
<222> LOCATION: (6)..(6)
<223> OTHER INFORMATION: Xaa is Glu, Ala, or Val
<220> FEATURE:
<221> NAME/KEY: VARIANT
<222> LOCATION: (7)..(7)
<223> OTHER INFORMATION: Xaa is Phe or Tyr
<220> FEATURE:
<221> NAME/KEY: VARIANT
<222> LOCATION: (8)..(8)
<223> OTHER INFORMATION: Xaa is Glu or Asp

<400> SEQUENCE: 36

Xaa Xaa Xaa Phe Xaa Xaa Xaa Xaa
1               5

<210> SEQ ID NO 37
<211> LENGTH: 8
<212> TYPE: PRT
<213> ORGANISM: Artificial sequence
<220> FEATURE:
<223> OTHER INFORMATION: conserved motif 4
<220> FEATURE:
<221> NAME/KEY: VARIANT
<222> LOCATION: (2)..(2)
<223> OTHER INFORMATION: Xaa is Lys, Arg, or Gln
<220> FEATURE:
<221> NAME/KEY: VARIANT
<222> LOCATION: (3)..(3)
<223> OTHER INFORMATION: Xaa is Lys, Ser, Ala, or Asn
<220> FEATURE:
<221> NAME/KEY: VARIANT
<222> LOCATION: (4)..(4)
<223> OTHER INFORMATION: Xaa is Phe or Tyr
<220> FEATURE:
```

```
<221> NAME/KEY: VARIANT
<222> LOCATION: (6)..(6)
<223> OTHER INFORMATION: Xaa is Ala, Leu, Thr, Pro, Arg, or Asn
<220> FEATURE:
<221> NAME/KEY: VARIANT
<222> LOCATION: (7)..(7)
<223> OTHER INFORMATION: Xaa is Ile or Val
<220> FEATURE:
<221> NAME/KEY: VARIANT
<222> LOCATION: (8)..(8)
<223> OTHER INFORMATION: Xaa is Lys, Arg, or Val

<400> SEQUENCE: 37

Phe Xaa Xaa Xaa Gly Xaa Xaa Xaa
1               5

<210> SEQ ID NO 38
<211> LENGTH: 8
<212> TYPE: PRT
<213> ORGANISM: Artificial sequence
<220> FEATURE:
<223> OTHER INFORMATION: conserved motif 5
<220> FEATURE:
<221> NAME/KEY: VARIANT
<222> LOCATION: (1)..(1)
<223> OTHER INFORMATION: Xaa is Ser, Ala, or Gln
<220> FEATURE:
<221> NAME/KEY: VARIANT
<222> LOCATION: (2)..(2)
<223> OTHER INFORMATION: Xaa is Val, Ile, or Leu
<220> FEATURE:
<221> NAME/KEY: VARIANT
<222> LOCATION: (3)..(3)
<223> OTHER INFORMATION: Xaa is Phe or Tyr
<220> FEATURE:
<221> NAME/KEY: VARIANT
<222> LOCATION: (4)..(4)
<223> OTHER INFORMATION: Xaa is Val, Leu, or Ile
<220> FEATURE:
<221> NAME/KEY: VARIANT
<222> LOCATION: (5)..(5)
<223> OTHER INFORMATION: Xaa is Lys, Arg, Ala, or Gly
<220> FEATURE:
<221> NAME/KEY: VARIANT
<222> LOCATION: (6)..(6)
<223> OTHER INFORMATION: Xaa is Ser, His, Asn, or Gly
<220> FEATURE:
<221> NAME/KEY: VARIANT
<222> LOCATION: (8)..(8)
<223> OTHER INFORMATION: Xaa is Pro or Ser

<400> SEQUENCE: 38

Xaa Xaa Xaa Xaa Xaa Xaa Leu Xaa
1               5

<210> SEQ ID NO 39
<211> LENGTH: 10
<212> TYPE: PRT
<213> ORGANISM: Artificial sequence
<220> FEATURE:
<223> OTHER INFORMATION: conserved motif 6
<220> FEATURE:
<221> NAME/KEY: VARIANT
<222> LOCATION: (1)..(1)
<223> OTHER INFORMATION: Xaa is Tyr or Phe
<220> FEATURE:
<221> NAME/KEY: VARIANT
<222> LOCATION: (2)..(2)
<223> OTHER INFORMATION: Xaa is Val, Phe, or Tyr
<220> FEATURE:
<221> NAME/KEY: VARIANT
<222> LOCATION: (4)..(4)
<223> OTHER INFORMATION: Xaa is Leu, Phe, or His
<220> FEATURE:
<221> NAME/KEY: VARIANT
<222> LOCATION: (5)..(5)
```

```
<223> OTHER INFORMATION: Xaa is Asn or Ser
<220> FEATURE:
<221> NAME/KEY: VARIANT
<222> LOCATION: (7)..(7)
<223> OTHER INFORMATION: Xaa is Ile, Met, Val, or Thr
<220> FEATURE:
<221> NAME/KEY: VARIANT
<222> LOCATION: (8)..(8)
<223> OTHER INFORMATION: Xaa is Phe or Leu
<220> FEATURE:
<221> NAME/KEY: VARIANT
<222> LOCATION: (9)..(9)
<223> OTHER INFORMATION: Xaa is Arg, Gln, or Lys
<220> FEATURE:
<221> NAME/KEY: VARIANT
<222> LOCATION: (10)..(10)
<223> OTHER INFORMATION: Xaa is Phe, Tyr, or Leu

<400> SEQUENCE: 39

Xaa Xaa Val Xaa Xaa Asp Xaa Xaa Xaa Xaa
 1               5                  10

<210> SEQ ID NO 40
<211> LENGTH: 9
<212> TYPE: PRT
<213> ORGANISM: Artificial sequence
<220> FEATURE:
<223> OTHER INFORMATION: conserved motif 7
<220> FEATURE:
<221> NAME/KEY: VARIANT
<222> LOCATION: (2)..(2)
<223> OTHER INFORMATION: Xaa is Thr, Ser, Ala, Val, or Met
<220> FEATURE:
<221> NAME/KEY: VARIANT
<222> LOCATION: (4)..(4)
<223> OTHER INFORMATION: Xaa is Ser or Thr
<220> FEATURE:
<221> NAME/KEY: VARIANT
<222> LOCATION: (5)..(5)
<223> OTHER INFORMATION: Xaa is Phe or Met
<220> FEATURE:
<221> NAME/KEY: VARIANT
<222> LOCATION: (6)..(6)
<223> OTHER INFORMATION: Xaa is Phe, Leu, or Val
<220> FEATURE:
<221> NAME/KEY: VARIANT
<222> LOCATION: (8)..(8)
<223> OTHER INFORMATION: Xaa is Ala or Val
<220> FEATURE:
<221> NAME/KEY: VARIANT
<222> LOCATION: (9)..(9)
<223> OTHER INFORMATION: Xaa is Pro or Ser

<400> SEQUENCE: 40

Phe Xaa Gln Xaa Xaa Xaa Leu Xaa Xaa
 1               5

<210> SEQ ID NO 41
<211> LENGTH: 8
<212> TYPE: PRT
<213> ORGANISM: Artificial sequence
<220> FEATURE:
<223> OTHER INFORMATION: conserved motif 8
<220> FEATURE:
<221> NAME/KEY: VARIANT
<222> LOCATION: (1)..(1)
<223> OTHER INFORMATION: Xaa is Gly or Ala
<220> FEATURE:
<221> NAME/KEY: VARIANT
<222> LOCATION: (2)..(2)
<223> OTHER INFORMATION: Xaa is Val, Leu, or Tyr
<220> FEATURE:
<221> NAME/KEY: UNSURE
<222> LOCATION: (3)..(3)
<223> OTHER INFORMATION: Xaa can be any naturally occurring amino acid,
       but preferably one of Leu, His, Thr, Ile, Val, Met, or Gln
```

```
<220> FEATURE:
<221> NAME/KEY: VARIANT
<222> LOCATION: (4)..(4)
<223> OTHER INFORMATION: Xaa is Ile, Val, Thr, or Met
<220> FEATURE:
<221> NAME/KEY: VARIANT
<222> LOCATION: (5)..(5)
<223> OTHER INFORMATION: Xaa is Val, Leu, Met, or Gln
<220> FEATURE:
<221> NAME/KEY: VARIANT
<222> LOCATION: (7)..(7)
<223> OTHER INFORMATION: Xaa is Thr or Met

<400> SEQUENCE: 41

Xaa Xaa Xaa Xaa Xaa Val Xaa Gly
1               5

<210> SEQ ID NO 42
<211> LENGTH: 5
<212> TYPE: PRT
<213> ORGANISM: Artificial sequence
<220> FEATURE:
<223> OTHER INFORMATION: Preferred conserved motif 2
<220> FEATURE:
<221> NAME/KEY: VARIANT
<222> LOCATION: (5)..(5)
<223> OTHER INFORMATION: Xaa is Arg or Lys

<400> SEQUENCE: 42

Val Glu Glu Lys Xaa
1               5

<210> SEQ ID NO 43
<211> LENGTH: 8
<212> TYPE: PRT
<213> ORGANISM: Artificial sequence
<220> FEATURE:
<223> OTHER INFORMATION: Preferred conserved motif 3
<220> FEATURE:
<221> NAME/KEY: VARIANT
<222> LOCATION: (2)..(2)
<223> OTHER INFORMATION: Xaa is Phe or Tyr
<220> FEATURE:
<221> NAME/KEY: VARIANT
<222> LOCATION: (5)..(5)
<223> OTHER INFORMATION: Xaa is Ile or Val

<400> SEQUENCE: 43

Cys Xaa Gly Phe Xaa Glu Phe Glu
1               5

<210> SEQ ID NO 44
<211> LENGTH: 8
<212> TYPE: PRT
<213> ORGANISM: Artificial sequence
<220> FEATURE:
<223> OTHER INFORMATION: Preferred conserved motif 5
<220> FEATURE:
<221> NAME/KEY: VARIANT
<222> LOCATION: (1)..(1)
<223> OTHER INFORMATION: Xaa is Ser or Ala
<220> FEATURE:
<221> NAME/KEY: VARIANT
<222> LOCATION: (2)..(2)
<223> OTHER INFORMATION: Xaa is Val or Ile
<220> FEATURE:
<221> NAME/KEY: VARIANT
<222> LOCATION: (3)..(3)
<223> OTHER INFORMATION: Xaa is Phe or Tyr
<220> FEATURE:
<221> NAME/KEY: VARIANT
<222> LOCATION: (4)..(4)
<223> OTHER INFORMATION: Xaa is Val or Leu
<220> FEATURE:
```

```
<221> NAME/KEY: VARIANT
<222> LOCATION: (5)..(5)
<223> OTHER INFORMATION: Xaa is Lys or Arg
<220> FEATURE:
<221> NAME/KEY: VARIANT
<222> LOCATION: (6)..(6)
<223> OTHER INFORMATION: Xaa is Ser, His, or Asn

<400> SEQUENCE: 44

Xaa Xaa Xaa Xaa Xaa Xaa Leu Pro
1               5

<210> SEQ ID NO 45
<211> LENGTH: 10
<212> TYPE: PRT
<213> ORGANISM: Artificial sequence
<220> FEATURE:
<223> OTHER INFORMATION: Preferred conserved motif 6
<220> FEATURE:
<221> NAME/KEY: VARIANT
<222> LOCATION: (2)..(2)
<223> OTHER INFORMATION: Xaa is Val or Phe
<220> FEATURE:
<221> NAME/KEY: VARIANT
<222> LOCATION: (4)..(4)
<223> OTHER INFORMATION: Xaa is Leu or Phe
<220> FEATURE:
<221> NAME/KEY: VARIANT
<222> LOCATION: (7)..(7)
<223> OTHER INFORMATION: Xaa is Ile, Met, or Val
<220> FEATURE:
<221> NAME/KEY: VARIANT
<222> LOCATION: (8)..(8)
<223> OTHER INFORMATION: Xaa is Phe or Leu
<220> FEATURE:
<221> NAME/KEY: VARIANT
<222> LOCATION: (10)..(10)
<223> OTHER INFORMATION: Xaa is Phe or Tyr

<400> SEQUENCE: 45

Tyr Xaa Val Xaa Asn Asp Xaa Xaa Arg Xaa
1               5                   10

<210> SEQ ID NO 46
<211> LENGTH: 9
<212> TYPE: PRT
<213> ORGANISM: Artificial sequence
<220> FEATURE:
<223> OTHER INFORMATION: Preferred conserved motif 7
<220> FEATURE:
<221> NAME/KEY: VARIANT
<222> LOCATION: (2)..(2)
<223> OTHER INFORMATION: Xaa is Thr, Ser, or Ala
<220> FEATURE:
<221> NAME/KEY: VARIANT
<222> LOCATION: (4)..(4)
<223> OTHER INFORMATION: Xaa is Ser or Thr

<400> SEQUENCE: 46

Phe Xaa Gln Xaa Phe Phe Leu Ala Pro
1               5

<210> SEQ ID NO 47
<211> LENGTH: 8
<212> TYPE: PRT
<213> ORGANISM: Artificial sequence
<220> FEATURE:
<223> OTHER INFORMATION: Preferred conserved motif 8
<220> FEATURE:
<221> NAME/KEY: VARIANT
<222> LOCATION: (2)..(2)
<223> OTHER INFORMATION: Xaa is Val or Tyr
<220> FEATURE:
<221> NAME/KEY: VARIANT
```

```
<222> LOCATION: (3)..(3)
<223> OTHER INFORMATION: Xaa is Leu, His, Thr, Ile, Val, or Met
<220> FEATURE:
<221> NAME/KEY: VARIANT
<222> LOCATION: (4)..(4)
<223> OTHER INFORMATION: Xaa is Ile or Val
<220> FEATURE:
<221> NAME/KEY: VARIANT
<222> LOCATION: (5)..(5)
<223> OTHER INFORMATION: Xaa is Val or Leu

<400> SEQUENCE: 47

Gly Xaa Xaa Xaa Xaa Val Thr Gly
1               5
```

PLANTS HAVING ENHANCED YIELD-RELATED TRAITS AND A METHOD FOR MAKING THE SAME

RELATED APPLICATIONS

This application is a national stage application (under 35 U.S.C. §371) of PCT/EP2008/059764, filed Jul. 25, 2008, which claims benefit of European application 07113355.7, filed Jul. 27, 2007, and U.S. provisional application 60/969,996, filed Sep. 5, 2007.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_14546_00060. The size of the text file is 105 KB, and the text file was created on Jan. 20, 2010.

The present invention relates generally to the field of molecular biology and concerns a method for improving various plant growth characteristics by modulating expression in a plant of a nucleic acid encoding a GSBP-like protein (GSBP: GTPase activating protein SH3 domain Binding Protein). The present invention also concerns plants having modulated expression of a nucleic acid encoding a GSBP-like protein, which plants have improved growth characteristics relative to corresponding wild type plants or other control plants. The invention also provides constructs useful in the methods of the invention.

The ever-increasing world population and the dwindling supply of arable land available for agriculture fuels research towards increasing the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits.

A trait of particular economic interest is increased yield. Yield is normally defined as the measurable produce of economic value from a crop. This may be defined in terms of quantity and/or quality. Yield is directly dependent on several factors, for example, the number and size of the organs, plant architecture (for example, the number of branches), seed production, leaf senescence and more. Root development, nutrient uptake, stress tolerance and early vigour may also be important factors in determining yield. Optimizing the above-mentioned factors may therefore contribute to increasing crop yield.

Seed yield is a particularly important trait, since the seeds of many plants are important for human and animal nutrition. Crops such as corn, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. Seeds contain an embryo (the source of new shoots and roots) and an endosperm (the source of nutrients for embryo growth during germination and during early growth of seedlings). The development of a seed involves many genes, and requires the transfer of metabolites from the roots, leaves and stems into the growing seed. The endosperm, in particular, assimilates the metabolic precursors of carbohydrates, oils and proteins and synthesizes them into storage macromolecules to fill out the grain.

Another important trait for many crops is early vigour. Improving early vigour is an important objective of modern rice breeding programs in both temperate and tropical rice cultivars. Long roots are important for proper soil anchorage in water-seeded rice. Where rice is sown directly into flooded fields, and where plants must emerge rapidly through water, longer shoots are associated with vigour. Where drill-seeding is practiced, longer mesocotyls and coleoptiles are important for good seedling emergence. The ability to engineer early vigour into plants would be of great importance in agriculture. For example, poor early vigor has been a limitation to the introduction of maize (Zea mays L.) hybrids based on Corn Belt germplasm in the European Atlantic.

A further important trait is that of improved abiotic stress tolerance. Abiotic stress is a primary cause of crop loss worldwide, reducing average yields for most major crop plants by more than 50% (Wang et al., Planta (2003) 218: 1-14). Abiotic stresses may be caused by drought, salinity, extremes of temperature, chemical toxicity and oxidative stress. The ability to improve plant tolerance to abiotic stress would be of great economic advantage to farmers worldwide and would allow for the cultivation of crops during adverse conditions and in territories where cultivation of crops may not otherwise be possible.

Crop yield may therefore be increased by optimising one of the above-mentioned factors.

Depending on the end use, the modification of certain yield traits may be favoured over others. For example for applications such as forage or wood production, or bio-fuel resource, an increase in the vegetative parts of a plant may be desirable, and for applications such as flour, starch or oil production, an increase in seed parameters may be particularly desirable. Even amongst the seed parameters, some may be favoured over others, depending on the application. Various mechanisms may contribute to increasing seed yield, whether that is in the form of increased seed size or increased seed number.

One approach to increasing yield (seed yield and/or biomass) in plants may be through modification of the inherent growth mechanisms of a plant, such as the cell cycle or various signalling pathways involved in plant growth or in defense mechanisms.

It has now been found that various growth characteristics may be improved in plants by modulating expression in a plant of a nucleic acid encoding a GSBP-like protein (GSBP: GTPase activating protein SH3 domain Binding Protein) in a plant.

BACKGROUND

Post-transcriptional modification of RNA plays an important role in controlling expression of genes and impacts on developmental processes. This control may occur at various levels or stages, such as, for example, mRNA transport out of the nucleus, splicing, polyadenylation, RNA degradation, among others. The regulation is achieved by RNA-binding proteins which may act directly on the RNA or indirectly through association with other proteins. RNA-binding proteins are characterised by the presence of an RNA-binding domain. Most of the heterogeneous nuclear ribonucleoproteins (hnRNP) have an RNA-binding domain known as "RNA recognition motif" (RRM-domain). Another widespread RNA-binding domain is known as the K homology motif (KH-domain), and is found in proteins involved in transcription, mRNA stability, translational silencing and mRNA localisation. For a discussion of various RNA-binding domains, see Burd and Dreyfuss (Science 265, 615-621, 1994).

RNA-binding domains may be present in combination with other domains, such as zinc fingers, ring finger domains, RS domains or NTF-like domains like the "nuclear transport factor 2" (NTF2) domain. Proteins with an NTF2 domain are known to play a role in trafficking of macromolecules, ions and small molecules between the cytoplasm and nucleus.

Hisashi et al. (JP 2005-185101) disclose over 28000 rice cDNAs of which about 75% was annotated through homology with *Arabidopsis thaliana* sequences. It was postulated that these sequence could be useful to create plants with different characteristics compared to their wild-type equivalents. WO 2004/035798 discloses genes that are upregulated or downregulated in transgenic plants overexpressing E2Fa/DPa and the use of such sequences to alter plant characteristics. Both patent applications disclose a GSBP-like protein, however none of them teaches how to increase seed yield of a plant by preferentially expressing a GSBP-like protein in the root.

SUMMARY

Surprisingly, it has now been found that modulating expression of a nucleic acid encoding a GSBP-like polypeptide gives plants having enhanced yield-related traits, in particular increased yield and/or early vigour, relative to control plants.

According one embodiment, there is provided a method for improving yield related traits of a plant relative to control plants, comprising modulating expression of a nucleic acid encoding a GSBP-like polypeptide in a plant. The improved yield related traits comprised increased biomass, early vigour and/or increased seed yield.

DEFINITIONS

Polypeptide(s)/Protein(s)

The terms "polypeptide" and "protein" are used interchangeably herein and refer to amino acids in a polymeric form of any length, linked together by peptide bonds.

Polynucleotide(s)/Nucleic Acid(s)/Nucleic Acid Sequence(s)/Nucleotide Sequence(s)

The terms "polynucleotide(s)", "nucleic acid sequence(s)", "nucleotide sequence(s)", "nucleic acid(s)", "nucleic acid molecule" are used interchangeably herein and refer to nucleotides, either ribonucleotides or deoxyribonucleotides or a combination of both, in a polymeric unbranched form of any length.

Control Plant(s)

The choice of suitable control plants is a routine part of an experimental setup and may include corresponding wild type plants or corresponding plants without the gene of interest. The control plant is typically of the same plant species or even of the same variety as the plant to be assessed. The control plant may also be a nullizygote of the plant to be assessed. Nullizygotes are individuals missing the transgene by segregation. A "control plant" as used herein refers not only to whole plants, but also to plant parts, including seeds and seed parts.

Homologue(s)

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag•100 epitope, c-myc epitope, FLAG®-epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide; insertions will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds) and Table 1 below).

TABLE 1

Examples of conserved amino acid substitutions

| Residue | Conservative Substitutions |
|---------|---------------------------|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Derivatives

"Derivatives" include peptides, oligopeptides, polypeptides which may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein. Furthermore, "derivatives" also include fusions of the naturally-occurring form of the protein with tagging peptides such as FLAG, HIS6 or thioredoxin (for a review of tagging peptides, see Terpe, Appl. Microbiol. Biotechnol. 60, 523-533, 2003).

Orthologue(s)/Paralogue(s)

Orthologues and paralogues encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

Domain

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

Motif/Consensus Sequence/Signature

The term "motif" or "consensus sequence" or "signature" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Hybridisation

The term "hybridisation" as defined herein is a process wherein substantially homologous complementary nucleotide sequences anneal to each other. The hybridisation process can occur entirely in solution, i.e. both complementary nucleic acids are in solution. The hybridisation process can also occur with one of the complementary nucleic acids immobilised to a matrix such as magnetic beads, Sepharose beads or any other resin. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids.

The term "stringency" refers to the conditions under which a hybridisation takes place. The stringency of hybridisation is influenced by conditions such as temperature, salt concentration, ionic strength and hybridisation buffer composition. Generally, low stringency conditions are selected to be about 30° C. lower than the thermal melting point ($T_m$) for the specific sequence at a defined ionic strength and pH. Medium stringency conditions are when the temperature is 20° C. below $T_m$, and high stringency conditions are when the temperature is 10° C. below $T_m$. High stringency hybridisation conditions are typically used for isolating hybridising sequences that have high sequence similarity to the target nucleic acid sequence. However, nucleic acids may deviate in sequence and still encode a substantially identical polypeptide, due to the degeneracy of the genetic code. Therefore medium stringency hybridisation conditions may sometimes be needed to identify such nucleic acid molecules.

The Tm is the temperature under defined ionic strength and pH, at which 50% of the target sequence hybridises to a perfectly matched probe. The $T_m$ is dependent upon the solution conditions and the base composition and length of the probe. For example, longer sequences hybridise specifically at higher temperatures. The maximum rate of hybridisation is obtained from about 16° C. up to 32° C. below $T_m$. The presence of monovalent cations in the hybridisation solution reduce the electrostatic repulsion between the two nucleic acid strands thereby promoting hybrid formation; this effect is visible for sodium concentrations of up to 0.4M (for higher concentrations, this effect may be ignored). Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the Tm decreases about 1° C. per % base mismatch. The Tm may be calculated using the following equations, depending on the types of hybrids:

1) DNA-DNA hybrids (Meinkoth and Wahl, Anal. Biochem., 138: 267-284, 1984):

$$T_m=81.5° C.+16.6\times\log_{10}[Na^+]^a+0.41\times\%[G/C^b]-500\times[L^c]^{-1}-0.61\times\% \text{ formamide}$$

[a] or for other monovalent cation, but only accurate in the 0.01-0.4 M range.
[b] only accurate for % GC in the 30% to 75% range.
[c] L=length of duplex in base pairs.

2) DNA-RNA or RNA-RNA hybrids:

$$Tm=79.8+18.5(\log_{10}[Na^+]^a)+0.58(\% G/C^b)+11.8(\% G/C^b)^2-820/L^c$$

3) oligo-DNA or oligo-RNA[d] hybrids:
[d] oligo, oligonucleotide; $I_n$=effective length of primer=2×(no. of G/C)+(no. of NT).

For <20 nucleotides: $T_m=2 (I_n)$

For 20-35 nucleotides: $T_m=22+1.46 (I_n)$

Non-specific binding may be controlled using any one of a number of known techniques such as, for example, blocking the membrane with protein containing solutions, additions of heterologous RNA, DNA, and SDS to the hybridisation buffer, and treatment with Rnase. For non-homologous probes, a series of hybridizations may be performed by varying one of (i) progressively lowering the annealing temperature (for example from 68° C. to 42° C.) or (ii) progressively lowering the formamide concentration (for example from 50% to 0%). The skilled artisan is aware of various parameters which may be altered during hybridisation and which will either maintain or change the stringency conditions.

Besides the hybridisation conditions, specificity of hybridisation typically also depends on the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. A positive hybridisation gives a signal that is at least twice of that of the background. Generally, suitable stringent conditions for nucleic acid hybridisation assays or gene amplification detection procedures are as set forth above. More or less stringent conditions may also be selected. The skilled artisan is aware of various parameters which may be altered during washing and which will either maintain or change the stringency conditions.

For example, typical high stringency hybridisation conditions for DNA hybrids longer than 50 nucleotides encompass hybridisation at 65° C. in 1×SSC or at 42° C. in 1×SSC and 50% formamide, followed by washing at 65° C. in 0.3×SSC. Examples of medium stringency hybridisation conditions for DNA hybrids longer than 50 nucleotides encompass hybridisation at 50° C. in 4×SSC or at 40° C. in 6×SSC and 50% formamide, followed by washing at 50° C. in 2×SSC. The length of the hybrid is the anticipated length for the hybridising nucleic acid. When nucleic acids of known sequence are hybridised, the hybrid length may be determined by aligning the sequences and identifying the conserved regions described herein. 1×SSC is 0.15M NaCl and 15 mM sodium citrate; the hybridisation solution and wash solutions may additionally include 5×Denhardt's reagent, 0.5-1.0% SDS, 100 μg/ml denatured, fragmented salmon sperm DNA, 0.5% sodium pyrophosphate.

For the purposes of defining the level of stringency, reference can be made to Sambrook et al. (2001) Molecular Cloning: a laboratory manual, 3rd Edition, Cold Spring Harbor Laboratory Press, CSH, New York or to Current Protocols in Molecular Biology, John Wiley & Sons, N.Y. (1989 and yearly updates).

Splice Variant

The term "splice variant" as used herein encompasses variants of a nucleic acid sequence in which selected introns and/or exons have been excised, replaced, displaced or added, or in which introns have been shortened or lengthened. Such variants will be ones in which the biological activity of the protein is substantially retained; this may be achieved by selectively retaining functional segments of the protein. Such splice variants may be found in nature or may be manmade. Methods for predicting and isolating such splice variants are well known in the art (see for example Foissac and Schiex (2005) BMC Bioinformatics 6: 25).

Allelic Variant

Alleles or allelic variants are alternative forms of a given gene, located at the same chromosomal position. Allelic variants encompass Single Nucleotide Polymorphisms (SNPs), as well as Small Insertion/Deletion Polymorphisms (IN-DELs). The size of INDELs is usually less than 100 bp. SNPs and INDELs form the largest set of sequence variants in naturally occurring polymorphic strains of most organisms.

Gene Shuffling/Directed Evolution

Gene shuffling or directed evolution consists of iterations of DNA shuffling followed by appropriate screening and/or selection to generate variants of nucleic acids or portions thereof encoding proteins having a modified biological activity (Castle et al., (2004) Science 304(5674): 1151-4; U.S. Pat. Nos. 5,811,238 and 6,395,547).

Regulatory Element/Control Sequence/Promoter

The terms "regulatory element", "control sequence" and "promoter" are all used interchangeably herein and are to be taken in a broad context to refer to regulatory nucleic acid sequences capable of effecting expression of the sequences to which they are ligated. The term "promoter" typically refers to a nucleic acid control sequence located upstream from the transcriptional start of a gene and which is involved in recognising and binding of RNA polymerase and other proteins, thereby directing transcription of an operably linked nucleic acid. Encompassed by the aforementioned terms are transcriptional regulatory sequences derived from a classical eukaryotic genomic gene (including the TATA box which is required for accurate transcription initiation, with or without a CCAAT box sequence) and additional regulatory sequences (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative that confers, activates or enhances expression of a nucleic acid molecule in a cell, tissue or organ.

A "plant promoter" comprises regulatory elements, which mediate the expression of a coding sequence segment in plant cells. Accordingly, a plant promoter need not be of plant origin, but may originate from viruses or micro-organisms, for example from viruses which attack plant cells. The "plant promoter" can also originate from a plant cell, e.g. from the plant which is transformed with the nucleic acid sequence to be expressed in the inventive process and described herein. This also applies to other "plant" regulatory signals, such as "plant" terminators. The promoters upstream of the nucleotide sequences useful in the methods of the present invention can be modified by one or more nucleotide substitution(s), insertion(s) and/or deletion(s) without interfering with the functionality or activity of either the promoters, the open reading frame (ORF) or the 3'-regulatory region such as terminators or other 3' regulatory regions which are located away from the ORF. It is furthermore possible that the activity of the promoters is increased by modification of their sequence, or that they are replaced completely by more active promoters, even promoters from heterologous organisms. For expression in plants, the nucleic acid molecule must, as described above, be linked operably to or comprise a suitable promoter which expresses the gene at the right point in time and with the required spatial expression pattern.

For the identification of functionally equivalent promoters, the promoter strength and/or expression pattern of a candidate promoter may be analysed for example by operably linking the promoter to a reporter gene and assaying the expression level and pattern of the reporter gene in various tissues of the plant. Suitable well-known reporter genes include for example beta-glucuronidase or beta-galactosidase. The promoter activity is assayed by measuring the enzymatic activity of the beta-glucuronidase or beta-galactosidase. The promoter strength and/or expression pattern may then be compared to that of a reference promoter (such as the one used in the methods of the present invention). Alternatively, promoter strength may be assayed by quantifying mRNA levels or by comparing mRNA levels of the nucleic acid used in the methods of the present invention, with mRNA levels of housekeeping genes such as 18S rRNA, using methods known in the art, such as Northern blotting with densitometric analysis of autoradiograms, quantitative real-time PCR or RT-PCR (Heid et al., 1996 Genome Methods 6: 986-994). Generally by "weak promoter" is intended a promoter that drives expression of a coding sequence at a low level. By "low level" is intended at levels of about 1/10,000 transcripts to about 1/100,000 transcripts, to about 1/500, 0000 transcripts per cell. Conversely, a "strong promoter" drives expression of a coding sequence at high level, or at about 1/10 transcripts to about 1/100 transcripts to about 1/1000 transcripts per cell.

Operably Linked

The term "operably linked" as used herein refers to a functional linkage between the promoter sequence and the gene of interest, such that the promoter sequence is able to initiate transcription of the gene of interest.

Constitutive Promoter

A "constitutive promoter" refers to a promoter that is transcriptionally active during most, but not necessarily all, phases of growth and development and under most environmental conditions, in at least one cell, tissue or organ. Table 2a below gives examples of constitutive promoters.

TABLE 2a

Examples of constitutive promoters

| Gene Source | Reference |
|---|---|
| Actin | McElroy et al, Plant Cell, 2: 163-171, 1990 |
| HMGP | WO 2004/070039 |
| CAMV 35S | Odell et al, Nature, 313: 810-812, 1985 |
| CaMV 19S | Nilsson et al., Physiol. Plant. 100: 456-462, 1997 |
| GOS2 | de Pater et al, Plant J Nov; 2(6): 837-44, 1992, WO 2004/065596 |
| Ubiquitin | Christensen et al, Plant Mol. Biol. 18: 675-689, 1992 |
| Rice cyclophilin | Buchholz et al, Plant Mol Biol. 25(5): 837-43, 1994 |
| Maize H3 histone | Lepetit et al, Mol. Gen. Genet. 231: 276-285, 1992 |
| Alfalfa H3 histone | Wu et al. Plant Mol. Biol. 11: 641-649, 1988 |
| Actin 2 | An et al, Plant J. 10(1); 107-121, 1996 |
| 34S FMV | Sanger et al., Plant. Mol. Biol., 14, 1990: 433-443 |
| Rubisco small subunit | U.S. Pat. No. 4,962,028 |
| OCS | Leisner (1988) Proc Natl Acad Sci USA 85(5): 2553 |
| SAD1 | Jain et al., Crop Science, 39 (6), 1999: 1696 |
| SAD2 | Jain et al., Crop Science, 39 (6), 1999: 1696 |
| nos | Shaw et al. (1984) Nucleic Acids Res. 12(20): 7831-7846 |
| V-ATPase | WO 01/14572 |
| Super promoter | WO 95/14098 |
| G-box proteins | WO 94/12015 |

Ubiquitous Promoter

A ubiquitous promoter is active in substantially all tissues or cells of an organism.

Developmentally-Regulated Promoter

A developmentally-regulated promoter is active during certain developmental stages or in parts of the plant that undergo developmental changes.

Inducible Promoter

An inducible promoter has induced or increased transcription initiation in response to a chemical (for a review see Gatz 1997, Annu. Rev. Plant Physiol. Plant Mol. Biol., 48:89-108), environmental or physical stimulus, or may be "stress-inducible", i.e. activated when a plant is exposed to various stress conditions, or a "pathogen-inducible" i.e. activated when a plant is exposed to exposure to various pathogens.

Organ-Specific/Tissue-Specific Promoter

An organ-specific or tissue-specific promoter is one that is capable of preferentially initiating transcription in certain organs or tissues, such as the leaves, roots, seed tissue etc. For example, a "root-specific promoter" is a promoter that is transcriptionally active predominantly in plant roots, substantially to the exclusion of any other parts of a plant, whilst still allowing for any leaky expression in these other plant parts. Promoters able to initiate transcription in certain cells only are referred to herein as "cell-specific".

Examples of root-specific promoters are listed in Table 2b below:

TABLE 2b

Examples of root-specific promoters

| Gene Source | Reference |
|---|---|
| RCc3 | Plant Mol Biol. 1995 Jan; 27(2): 237-48 |
| Arabidopsis PHT1 | Kovama et al., 2005; Mudge et al. (2002, Plant J. 31: 341) |
| Medicago phosphate transporter | Xiao et al., 2006 |
| Arabidopsis Pyk10 | Nitz et al. (2001) Plant Sci 161(2): 337-346 |
| root-expressible genes | Tingey et al., EMBO J. 6: 1, 1987. |
| tobacco auxin-inducible gene | Van der Zaal et al., Plant Mol. Biol. 16, 983, 1991. |
| β-tubulin | Oppenheimer, et al., Gene 63: 87, 1988. |
| tobacco root-specific genes | Conkling, et al., Plant Physiol. 93: 1203, 1990. |
| B. napus G1-3b gene | U.S. Pat. No. 5,401,836 |
| SbPRP1 | Suzuki et al., Plant Mol. Biol. 21: 109-119, 1993. |
| LRX1 | Baumberger et al. 2001, Genes & Dev. 15: 1128 |
| BTG-26 Brassica napus | US 20050044585 |
| LeAMT1 (tomato) | Lauter et al. (1996, PNAS 3: 8139) |
| The LeNRT1-1 (tomato) | Lauter et al. (1996, PNAS 3: 8139) |
| class I patatin gene (potato) | Liu et al., Plant Mol. Biol. 153: 386-395, 1991. |
| KDC1 (Daucus carota) | Downey et al. (2000, J. Biol. Chem. 275: 39420) |
| TobRB7 gene | W Song (1997) PhD Thesis, North Carolina State University, Raleigh, NC USA |
| OsRAB5a (rice) | Wang et al. 2002, Plant Sci. 163: 273 |
| ALF5 (Arabidopsis) | Diener et al. (2001, Plant Cell 13: 1625) |
| NRT2; 1Np (N. plumbaginifolia) | Quesada et al. (1997, Plant Mol. Biol. 34: 265) |

A seed-specific promoter is transcriptionally active predominantly in seed tissue, but not necessarily exclusively in seed tissue (in cases of leaky expression). The seed-specific promoter may be active during seed development and/or during germination.

A green tissue-specific promoter as defined herein is a promoter that is transcriptionally active predominantly in green tissue, substantially to the exclusion of any other parts of a plant, whilst still allowing for any leaky expression in these other plant parts.

Another example of a tissue-specific promoter is a meristem-specific promoter, which is transcriptionally active predominantly in meristematic tissue, substantially to the exclusion of any other parts of a plant, whilst still allowing for any leaky expression in these other plant parts.

Terminator

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

Modulation

The term "modulation" means in relation to expression or gene expression, a process in which the expression level is changed by said gene expression in comparison to the control plant, preferably the expression level is increased. The original, unmodulated expression may be of any kind of expression of a structural RNA (rRNA, tRNA) or mRNA with subsequent translation. The term "modulating the activity" shall mean any change of the expression of the inventive nucleic acid sequences or encoded proteins, which leads to increased yield and/or increased growth of the plants.

Expression

The term "expression" or "gene expression" means the transcription of a specific gene or specific genes or specific genetic construct. The term "expression" or "gene expression" in particular means the transcription of a gene or genes or genetic construct into structural RNA (rRNA, tRNA) or mRNA with or without subsequent translation of the latter into a protein. The process includes transcription of DNA and processing of the resulting mRNA product.

Increased Expression/Overexpression

The term "increased expression" or "overexpression" as used herein means any form of expression that is additional to the original wild-type expression level.

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

Endogenous Gene

Reference herein to an "endogenous" gene not only refers to the gene in question as found in a plant in its natural form (i.e., without there being any human intervention), but also refers to that same gene (or a substantially homologous nucleic acid/gene) in an isolated form subsequently (re)introduced into a plant (a transgene). For example, a transgenic plant containing such a transgene may encounter a substantial reduction of the transgene expression and/or substantial reduction of expression of the endogenous gene. The isolated gene may be isolated from an organism or may be manmade, for example by chemical synthesis.

Selectable Marker (Gene)/Reporter Gene

"Selectable marker", "selectable marker gene" or "reporter gene" includes any gene that confers a phenotype on a cell in which it is expressed to facilitate the identification and/or selection of cells that are transfected or transformed with a nucleic acid construct of the invention. These marker genes enable the identification of a successful transfer of the nucleic acid molecules via a series of different principles. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin, or genes conferring resistance to, for example, bleomycin, streptomycin, tetracyclin, chloramphenicol, ampicillin, gentamycin, geneticin (G418), spectinomycin or blasticidin), to herbicides (for example bar which provides resistance to Basta®; aroA or gox providing resistance against glyphosate, or the genes conferring resistance to, for example, imidazolinone, phosphinothricin or sulfonylurea), or genes that provide a metabolic trait (such as manA that allows plants to use mannose as sole carbon source or xylose isomerase for the utilisation of xylose, or antinutritive markers such as the resistance to 2-deoxyglucose). Expression of visual marker genes results in the formation of colour (for example β-glucuronidase, GUS or β-galactosidase with its coloured substrates, for example X-Gal), luminescence (such as the luciferin/luciferase system) or fluorescence (Green Fluorescent Protein, GFP, and derivatives thereof). This list represents only a small number of possible markers. The skilled worker is familiar with such markers. Different markers are preferred, depending on the organism and the selection method.

It is known that upon stable or transient integration of nucleic acids into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can for example be used in mutants in which these genes are not functional by, for example, deletion by conventional methods. Furthermore, nucleic acid molecules encoding a selectable marker can be introduced into a host cell on the same vector that comprises the sequence encoding the polypeptides of the invention or used in the methods of the invention, or else in a separate vector. Cells which have been stably transfected with the introduced nucleic acid can be identified for example by selection (for example, cells which have integrated the selectable marker survive whereas the other cells die).

Since the marker genes, particularly genes for resistance to antibiotics and herbicides, are no longer required or are undesired in the transgenic host cell once the nucleic acids have been introduced successfully, the process according to the invention for introducing the nucleic acids advantageously employs techniques which enable the removal or excision of these marker genes. One such a method is what is known as co-transformation. The co-transformation method employs two vectors simultaneously for the transformation, one vector bearing the nucleic acid according to the invention and a second bearing the marker gene(s). A large proportion of transformants receives or, in the case of plants, comprises (up to 40% or more of the transformants), both vectors. In case of transformation with Agrobacteria, the transformants usually receive only a part of the vector, i.e. the sequence flanked by the T-DNA, which usually represents the expression cassette. The marker genes can subsequently be removed from the transformed plant by performing crosses. In another method, marker genes integrated into a transposon are used for the transformation together with desired nucleic acid (known as the Ac/Ds technology). The transformants can be crossed with a transposase source or the transformants are transformed with a nucleic acid construct conferring expression of a transposase, transiently or stable. In some cases (approx. 10%), the transposon jumps out of the genome of the host cell once transformation has taken place successfully and is lost. In a further number of cases, the transposon jumps to a different location. In these cases the marker gene must be eliminated by performing crosses. In microbiology, techniques were developed which make possible, or facilitate, the detection of such events. A further advantageous method relies on what is known as recombination systems; whose advantage is that elimination by crossing can be dispensed with. The best-known system of this type is what is known as the Cre/lox system. Cre1 is a recombinase that removes the sequences located between the loxP sequences. If the marker gene is integrated between the loxP sequences, it is removed once transformation has taken place successfully, by expression of the recombinase. Further recombination systems are the HIN/HIX, FLP/FRT and REP/STB system (Tribble et al., J. Biol. Chem., 275, 2000: 22255-22267; Velmurugan et al., J. Cell Biol., 149, 2000: 553-566). A site-specific integration into the plant genome of the nucleic acid sequences according to the invention is possible. Naturally, these methods can also be applied to microorganisms such as yeast, fungi or bacteria.

Transgenic/Transgene/Recombinant

For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or
(b) genetic control sequence(s) which is operably linked with the nucleic acid sequence according to the invention, for example a promoter, or
(c) a) and b)

are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic plant for the purposes of the invention is thus understood as meaning, as above, that the nucleic acids used in the method of the invention are not at their natural locus in the genome of said plant, it being possible for the nucleic acids to be expressed homologously or heterologously. However, as mentioned, transgenic also means that, while the nucleic acids according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic plants are mentioned herein.

Transformation

The term "introduction" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plant species is now a fairly routine technique. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987)

Plant Mol Biol 8: 363-373); electroporation of protoplasts (Shillito R. D. et al. (1985) Bio/Technol 3, 1099-1102); microinjection into plant material (Crossway A et al., (1986) Mol. Gen Genet 202: 179-185); DNA or RNA-coated particle bombardment (Klein T M et al., (1987) Nature 327: 70) infection with (non-integrative) viruses and the like. Transgenic plants, including transgenic crop plants, are preferably produced via *Agrobacterium*-mediated transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least on the flower primordia. The plant is subsequently grown on until the seeds of the treated plant are obtained (Clough and Bent, Plant J. (1998) 16, 735-743). Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, such as plants used as a model, like *Arabidopsis* (*Arabidopsis thaliana* is within the scope of the present invention not considered as a crop plant), or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

In addition to the transformation of somatic cells, which then have to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with agrobacteria and seeds are obtained from the developing plants of which a certain proportion is transformed and thus transgenic [Feldman, K A and Marks M D (1987). Mol Gen Genet 208:274-289; Feldmann K (1992). In: C Koncz, N- H Chua and J Shell, eds, Methods in Arabidopsis Research. Word Scientific, Singapore, pp. 274-289]. Alternative methods are based on the repeated removal of the inflorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). C R Acad Sci Paris Life Sci, 316: 1194-1199], while in the case of the "floral dip" method the developing floral tissue is incubated briefly with a surfactant-treated agrobacterial suspension [Clough, S J and Bent A F (1998) The Plant J. 16, 735-743]. A certain proportion of transgenic seeds are harvested in both cases, and these seeds can be distinguished from non-transgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview is given in Bock (2001) Transgenic plastids in basic research and plant biotechnology. J Mol Biol. 2001 Sep. 21; 312 (3): 425-38 or Maliga, P (2003) Progress towards commercialization of plastid transformation technology. Trends Biotechnol. 21, 20-28. Further biotechnological progress has recently been reported in form of marker free plastid transformants, which can be produced by a transient co-integrated maker gene (Klaus et al., 2004, Nature Biotechnology 22(2), 225-229).

T-DNA Activation Tagging

T-DNA activation tagging (Hayashi et al. Science (1992) 1350-1353), involves insertion of T-DNA, usually containing a promoter (may also be a translation enhancer or an intron), in the genomic region of the gene of interest or 10 kb up- or downstream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through *Agrobacterium* infection and leads to modified expression of genes near the inserted T-DNA. The resulting transgenic plants show dominant phenotypes due to modified expression of genes close to the introduced promoter.

TILLING

The term "TILLING" is an abbreviation of "Targeted Induced Local Lesions In Genomes" and refers to a mutagenesis technology useful to generate and/or identify nucleic acids encoding proteins with modified expression and/or activity. TILLING also allows selection of plants carrying such mutant variants. These mutant variants may exhibit modified expression, either in strength or in location or in timing (if the mutations affect the promoter for example). These mutant variants may exhibit higher activity than that exhibited by the gene in its natural form. TILLING combines high-density mutagenesis with high-throughput screening methods. The steps typically followed in TILLING are: (a) EMS mutagenesis (Redei G P and Koncz C (1992) In Methods in Arabidopsis Research, Koncz C, Chua N H, Schell J, eds. Singapore, World Scientific Publishing Co, pp. 16-82;

Feldmann et al., (1994) In Meyerowitz E M, Somerville C R, eds, *Arabidopsis*. Cold Spring Harbor Laboratory Press, Cold Spring Harbor, N.Y., pp 137-172; Lightner J and Caspar T (1998) In J Martinez-Zapater, J Salinas, eds, Methods on Molecular Biology, Vol. 82. Humana Press, Totowa, N.J., pp 91-104); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum et al., (2000) Nat Biotechnol 18: 455-457; reviewed by Stemple (2004) Nat Rev Genet 5(2): 145-50).

Homologous Recombination

Homologous recombination allows introduction in a genome of a selected nucleic acid at a defined selected position. Homologous recombination is a standard technology used routinely in biological sciences for lower organisms such as yeast or the moss *Physcomitrella*. Methods for performing homologous recombination in plants have been described not only for model plants (Offringa et al. (1990) EMBO J 9(10): 3077-84) but also for crop plants, for example rice (Terada et al. (2002) Nat Biotech 20(10): 1030-4; Iida and Terada (2004) Curr Opin Biotech 15(2): 132-8).

Yield

The term "yield" in general means a measurable produce of economic value, typically related to a specified crop, to an area, and to a period of time. Individual plant parts directly contribute to yield based on their number, size and/or weight, or the actual yield is the yield per acre for a crop and year, which is determined by dividing total production (includes both harvested and appraised production) by planted acres. The term "yield" of a plant may relate to vegetative biomass (root and/or shoot biomass), to reproductive organs, and/or to propagules (such as seeds) of that plant.

Early Vigour

"Early vigour" refers to active healthy well-balanced growth especially during early stages of plant growth, and may result from increased plant fitness due to, for example, the plants being better adapted to their environment (i.e. optimizing the use of energy resources and partitioning between shoot and root). Plants having early vigour also show increased seedling survival and a better establishment of the crop, which often results in highly uniform fields (with the crop growing in uniform manner, i.e. with the majority of plants reaching the various stages of development at substantially the same time), and often better and higher yield. Therefore, early vigour may be determined by measuring various factors, such as thousand kernel weight, percentage germination, percentage emergence, seedling growth, seedling height, root length, root and shoot biomass and many more.

Increase/Improve/Enhance

The terms "increase", "improve" or "enhance" are interchangeable and shall mean in the sense of the application at least a 3%, 4%, 5%, 6%, 7%, 8%, 9% or 10%, preferably at least 15% or 20%, more preferably 25%, 30%, 35% or 40% more yield and/or growth in comparison to control plants as defined herein.

Seed Yield

Increased seed yield may manifest itself as one or more of the following: a) an increase in seed biomass (total seed weight) which may be on an individual seed basis and/or per plant and/or per hectare or acre; b) increased number of flowers per plant; c) increased number of (filled) seeds; d) increased seed filling rate (which is expressed as the ratio between the number of filled seeds divided by the total number of seeds); e) increased harvest index, which is expressed as a ratio of the yield of harvestable parts, such as seeds, divided by the total biomass; and f) increased thousand kernel weight (TKW), which is extrapolated from the number of filled seeds counted and their total weight. An increased TKW may result from an increased seed size and/or seed weight, and may also result from an increase in embryo and/or endosperm size.

An increase in seed yield may also be manifested as an increase in seed size and/or seed volume. Furthermore, an increase in seed yield may also manifest itself as an increase in seed area and/or seed length and/or seed width and/or seed perimeter. Increased yield may also result in modified architecture, or may occur because of modified architecture.

Greenness Index

The "greenness index" as used herein is calculated from digital images of plants. For each pixel belonging to the plant object on the image, the ratio of the green value versus the red value (in the RGB model for encoding color) is calculated. The greenness index is expressed as the percentage of pixels for which the green-to-red ratio exceeds a given threshold. Under normal growth conditions, under salt stress growth conditions, and under reduced nutrient availability growth conditions, the greenness index of plants is measured in the last imaging before flowering. In contrast, under drought stress growth conditions, the greenness index of plants is measured in the first imaging after drought.

Plant

The term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agave sisalana, Agropyron* spp., *Agrostis stolonifera, Allium* spp., *Amaranthus* spp., *Ammophila arenaria, Ananas comosus, Annona* spp., *Apium graveolens, Arachis* spp, *Artocarpus* spp., *Asparagus officinalis, Avena* spp. (e.g. *Avena sativa, Avena fatua, Avena byzantina, Avena fatua* var. *sativa, Avena hybrida*), *Averrhoa carambola, Bambusa* sp., *Benincasa hispida, Bertholletia excelsea, Beta vulgaris, Brassica* spp. (e.g. *Brassica napus, Brassica rapa* ssp. [canola, oilseed rape, turnip rape]), *Cadaba farinosa, Camellia sinensis, Canna indica, Cannabis sativa, Capsicum* spp., *Carex elata, Carica papaya, Carissa macrocarpa, Carya* spp., *Carthamus tinctorius, Castanea* spp., *Ceiba pentandra, Cichorium endivia, Cinnamomum* spp., *Citrullus lanatus, Citrus* spp., *Cocos* spp., *Coffea* spp., *Colocasia esculenta, Cola* spp., *Corchorus* sp., *Coriandrum sativum, Corylus* spp., *Crataegus* spp., *Crocus sativus, Cucurbita* spp., *Cucumis* spp., *Cynara* spp., *Daucus carota, Desmodium* spp., *Dimocarpus longan, Dioscorea* spp., *Diospyros* spp., *Echinochloa* spp., *Elaeis* (e.g. *Elaeis guineensis, Elaeis oleifera*), *Eleusine coracana, Erianthus* sp., *Eriobotrya japonica, Eucalyptus* sp., *Eugenia uniflora, Fagopyrum* spp., *Fagus* spp., *Festuca arundinacea, Ficus carica, Fortunella* spp., *Fragaria* spp., *Ginkgo biloba, Glycine* spp. (e.g. *Glycine max, Soja hispida* or *Soja max*), *Gossypium hirsutum, Helianthus* spp. (e.g. *Helianthus annuus*), Hemerocallis fulva, Hibiscus spp., Hordeum spp. (e.g. Hordeum vulgare), Ipomoea batatas, Juglans spp., Lactuca sativa, Lathyrus spp., Lens culinaris, Linum usitatissimum, Litchi chinensis, Lotus spp., Luffa acutangula, Lupinus spp., Luzula sylvatica, Lycopersicon spp. (e.g. Lycopersicon esculentum, Lycopersicon lycopersicum, Lycopersicon pyriforme), Macrotyloma spp., Malus spp., Malpighia emarginata, Mammea americana, Mangifera indica, Manihot spp., Manilkara zapota, Medicago sativa, Melilotus spp., Mentha spp., Miscanthus sinensis, Momordica spp., Morus nigra, Musa spp., Nicotiana spp., Olea spp., Opuntia spp., Ornithopus spp., Oryza spp. (e.g. Oryza sativa, Oryza latifolia), Panicum miliaceum, Panicum virgatum, Passiflora edulis, Pastinaca sativa, Pennisetum sp., Persea spp., Petroselinum crispum, Phalaris arundinacea, Phaseolus spp., Phleum pratense, Phoenix spp., Phragmites australis, Physalis spp., Pinus spp., Pistacia vera, Pisum spp., Poa spp., Populus spp., Prosopis spp., Prunus spp., Psidium spp., Punica granatum, Pyrus communis, Quercus spp., Raphanus sativus, Rheum rhabarbarum, Ribes spp., Ricinus communis, Rubus spp., Saccharum spp., Salix sp., Sambucus spp., Secale cereale, Sesamum spp., Sinapis sp., Solanum spp. (e.g. Solanum tuberosum, Solanum integrifolium or Solanum lycopersicum), Sorghum bicolor, Spinacia spp., Syzygium spp., Tagetes spp., Tamarindus indica, Theobroma cacao, Trifolium spp., Triticosecale rimpaui, Triticum spp. (e.g. Triticum aestivum, Triticum durum, Triticum turgidum, Triticum hybernum, Triticum macha, Triticum sativum or Triticum vulgare), Tropaeolum minus, Tropaeolum majus, Vaccinium spp., Vicia spp., Vigna spp., Viola odorata, Vitis spp., Zea mays, Zizania palustris, Ziziphus spp., amongst others.

DETAILED DESCRIPTION OF THE INVENTION

Surprisingly, it has now been found that modulating expression in a plant of a nucleic acid encoding a GSBP-like polypeptide gives plants having enhanced yield-related traits relative to control plants. According to a first embodiment, the present invention provides a method for enhancing yield-related traits in plants relative to control plants, comprising modulating expression in a plant of a nucleic acid encoding a GSBP-like polypeptide.

A preferred method for modulating (preferably, increasing) expression of a nucleic acid encoding a GSBP-like polypeptide is by introducing and expressing in a plant a nucleic acid encoding a GSBP-like polypeptide.

Any reference hereinafter to a "protein useful in the methods of the invention" is taken to mean a GSBP-like polypeptide as defined herein. Any reference hereinafter to a "nucleic acid useful in the methods of the invention" is taken to mean a nucleic acid capable of encoding such a GSBP-like polypeptide. The nucleic acid to be introduced into a plant (and therefore useful in performing the methods of the invention) is any nucleic acid encoding the type of protein which will now be described, hereafter also named "GSBP-like nucleic acid" or "GSBP-like gene".

A "GSBP-like polypeptide" as defined herein refers to any polypeptide comprising an NTF2 domain (Pfam accession PF02136, InterPro accession IPR002075) located in the N-terminal half of the protein, and an RRM domain (Pfam accession PF00076, InterPro accession IPR000504) located in the C-terminal half of the protein. The RRM domain is postulated to be found in RNA binding proteins, whereas the NTF2 domain is found in proteins involved in nuclear transport. Furthermore, the C-terminal part of the protein, starting from the end of the RRM domain (i.e. after the conserved EE residues) is enriched in Arg and Gly residues: whereas the mean protein composition has an R/G content of 12.22% (amino acid composition of the Swiss-Prot Protein Sequence data bank, release 44, July 2004), the C-terminal part of the GSBP-like proteins have an R/G content of (in increasing order of preference) more than 20%, 25%, 30%. Optionally, the GSBP-like polypeptide comprises an N-glycosylation motif (RGD tripeptide) C-terminally of the RRM domain.

Furthermore, the GSBP-like polypeptide comprises, in increasing order of preference, one, two, three, four, five or more of the following conserved motifs:

Motif 1, SEQ ID NO: 34: GIQVR;
Motif 2, SEQ ID NO: 35: (V/I)EE(K/R)(R/K)
Motif 3, SEQ ID NO: 36: (C/F/N)(F/Y/I)(G/A)F(I/V)(E/A/V)(F/Y)(E/D)
Motif 4, SEQ ID NO: 37: F(K/R/Q)(K/S/A/N)(F/Y)G(A/L/T/P/R/N)(I/V)(K/R/V)
Motif 5, SEQ ID NO: 38: (S/A/Q)(V/I/L)(F/Y)(V/L/I)(K/R/A/G)(S/H/N/G)L(P/S)
Motif 6, SEQ ID NO: 39: (Y/F)(V/F/Y)V(L/F/H)(N/S)D(I/M/V/T)(F/L)(R/Q/K)(F/Y/L)
Motif 7, SEQ ID NO: 40: F(T/S/A/V/M)Q(S/T)(F/M)(F/L/V)L(A/V)(P/S)
Motif 8, SEQ ID NO: 41: (G/A)(V/L/Y)X(I/V/T/M)(V/L/M/Q)V(T/M)G
wherein X may be any amino acid, but preferably one of L, H, T, I, V, M, or Q Preferably, motif 2 is VEEK(R/K) (SEQ ID NO: 42)
Preferably, motif 3 is C(F/Y)GF(I/V)EFE (SEQ ID NO: 43)
Preferably, motif 4 is F(K/R/Q)(K/S/A/N)(F/Y)G(A/L/T/P/R/N)(I/V)(K/R/V) (SEQ ID NO: 37)
Preferably, motif 5 is (S/A)(V/I)(F/Y)(V/L)(K/R)(S/H/N)LP (SEQ ID NO: 44)
Preferably, motif 6 is Y(V/F)V(L/F)ND(I/MN)(F/L)R(F/Y) (SEQ ID NO: 45)
Preferably, motif 7 is F(T/S/A)Q(S/T)FFLAP (SEQ ID NO: 46)
Preferably, motif 8 is G(V/Y)(L/H/T/I/V/M)(I/V)(V/L)VTG (SEQ ID NO: 47)

Preferably, the polypeptide sequence which when used in the construction of a phylogenetic tree, such as the one depicted in FIG. 3, clusters with the group of GSBP-like polypeptides (eventually refer to a specific group defined in the literature) comprising the amino acid sequence represented by SEQ ID NO: 2 rather than with any other group.

The term "domain" and "motif" is defined in the "definitions" section herein. Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788 (2003)). Domains or motifs may also be identified using routine techniques, such as by sequence alignment.

Methods for the alignment of sequences for comparison are well known in the art, such methods include GAP, BEST-FIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters.

Furthermore, GSBP-like polypeptides (at least in their native form) typically have RNA binding activity. Tools and techniques for measuring RNA binding activity are known in the art. Furthermore, GSBP-like polypeptides have the effect of increasing at least total seed yield (expresses as total weight of seeds), when expressed in rice under control of the rice GOS2 promoter (SEQ ID NO: 3) or under control of the rice RCc3 promoter.

The present invention is illustrated by transforming plants with the nucleic acid sequence represented by SEQ ID NO: 1, encoding the polypeptide sequence of SEQ ID NO: 2. However, performance of the invention is not restricted to these sequences; the methods of the invention may advantageously be performed using any GSBP-like protein-encoding nucleic acid or GSBP-like polypeptide as defined herein.

Examples of nucleic acids encoding GSBP-like polypeptides are given in Table A of Example 1 herein. Such nucleic acids are useful in performing the methods of the invention. The amino acid sequences given in Table A of Example 1 are example sequences of orthologues and paralogues of the GSBP-like polypeptide represented by SEQ ID NO: 2, the terms "orthologues" and "paralogues" being as defined herein. Further orthologues and paralogues may readily be identified by performing a so-called reciprocal blast search. Typically, this involves a first BLAST involving BLASTing a query sequence (for example using any of the sequences listed in Table A of Example 1) against any sequence database, such as the publicly available NCBI database. BLASTN or TBLASTX (using standard default values) are generally used when starting from a nucleotide sequence, and BLASTP or TBLASTN (using standard default values) when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 1 or SEQ ID NO: 2, the second BLAST would therefore be against rice sequences). The results of the first and second BLASTs are then compared. A paralogue is identified if a high-ranking hit from the first blast is from the same species as from which the query sequence is derived, a BLAST back then ideally results in the query sequence amongst the highest hits; an orthologue is identified if a high-ranking hit in the first BLAST is not from the same species as from which the query sequence is derived, and preferably results upon BLAST back in the query sequence being among the highest hits.

High-ranking hits are those having a low E-value. The lower the E-value, the more significant the score (or in other words the lower the chance that the hit was found by chance). Computation of the E-value is well known in the art. In addition to E-values, comparisons are also scored by percentage identity. Percentage identity refers to the number of identical nucleotides (or amino acids) between the two compared nucleic acid (or polypeptide) sequences over a particular length. In the case of large families, ClustalW may be used, followed by a neighbour joining tree, to help visualize clustering of related genes and to identify orthologues and paralogues.

Nucleic acid variants may also be useful in practising the methods of the invention. Examples of such variants include nucleic acids encoding homologues and derivatives of any one of the amino acid sequences given in Table A of Example 1, the terms "homologue" and "derivative" being as defined herein. Also useful in the methods of the invention are nucleic acids encoding homologues and derivatives of orthologues or paralogues of any one of the amino acid sequences given in Table A of Example 1. Homologues and derivatives useful in the methods of the present invention have substantially the same biological and functional activity as the unmodified protein from which they are derived.

Further nucleic acid variants useful in practising the methods of the invention include portions of nucleic acids encoding GSBP-like polypeptides, nucleic acids hybridising to nucleic acids encoding GSBP-like polypeptides, splice variants of nucleic acids encoding GSBP-like polypeptides, allelic variants of nucleic acids encoding GSBP-like polypeptides and variants of nucleic acids encoding GSBP-like polypeptides obtained by gene shuffling. The terms hybridising sequence, splice variant, allelic variant and gene shuffling are as described herein.

Nucleic acids encoding GSBP-like polypeptides need not be full-length nucleic acids, since performance of the methods of the invention does not rely on the use of full-length nucleic acid sequences. According to the present invention, there is provided a method for enhancing yield-related traits in plants, comprising introducing and expressing in a plant a portion of any one of the nucleic acid sequences given in Table A of Example 1, or a portion of a nucleic acid encoding an orthologue, paralogue or homologue of any of the amino acid sequences given in Table A of Example 1.

A portion of a nucleic acid may be prepared, for example, by making one or more deletions to the nucleic acid. The portions may be used in isolated form or they may be fused to other coding (or non-coding) sequences in order to, for example, produce a protein that combines several activities. When fused to other coding sequences, the resultant polypeptide produced upon translation may be bigger than that predicted for the protein portion.

Portions useful in the methods of the invention, encode a GSBP-like polypeptide as defined herein, and have substantially the same biological activity as the amino acid sequences given in Table A of Example 1. Preferably, the portion is a portion of any one of the nucleic acids given in Table A of Example 1, or is a portion of a nucleic acid encoding an orthologue or paralogue of any one of the amino acid sequences given in Table A of Example 1. Preferably the portion is at least 600, 650, 700, 750, 800, 850, 900, 950, 1000, 1050, 1100, 1150, 1200, 1250, 1300, 1350, 1400, 1450, 1500, 1550, 1600, 1650, 1700 consecutive nucleotides in length, the consecutive nucleotides being of any one of the nucleic acid sequences given in Table A of Example 1, or of a nucleic acid encoding an orthologue or paralogue of any one of the amino acid sequences given in Table A of Example 1. Most preferably the portion is a portion of the nucleic acid of SEQ ID NO: 1. Preferably, the portion encodes a fragment of an amino acid sequence which, when used in the construction of a phylogenetic tree, such as the one depicted in FIG. 3, clusters with the group of GSBP-like polypeptides comprising the amino acid sequence represented by SEQ ID NO: 2 rather than with any other group.

Another nucleic acid variant useful in the methods of the invention is a nucleic acid capable of hybridising, under reduced stringency conditions, preferably under stringent conditions, with a nucleic acid encoding a GSBP-like polypeptide as defined herein, or with a portion as defined herein.

According to the present invention, there is provided a method for enhancing yield-related traits in plants, comprising introducing and expressing in a plant a nucleic acid capable of hybridizing to any one of the nucleic acids given in Table A of Example 1, or comprising introducing and expressing in a plant a nucleic acid capable of hybridising to a nucleic acid encoding an orthologue, paralogue or homologue of any of the nucleic acid sequences given in Table A of Example 1.

Hybridising sequences useful in the methods of the invention encode a GSBP-like polypeptide as defined herein, having substantially the same biological activity as the amino acid sequences given in Table A of Example 1. Preferably, the hybridising sequence is capable of hybridising to any one of the nucleic acids given in Table A of Example 1, or to a portion of any of these sequences, a portion being as defined above, or the hybridising sequence is capable of hybridising to a nucleic acid encoding an orthologue or paralogue of any one of the amino acid sequences given in Table A of Example 1. Most preferably, the hybridising sequence is capable of hybridising to a nucleic acid as represented by SEQ ID NO: 1 or to a portion thereof.

Preferably, the hybridising sequence encodes a polypeptide with an amino acid sequence which, when full-length and used in the construction of a phylogenetic tree, such as the one depicted in FIG. 3, clusters with the group of GSBP-like polypeptides comprising the amino acid sequence represented by SEQ ID NO: 2 rather than with any other group.

Another nucleic acid variant useful in the methods of the invention is a splice variant encoding a GSBP-like polypeptide as defined hereinabove, a splice variant being as defined herein.

According to the present invention, there is provided a method for enhancing yield-related traits in plants, comprising introducing and expressing in a plant a splice variant of any one of the nucleic acid sequences given in Table A of Example 1, or a splice variant of a nucleic acid encoding an orthologue, paralogue or homologue of any of the amino acid sequences given in Table A of Example 1.

Preferred splice variants are splice variants of a nucleic acid represented by SEQ ID NO: 1, or a splice variant of a nucleic acid encoding an orthologue or paralogue of SEQ ID NO: 2. Preferably, the amino acid sequence encoded by the splice variant, when used in the construction of a phylogenetic tree, such as the one depicted in FIG. 3, clusters with the group of GSBP-like polypeptides comprising the amino acid sequence represented by SEQ ID NO: 2 rather than with any other group.

Another nucleic acid variant useful in performing the methods of the invention is an allelic variant of a nucleic acid encoding a GSBP-like polypeptide as defined hereinabove, an allelic variant being as defined herein.

According to the present invention, there is provided a method for enhancing yield-related traits in plants, comprising introducing and expressing in a plant an allelic variant of any one of the nucleic acids given in Table A of Example 1, or comprising introducing and expressing in a plant an allelic variant of a nucleic acid encoding an orthologue, paralogue or homologue of any of the amino acid sequences given in Table A of Example 1.

The allelic variants useful in the methods of the present invention have substantially the same biological activity as the GSBP-like polypeptide of SEQ ID NO: 2 and any of the amino acids depicted in Table A of Example 1. Allelic variants exist in nature, and encompassed within the methods of the present invention is the use of these natural alleles. Preferably, the allelic variant is an allelic variant of SEQ ID NO: 1 or an allelic variant of a nucleic acid encoding an orthologue or paralogue of SEQ ID NO: 2. Preferably, the amino acid sequence encoded by the allelic variant, when used in the construction of a phylogenetic tree, such as the one depicted in FIG. 3, clusters with the GSBP-like polypeptides comprising the amino acid sequence represented by SEQ ID NO: 2 rather than with any other group.

Gene shuffling or directed evolution may also be used to generate variants of nucleic acids encoding GSBP-like polypeptides as defined above; the term "gene shuffling" being as defined herein.

According to the present invention, there is provided a method for enhancing yield-related traits in plants, comprising introducing and expressing in a plant a variant of any one of the nucleic acid sequences given in Table A of Example 1, or comprising introducing and expressing in a plant a variant of a nucleic acid encoding an orthologue, paralogue or homologue of any of the amino acid sequences given in Table A of Example 1, which variant nucleic acid is obtained by gene shuffling.

Preferably, the amino acid sequence encoded by the variant nucleic acid obtained by gene shuffling, when used in the construction of a phylogenetic tree such as the one depicted in FIG. 3, clusters with the group of GSBP-like polypeptides comprising the amino acid sequence represented by SEQ ID NO: 2 rather than with any other group.

Furthermore, nucleic acid variants may also be obtained by site-directed mutagenesis. Several methods are available to achieve site-directed mutagenesis, the most common being PCR based methods (Current Protocols in Molecular Biology. Wiley Eds.).

Nucleic acids encoding GSBP-like polypeptides may be derived from any natural or artificial source. The nucleic acid may be modified from its native form in composition and/or genomic environment through deliberate human manipulation. Preferably the GSBP-like polypeptide-encoding nucleic acid is from a plant, further preferably from a monocotyledonous plant, more preferably from the family Poaceae, most preferably the nucleic acid is from *Oryza sativa*.

Performance of the methods of the invention gives plants having enhanced yield-related traits. In particular performance of the methods of the invention gives plants having increased yield, especially increased seed yield relative to control plants. Furthermore, the methods of the invention gives plants having increased early vigour. The terms "yield", "seed yield" and early vigour are described in more detail in the "definitions" section herein.

Reference herein to enhanced yield-related traits is taken to mean an increase in biomass (weight) of one or more parts of a plant, which may include aboveground (harvestable) parts and/or (harvestable) parts below ground. In particular, such harvestable parts are aboveground biomass and seeds, and performance of the methods of the invention results in plants having increased yield in aboveground biomass and increased seed yield relative to the biomass and seed yield of control plants. The term yield-related traits as used herein also encompasses early vigour.

Taking corn as an example, a yield increase may be manifested as one or more of the following: increase in the number of plants established per hectare or acre, an increase in the number of ears per plant, an increase in the number of rows, number of kernels per row, kernel weight, thousand kernel weight, ear length/diameter, increase in the seed filling rate (which is the number of filled seeds divided by the total number of seeds and multiplied by 100), among others. Taking rice as an example, a yield increase may manifest itself as an increase in one or more of the following: number of plants per hectare or acre, number of panicles per plant, number of spikelets per panicle, number of flowers (florets) per panicle (which is expressed as a ratio of the number of filled seeds over the number of primary panicles), increase in the seed filling rate (which is the number of filled seeds divided by the total number of seeds and multiplied by 100), increase in thousand kernel weight, among others.

The present invention provides a method for increasing yield, especially aboveground biomass, seed yield of plants, and/or early vigour, relative to control plants, which method comprises modulating expression, preferably increasing expression, in a plant of a nucleic acid encoding a GSBP-like polypeptide as defined herein.

Since the transgenic plants according to the present invention have increased yield, it is likely that these plants exhibit an increased growth rate (during at least part of their life cycle), relative to the growth rate of control plants at a corresponding stage in their life cycle.

The increased growth rate may be specific to one or more parts of a plant (including seeds), or may be throughout substantially the whole plant. Plants having an increased growth rate may have a shorter life cycle. The life cycle of a plant may be taken to mean the time needed to grow from a dry mature seed up to the stage where the plant has produced dry mature seeds, similar to the starting material. This life cycle may be influenced by factors such as early vigour, growth rate, greenness index, flowering time and speed of seed maturation. The increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than would otherwise be possible (a similar effect may be obtained with earlier flowering time). If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the planting and harvesting of corn plants followed by, for example, the planting and optional harvesting of soybean, potato or any other suitable plant). Harvesting additional times from the same rootstock in the case of some crop plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

According to a preferred feature of the present invention, performance of the methods of the invention gives plants having an increased growth rate relative to control plants. Therefore, according to the present invention, there is provided a method for increasing the growth rate of plants, which method comprises modulating expression, preferably increasing expression, in a plant of a nucleic acid encoding a GSBP-like polypeptide as defined herein.

An increase in yield and/or growth rate occurs whether the plant is under non-stress conditions or whether the plant is exposed to various stresses compared to control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Mild stress in the sense of the invention leads to a reduction in the growth of the stressed plants of less than 40%, 35% or 30%, preferably less than 25%, 20% or 15%, more preferably less than 14%, 13%, 12%, 11% or 10% or less in comparison to the control plant under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the everyday biotic and/or abiotic (environmental) stresses to which a plant is exposed. Abiotic stresses may be due to drought or excess water, anaerobic stress, salt stress, chemical toxicity, oxidative stress and hot, cold or freezing temperatures. The abiotic stress may be an osmotic stress caused by a water stress (particularly due to drought), salt stress, oxidative stress or an ionic stress. Biotic stresses are typically those stresses caused by pathogens, such as bacteria, viruses, fungi and insects.

In particular, the methods of the present invention may be performed under non-stress conditions or under conditions of mild drought to give plants having increased yield relative to control plants. As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. Rabbani et al. (Plant Physiol (2003) 133: 1755-1767) describes a particularly high degree of "cross talk" between drought stress and high-salinity stress. For example, drought and/or salinisation are manifested primarily as osmotic stress, resulting in the disruption of homeostasis and ion distribution in the cell. Oxidative stress, which frequently accompanies high or low temperature, salinity or drought stress, may cause denaturing of functional and structural proteins. As a consequence, these diverse environmental stresses often activate similar cell signalling pathways and cellular responses, such as the production of stress proteins, up-regulation of anti-oxidants, accumulation of compatible solutes and growth arrest. The term "non-stress" conditions as used herein are those environmental conditions that allow optimal growth of plants. Persons skilled in the art are aware of normal soil conditions and climatic conditions for a given location.

Performance of the methods of the invention gives plants grown under non-stress conditions or under mild drought conditions increased yield relative to control plants grown under comparable conditions. Therefore, according to the present invention, there is provided a method for increasing yield in plants grown under non-stress conditions or under mild drought conditions, which method comprises increasing expression in a plant of a nucleic acid encoding a GSBP-like polypeptide.

Performance of the methods of the invention gives plants grown under conditions of nutrient deficiency, particularly under conditions of nitrogen deficiency, increased yield relative to control plants grown under comparable conditions. Therefore, according to the present invention, there is provided a method for increasing yield in plants grown under conditions of nutrient deficiency, which method comprises increasing expression in a plant of a nucleic acid encoding a GSBP-like polypeptide. Nutrient deficiency may result from a lack of nutrients such as nitrogen, phosphates and other phosphorous-containing compounds, potassium, calcium, cadmium, magnesium, manganese, iron and boron, amongst others.

The present invention encompasses plants or parts thereof (including seeds) obtainable by the methods according to the present invention. The plants or parts thereof comprise a nucleic acid transgene encoding a GSBP-like polypeptide as defined above.

The invention also provides genetic constructs and vectors to facilitate introduction and/or expression in plants of nucleic acids encoding GSBP-like polypeptides. The gene constructs may be inserted into vectors, which may be commercially available, suitable for transforming into plants and suitable for expression of the gene of interest in the transformed cells. The invention also provides use of a gene construct as defined herein in the methods of the invention.

More specifically, the present invention provides a construct comprising:
(a) a nucleic acid encoding a GSBP-like polypeptide as defined above;
(b) one or more control sequences capable of driving expression of the nucleic acid sequence of (a); and optionally
(c) a transcription termination sequence.

Preferably, the nucleic acid encoding a GSBP-like polypeptide is as defined above. The term "control sequence" and "termination sequence" are as defined herein.

Plants are transformed with a vector comprising any of the nucleic acids described above. The skilled artisan is well aware of the genetic elements that must be present on the vector in order to successfully transform, select and propagate host cells containing the sequence of interest. The sequence of interest is operably linked to one or more control sequences (at least to a promoter).

Advantageously, any type of promoter, whether natural or synthetic, may be used to drive expression of the nucleic acid sequence. A constitutive promoter is particularly useful in the methods. Preferably, the constitutive promoter is at least active in the roots, more preferably the constitutive promoter is a ubiquitous promoter. See the "Definitions" section herein for definitions of the various promoter types. Also useful in the methods of the invention is a root-specific promoter.

It should be clear that the applicability of the present invention is not restricted to the GSBP-like polypeptide-encoding nucleic acid represented by SEQ ID NO: 1, nor is the applicability of the invention restricted to expression of a GSBP-like polypeptide-encoding nucleic acid when driven by a constitutive promoter, or when driven by a root-specific promoter.

The constitutive promoter is preferably a GOS2 promoter, preferably a GOS2 promoter from rice. Further preferably the constitutive promoter is represented by a nucleic acid sequence substantially similar to SEQ ID NO: 3, most preferably the constitutive promoter is as represented by SEQ ID NO: 3. See Table 2 in the "Definitions" section herein for further examples of constitutive promoters.

According to another preferred feature of the invention, the nucleic acid encoding a GSBP-like polypeptide is operably linked to a root-specific promoter. The root-specific promoter is preferably an RCc3 promoter (Plant Mol Biol. 1995 January; 27(2):237-48), more preferably the RCc3 promoter is from rice, further preferably the RCc3 promoter is represented by a nucleic acid sequence substantially similar to SEQ ID NO: 4, most preferably the promoter is as represented by SEQ ID NO: 4. Examples of other root-specific promoters which may also be used to perform the methods of the invention are shown in Table 3 in the "Definitions" section above.

Optionally, one or more terminator sequences may be used in the construct introduced into a plant. Additional regulatory elements may include transcriptional as well as translational enhancers. Those skilled in the art will be aware of terminator and enhancer sequences that may be suitable for use in performing the invention. An intron sequence may also be added to the 5' untranslated region (UTR) or in the coding sequence to increase the amount of the mature message that accumulates in the cytosol, as described in the definitions section. Other control sequences (besides promoter, enhancer, silencer, intron sequences, 3'UTR and/or 5'UTR regions) may be protein and/or RNA stabilizing elements. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-on and colE1.

For the detection of the successful transfer of the nucleic acid sequences as used in the methods of the invention and/or selection of transgenic plants comprising these nucleic acids, it is advantageous to use marker genes (or reporter genes). Therefore, the genetic construct may optionally comprise a selectable marker gene. Selectable markers are described in more detail in the "definitions" section herein. The marker genes may be removed or excised from the transgenic cell once they are no longer needed. Techniques for marker removal are known in the art, useful techniques are described above in the definitions section.

The invention also provides a method for the production of transgenic plants having enhanced yield-related traits relative to control plants, comprising introduction and expression in a plant of any nucleic acid encoding a GSBP-like polypeptide as defined hereinabove.

More specifically, the present invention provides a method for the production of transgenic plants having increased enhanced yield-related traits, particularly increased biomass and/or (seed) yield, and/or increased early vigour, which method comprises:

(i) introducing and expressing in a plant or plant cell a GSBP-like polypeptide-encoding nucleic acid; and
(ii) cultivating the plant cell under conditions promoting plant growth and development.

The nucleic acid of (i) may be any of the nucleic acids capable of encoding a GSBP-like polypeptide as defined herein.

The nucleic acid may be introduced directly into a plant cell or into the plant itself (including introduction into a tissue, organ or any other part of a plant). According to a preferred feature of the present invention, the nucleic acid is preferably introduced into a plant by transformation. The term "transformation" is described in more detail in the "definitions" section herein.

The genetically modified plant cells can be regenerated via all methods with which the skilled worker is familiar. Suitable methods can be found in the abovementioned publications by S. D. Kung and R. Wu, Potrykus or Höfgen and Willmitzer.

Generally after transformation, plant cells or cell groupings are selected for the presence of one or more markers which are encoded by plant-expressible genes co-transferred with the gene of interest, following which the transformed material is regenerated into a whole plant. To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The invention also includes host cells containing an isolated nucleic acid encoding a GSBP-like polypeptide as defined hereinabove. Preferred host cells according to the invention are plant cells. Host plants for the nucleic acids or the vector used in the method according to the invention, the expression cassette or construct or vector are, in principle, advantageously all plants, which are capable of synthesizing the polypeptides used in the inventive method.

The methods of the invention are advantageously applicable to any plant. Plants that are particularly useful in the methods of the invention include all plants which belong to the superfamily Viridiplantae, in particular monocotyledonous and dicotyledonous plants including fodder or forage legumes, ornamental plants, food crops, trees or shrubs. According to a preferred embodiment of the present invention, the plant is a crop plant. Examples of crop plants include soybean, sunflower, canola, alfalfa, rapeseed, cotton, tomato, potato and tobacco. Further preferably, the plant is a monocotyledonous plant. Examples of monocotyledonous plants include sugarcane. More preferably the plant is a cereal. Examples of cereals include rice, maize, wheat, barley, millet, rye, triticale, sorghum and oats.

The invention also extends to harvestable parts of a plant such as, but not limited to seeds, leaves, fruits, flowers, stems, roots, rhizomes, tubers and bulbs. The invention furthermore relates to products derived, preferably directly derived, from a harvestable part of such a plant, such as dry pellets or powders, oil, fat and fatty acids, starch or proteins.

According to a preferred feature of the invention, the modulated expression is increased expression. Methods for increasing expression of nucleic acids or genes, or gene products, are well documented in the art and examples are provided in the definitions section.

As mentioned above, a preferred method for modulating (preferably, increasing) expression of a nucleic acid encoding a GSBP-like polypeptide is by introducing and expressing in a plant a nucleic acid encoding a GSBP-like polypeptide; however the effects of performing the method, i.e. enhancing yield-related traits may also be achieved using other well known techniques, including but not limited to T-DNA activation tagging, TILLING, homologous recombination. A description of these techniques is provided in the definitions section.

The present invention also encompasses use of nucleic acids encoding GSBP-like polypeptides as described herein and use of these GSBP-like polypeptides in enhancing any of the aforementioned yield-related traits in plants.

Nucleic acids encoding GSBP-like polypeptide described herein, or the GSBP-like polypeptides themselves, may find use in breeding programmes in which a DNA marker is identified which may be genetically linked to a GSBP-like polypeptide-encoding gene. The nucleic acids/genes, or the GSBP-like polypeptides themselves may be used to define a molecular marker. This DNA or protein marker may then be used in breeding programmes to select plants having enhanced yield-related traits as defined hereinabove in the methods of the invention.

Allelic variants of a GSBP-like polypeptide-encoding nucleic acid/gene may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place, for example, by PCR. This is followed by a step for selection of superior allelic variants of the sequence in question and which give increased yield. Selection is typically carried out by monitoring growth performance of plants containing different allelic variants of the sequence in question. Growth performance may be monitored in a greenhouse or in the field. Further optional steps include crossing plants in which the superior allelic variant was identified with another plant. This could be used, for example, to make a combination of interesting phenotypic features.

Nucleic acids encoding GSBP-like polypeptides may also be used as probes for genetically and physically mapping the genes that they are a part of, and as markers for traits linked to those genes. Such information may be useful in plant breeding in order to develop lines with desired phenotypes. Such use of GSBP-like polypeptide-encoding nucleic acids requires only a nucleic acid sequence of at least 15 nucleotides in length. The GSBP-like polypeptide-encoding nucleic acids may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with the GSBP-like protein-encoding nucleic acids. The resulting banding patterns may then be subjected to genetic analyses using computer programs such as MapMaker (Lander et al. (1987) Genomics 1: 174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the GSBP-like polypeptide-encoding nucleic acid in the genetic map previously obtained using this population (Botstein et al. (1980) Am. J. Hum. Genet. 32:314-331).

The production and use of plant gene-derived probes for use in genetic mapping is described in Bernatzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid probes may be used in direct fluorescence in situ hybridisation (FISH) mapping (Trask (1991) Trends Genet. 7:149-154). Although current methods of FISH mapping favour use of large clones (several kb to several hundred kb; see Laan et al. (1995) Genome Res. 5:13-20), improvements in sensitivity may allow performance of FISH mapping using shorter probes.

A variety of nucleic acid amplification-based methods for genetic and physical mapping may be carried out using the nucleic acids. Examples include allele-specific amplification (Kazazian (1989) J. Lab. Clin. Med 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

The methods according to the present invention result in plants having enhanced yield-related traits, as described hereinbefore. These traits may also be combined with other economically advantageous traits, such as further yield-enhancing traits, tolerance to other abiotic and biotic stresses, traits modifying various architectural features and/or biochemical and/or physiological features.

DESCRIPTION OF FIGURES

The present invention will now be described with reference to the following figures in which:

FIG. 1 shows the domain structure of a GSBP-like protein, in case of SEQ ID NO: 2. The NTF2 domain as identified with Pfam is shown in bold, the RRM domain (identified with SMART) is underlined. Two RGD motifs are underlined and in italics.

Figure 2:
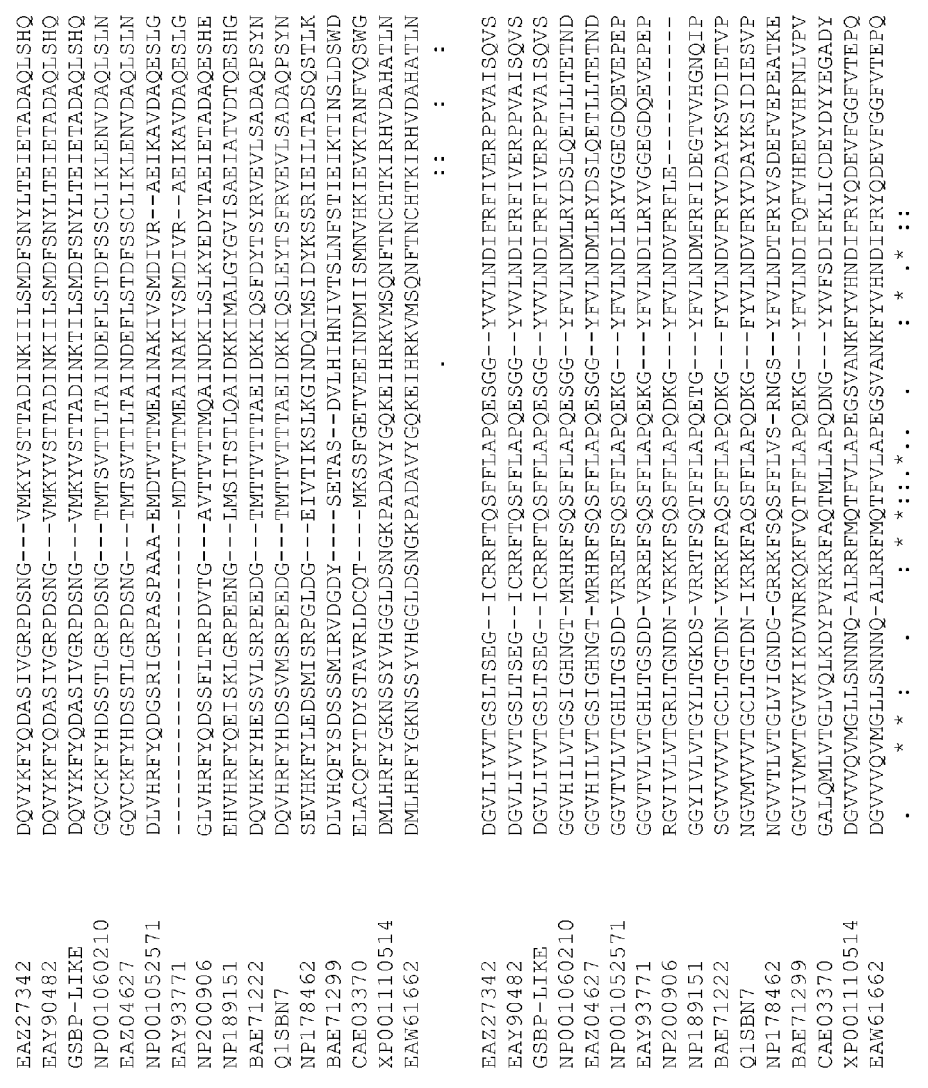
Figure 2:
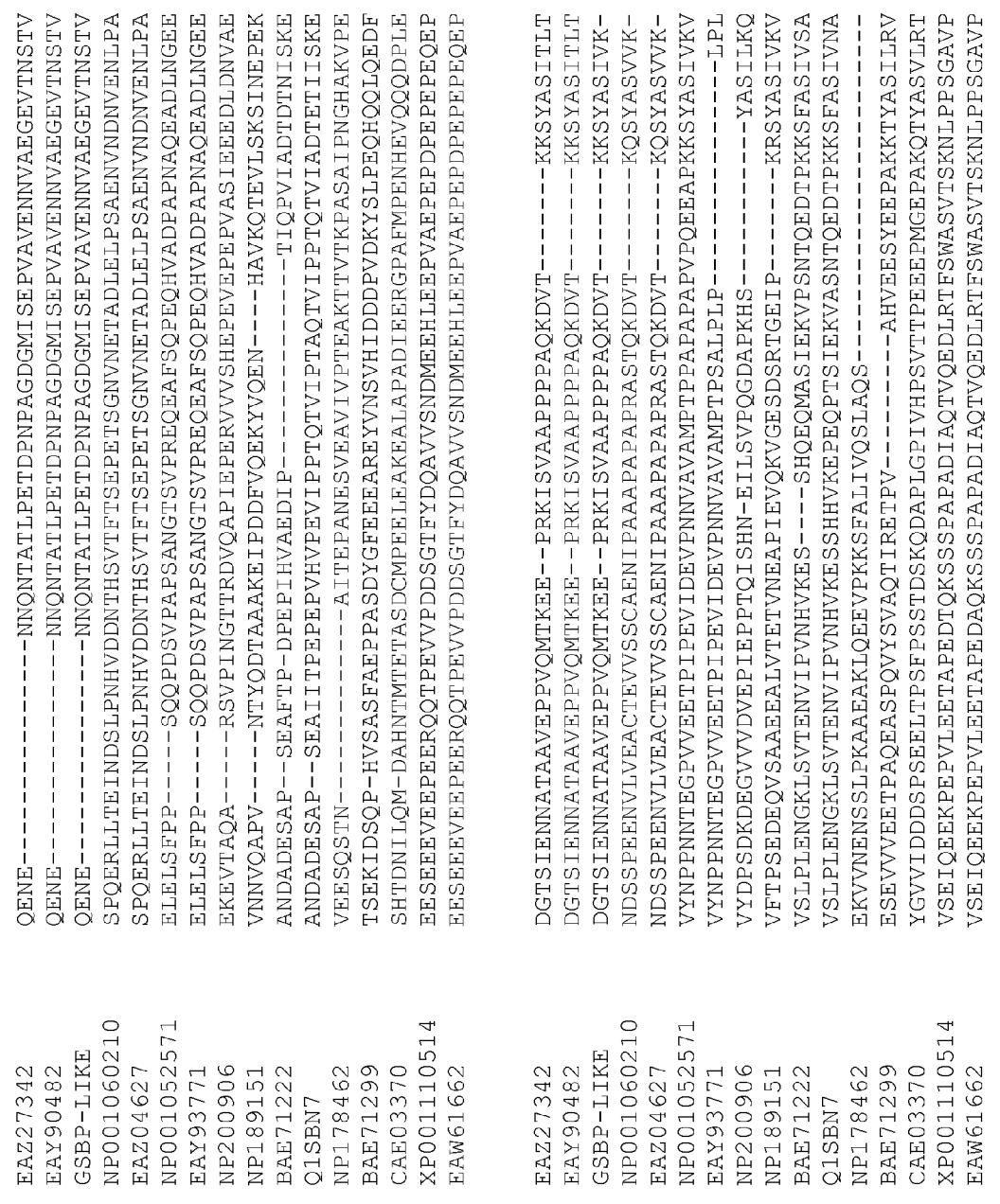
Figure 2:
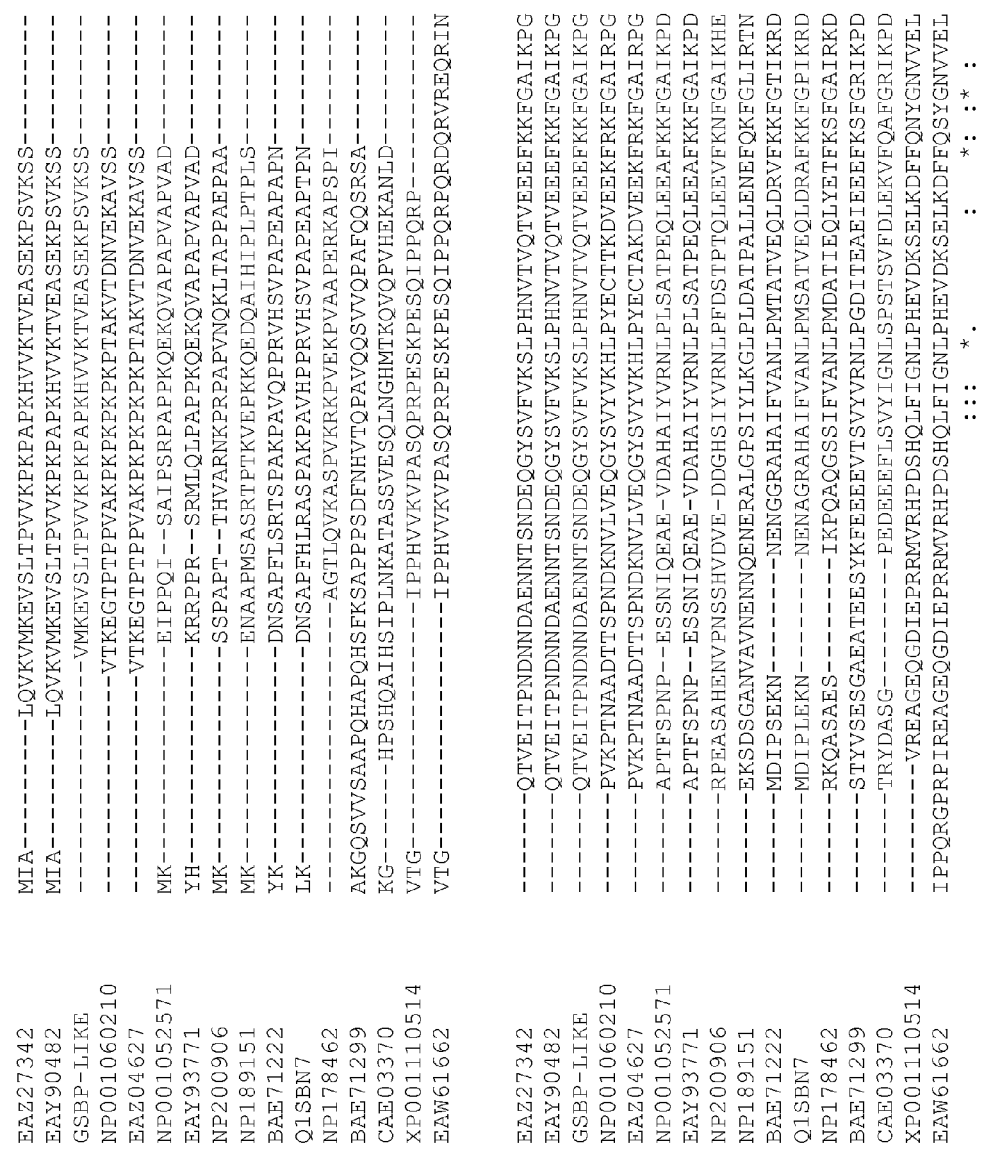

FIG. 2 represents a multiple alignment of various GSBP proteins useful in the methods of the present invention. The asterisks indicate absolute conserved amino acids, the colons denote highly conserved substitutions and the dots indicate less conserved substitutions. The following polypeptides are shown: EAZ27342 (SEQ ID NO: 7), EAY90482 (SEQ ID NO: 8), GSBP-LIKE (SEQ ID NO: 2), NP001060210 (SEQ ID NO: 10), EAZ04627 (SEQ ID NO: 11), NP001052571 (SEQ ID NO: 17), EAY93771 (SEQ ID NO: 33), NP200906 (SEQ ID NO: 21), NP189151 (SEQ ID NO: 15), BAE71222 (SEQ ID NO: 19), Q1SBN7 (SEQ ID NO: 29), NP178462 (SEQ ID NO: 13), BAE71299 (SEQ ID NO: 25), CAE03370 (SEQ ID NO: 27), XP001110514 (SEQ ID NO: 23), and EAW61662 (SEQ ID NO: 31).

FIG. 5 details examples of sequences useful in performing the methods according to the present invention.

EXAMPLES

Figure 3:
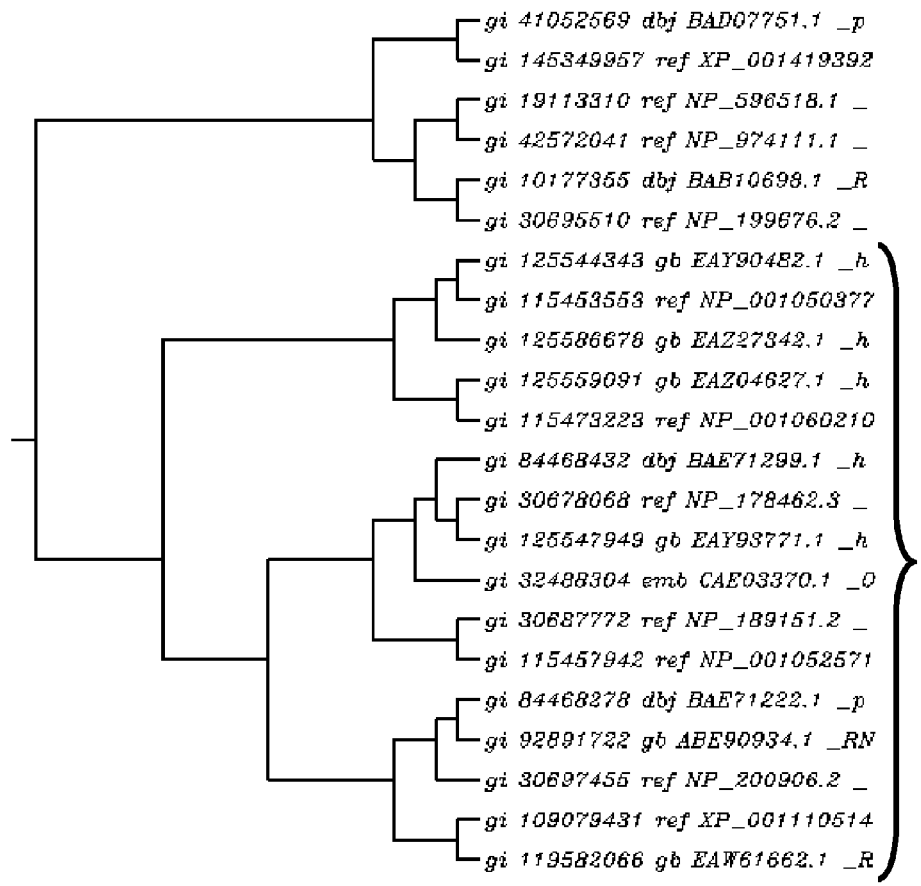
FIG. 3 shows a phylogenetic tree of GSBP-like proteins useful in the methods of the present invention. The database accession numbers are given for each of the proteins; SEQ ID NO: 2 is represented as NP_001050377. The brace delineates the group of GSBP-like proteins from the outgroup.

The present invention will now be described with reference to the following examples, which are by way of illustration alone. The following examples are not intended to completely define or otherwise limit the scope of the invention.

DNA manipulation: unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols. Standard materials and methods for plant molecular work are described in Plant Molecular Biology Labfax (1993) by R. D. D. Croy, published by BIOS Scientific Publications Ltd (UK) and Blackwell Scientific Publications (UK).

Example 1

Identification of Sequences Related to the Nucleic Acid Sequence Used in the Methods of the Invention Sequences (full length cDNA, ESTs or genomic) related to the nucleic acid sequence used in the methods of the present invention were identified amongst those maintained in the Entrez Nucleotides database at the National Center for Biotechnology Information (NCBI) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program is used to find regions of local similarity between sequences by comparing nucleic acid or polypeptide sequences to sequence databases and by calculating the statistical significance of matches. For example, the polypeptide encoded by the nucleic acid used in the present invention was used for the TBLASTN algorithm, with default settings and the filter to ignore low complexity sequences set off. The output of the analysis was viewed by pairwise comparison, and ranked according to the probability score (E-value), where the score reflect the probability that a particular alignment occurs by chance (the lower the E-value, the more significant the hit). In addition to E-values, comparisons were also scored by percentage identity. Percentage identity refers to the number of identical nucleotides (or amino acids) between the two compared nucleic acid (or polypeptide) sequences over a particular length. In some instances, the default parameters may be adjusted to modify the stringency of the search. For example the E-value may be increased to show less stringent matches. This way, short nearly exact matches may be identified.

Table A provides a list of nucleic acid sequences related to the nucleic acid sequence used in the methods of the present invention.

TABLE A

Examples of GSBP-like polypeptides:

| Plant Source | Nucleic acid SEQ ID NO: | Protein SEQ ID NO: |
|---|---|---|
| Oryza sativa | 1 | 2 |
| Oryza sativa |  | 7 |
| Oryza sativa |  | 8 |
| Oryza sativa | 9 | 10 |
| Oryza sativa |  | 11 |
| Arabidopsis thaliana | 12 | 13 |
| Arabidopsis thaliana | 14 | 15 |
| Oryza sativa | 16 | 17 |
| Trifolium pratense | 18 | 19 |
| Arabidopsis thaliana | 20 | 21 |
| Macaca mulatta | 22 | 23 |
| Trifolium pratense | 24 | 25 |
| Oryza sativa | 26 | 27 |
| Medicago truncatula | 28 | 29 |
| Homo sapiens | 30* | 31 |
| Oryza sativa | 32 | 33 |

*the DNA sequence lacks the N-terminal end of the protein sequence

In some instances, related sequences have tentatively been assembled and publicly disclosed by research institutions, such as The Institute for Genomic Research (TIGR). The Eukaryotic Gene Orthologs (EGO) database may be used to identify such related sequences, either by keyword search or by using the BLAST algorithm with the nucleic acid or polypeptide sequence of interest.

Example 2

Alignment of GSBP-Like Polypeptide Sequences

Alignment of polypeptide sequences was performed using the AlignX programme from the Vector NTI (Invitrogen) which is based on the popular Clustal W algorithm of progressive alignment (Thompson et al. (1997) Nucleic Acids Res 25:4876-4882; Chenna et al. (2003). Nucleic Acids Res 31:3497-3500). Default values are for the gap open penalty of 10, for the gap extension penalty of 0.1 and the selected weight matrix is Blosum 62 (if polypeptides are aligned). Minor manual editing was done to further optimise the alignment. Sequence conservation among GSBP-like polypeptides is distributed throughout the entire protein sequence, but is particularly found in the NTF2 domain and in the RRM domain. Furthermore, the enrichment of R and G residues in the C-terminal part is readily recognisable from the alignment. The GSBP-like polypeptides are aligned in FIG. 2.

A phylogenetic tree of GSBP-like polypeptides (FIG. 3) was constructed using a neighbour-joining clustering algorithm as provided in the AlignX programme from the Vector NTI (Invitrogen).

Example 3

Calculation of Global Percentage Identity Between Polypeptide Sequences Useful in Performing the Methods of the Invention Global percentages of similarity and identity between full length polypeptide sequences useful in performing the methods of the invention were determined using one of the methods available in the art, the MatGAT (Matrix Global Alignment Tool) software (BMC Bioinformatics. 2003 4:29. MatGAT: an application that generates similarity/identity matrices using protein or DNA sequences. Campanella J J, Bitincka L, Smalley J; software hosted by Ledion Bitincka). MatGAT software generates similarity/identity matrices for DNA or protein sequences without needing pre-alignment of the data. The program performs a series of pair-wise alignments using the Myers and Miller global alignment algorithm (with a gap opening penalty of 12, and a gap extension penalty of 2), calculates similarity and identity using for example Blosum 62 (for polypeptides), and then places the results in a distance matrix. Sequence similarity is shown in the bottom half of the dividing line and sequence identity is shown in the top half of the diagonal dividing line.

Parameters used in the comparison were:

| Scoring matrix: | Blosum62 |
|---|---|
| First Gap: | 12 |
| Extending gap: | 2 |

Results of the software analysis are shown in Table B for the global similarity and identity over the full length of the polypeptide sequences. Percentage identity is given above the diagonal in bold and percentage similarity is given below the diagonal (normal face).

The percentage identity between the GSBP-like polypeptide sequences useful in performing the methods of the invention can be as low as yy % amino acid identity compared to SEQ ID NO: 2.

TABLE B

MatGAT results for global similarity and identity over the full length of the polypeptide sequences.

|  | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 1. SEQID2 |  | 98.2 | 83.5 | 45.5 | 45.5 | 29.7 | 38.1 | 37.0 | 38.7 | 37.0 | 26.8 | 27.9 | 23.5 | 36.5 | 25.0 | 29.6 |
| 2. SEQID7 | 98.2 |  | 85.1 | 45.2 | 45.2 | 29.8 | 37.0 | 36.4 | 38.4 | 36.2 | 25.8 | 28.2 | 23.5 | 35.5 | 24.6 | 29.5 |
| 3. SEQID8 | 83.5 | 85.1 |  | 39.0 | 39.0 | 25.7 | 32.1 | 32.1 | 32.6 | 31.6 | 22.2 | 25.0 | 21.1 | 30.3 | 23.7 | 25.2 |
| 4. SEQID10 | 54.7 | 55.5 | 53.3 |  | 99.1 | 28.4 | 32.7 | 34.7 | 31.8 | 35.0 | 23.5 | 26.2 | 22.4 | 29.4 | 23.2 | 28.3 |
| 5. SEQID11 | 54.5 | 55.4 | 53.2 | 99.3 |  | 28.1 | 32.2 | 34.5 | 31.5 | 34.8 | 23.7 | 26.1 | 22.4 | 29.4 | 23.0 | 28.1 |
| 6. SEQID13 | 48.8 | 48.2 | 40.5 | 43.4 | 43.1 |  | 29.8 | 33.5 | 36.3 | 33.1 | 25.4 | 29.8 | 22.4 | 35.1 | 22.7 | 30.0 |
| 7. SEQID15 | 54.3 | 52.6 | 45.1 | 46.9 | 46.4 | 45.1 |  | 40.0 | 39.8 | 40.4 | 25.2 | 31.3 | 26.4 | 37.1 | 24.7 | 32.9 |
| 8. SEQID17 | 54.1 | 53.2 | 46.1 | 47.6 | 47.5 | 46.5 | 55.5 |  | 39.7 | 45.9 | 28.0 | 34.9 | 27.7 | 38.3 | 26.1 | 81.1 |
| 9. SEQID19 | 55.7 | 55.2 | 47.0 | 47.8 | 47.3 | 52.8 | 55.5 | 53.7 |  | 42.5 | 28.1 | 31.3 | 26.0 | 82.9 | 25.7 | 33.2 |
| 10. SEQID21 | 53.9 | 52.6 | 45.6 | 48.0 | 47.8 | 50.2 | 55.5 | 59.7 | 60.2 |  | 28.1 | 33.0 | 26.4 | 39.8 | 26.0 | 39.3 |
| 11. SEQID23 | 44.7 | 42.9 | 36.7 | 38.5 | 38.5 | 45.2 | 41.6 | 43.2 | 47.2 | 46.7 |  | 25.1 | 21.5 | 26.2 | 87.5 | 24.3 |
| 12. SEQID25 | 49.0 | 47.2 | 41.0 | 43.2 | 43.1 | 45.2 | 50.0 | 51.6 | 49.3 | 51.1 | 43.9 |  | 32.6 | 29.4 | 23.9 | 29.2 |
| 13. SEQID27 | 42.2 | 41.3 | 36.4 | 37.4 | 37.4 | 43.6 | 43.9 | 44.0 | 46.3 | 47.0 | 41.2 | 53.6 |  | 23.7 | 21.8 | 24.0 |
| 14. SEQID29 | 54.1 | 52.2 | 44.4 | 45.3 | 45.0 | 54.1 | 54.1 | 51.9 | 89.2 | 57.2 | 43.1 | 48.0 | 44.2 |  | 23.7 | 34.0 |
| 15. SEQID31 | 44.4 | 45.0 | 40.8 | 38.8 | 38.5 | 40.0 | 42.0 | 43.0 | 41.6 | 42.4 | 87.9 | 41.8 | 39.2 | 39.0 |  | 21.8 |
| 16. SEQID33 | 43.2 | 41.7 | 36.0 | 38.8 | 38.8 | 46.4 | 45.7 | 81.7 | 48.8 | 52.8 | 39.3 | 46.3 | 40.3 | 48.8 | 35.0 |  |

Example 4

Identification of Domains Comprised in Polypeptide Sequences Useful in Performing the Methods of the Invention The Integrated Resource of Protein Families, Domains and Sites (InterPro) database is an integrated interface for the commonly used signature databases for text- and sequence-based searches. The InterPro database combines these databases, which use different methodologies and varying degrees of biological information about well-characterized proteins to derive protein signatures. Collaborating databases include SWISS-PROT, PROSITE, TrEMBL, PRINTS, Pro-Dom and Pfam, Smart and TIGRFAMs. Pfam is a large collection of multiple sequence alignments and hidden Markov models covering many common protein domains and families. Pfam is hosted at the Sanger Institute server in the United Kingdom. Interpro is hosted at the European Bioinformatics Institute in the United Kingdom.

The results of the InterPro scan of the polypeptide sequence as represented by SEQ ID NO: 2 are presented in Table C.

TABLE C

InterPro scan results (major accession numbers) of the polypeptide sequence as represented by SEQ ID NO: 2.

| Database | Accession number | Accession name | Amino acid coordinates on SEQ ID NO 2 |
|---|---|---|---|
| PFAM | PF00076 | RRM_1 | 302-372 |
| SMART | SM00360 | RRM | 301-373 |
| PROFILE | PS50102 | RRM | 300-377 |
| PFAM | PF02136 | NTF2 | 17-133 |
| PROFILE | PS50177 | NTF2_DOMAIN | 17-133 |
| GENE3D | G3DSA: 3.30.70.330 | no description | 261-408 |
| GENE3D | G3DSA: 3.10.450.50 | no description | 8-139 |
| PANTHER | PTHR10693 | RNA-BINDING RAS-GAP SH3 BINDING PROTEIN RELATED | 24-460 |

Example 5

Topology Prediction of the Polypeptide Sequences Useful in Performing the Methods of the Invention TargetP 1.1 predicts the subcellular location of eukaryotic proteins. The location assignment is based on the predicted presence of any of the N-terminal pre-sequences: chloroplast transit peptide (cTP), mitochondrial targeting peptide (mTP) or secretory pathway signal peptide (SP). Scores on which the final prediction is based are not really probabilities, and they do not necessarily add to one. However, the location with the highest score is the most likely according to TargetP, and the relationship between the scores (the reliability class) may be an indication of how certain the prediction is. The reliability class (RC) ranges from 1 to 5, where 1 indicates the strongest prediction. TargetP is maintained at the server of the Technical University of Denmark.

For the sequences predicted to contain an N-terminal pre-sequence a potential cleavage site can also be predicted.

A number of parameters were selected, such as organism group (non-plant or plant), cutoff sets (none, predefined set of cutoffs, or user-specified set of cutoffs), and the calculation of prediction of cleavage sites (yes or no).

The results of TargetP 1.1 analysis of the polypeptide sequence as represented by SEQ ID NO: 2 are presented Table D. The "plant" organism group has been selected, no cutoffs defined, and the predicted length of the transit peptide requested. The subcellular localization of the polypeptide sequence as represented by SEQ ID NO: 2 may be the cytoplasm or nucleus, no transit peptide is predicted.

TABLE D

TargetP 1.1 analysis of the polypeptide sequence as represented by SEQ ID NO: 2

| Length (AA) | 488 |
|---|---|
| Chloroplastic transit peptide | 0.076 |
| Mitochondrial transit peptide | 0.179 |
| Secretory pathway signal peptide | 0.124 |
| Other subcellular targeting | 0.672 |
| Predicted Location | / |
| Reliability class | 3 |
| Predicted transit peptide length | / |

Many other algorithms can be used to perform such analyses, including:

ChloroP 1.1 hosted on the server of the Technical University of Denmark;

Protein Prowler Subcellular Localisation Predictor version 1.2 hosted on the server of the Institute for Molecular Bioscience, University of Queensland, Brisbane, Australia;

PENCE Proteome Analyst PA-GOSUB 2.5 hosted on the server of the University of Alberta, Edmonton, Alberta, Canada;

TMHMM, hosted on the server of the Technical University of Denmark

Example 6

Cloning of the Nucleic Acid Sequence Used in the Methods of the Invention

The nucleic acid sequence used in the methods of the invention was amplified by PCR using as template a custom-made *Oryza sativa* seedlings cDNA library (in pCMV Sport 6.0; Invitrogen, Paisley, UK). PCR was performed using Hifi Taq DNA polymerase in standard conditions, using 200 ng of template in a 50 μl PCR mix. The primers used were prm8784 (SEQ ID NO: 5; sense, start codon in bold): 5' ggggacaagtttg-tacaaaaaagcaggcttaaacaatggcagtgcaagctggaa 3'
and prm8783 (SEQ ID NO: 6; reverse, complementary): 5' ggggaccactttgtacaagaaagctgggtcatcattgccctcctctatgc 3', which include the AttB sites for Gateway recombination. The amplified PCR fragment was purified also using standard methods. The first step of the Gateway procedure, the BP reaction, was then performed, during which the PCR fragment recombines in vivo with the pDONR201 plasmid to produce, according to the Gateway terminology, an "entry clone", pGSBP-like. Plasmid pDONR201 was purchased from Invitrogen, as part of the Gateway® technology.

The entry clone comprising SEQ ID NO: 1 was then used in an LR reaction with a destination vector used for *Oryza sativa* transformation. This vector contained as functional elements within the T-DNA borders: a plant selectable marker; a screenable marker expression cassette; and a Gateway cassette intended for LR in vivo recombination with the nucleic acid sequence of interest already cloned in the entry clone. A rice GOS2 promoter (SEQ ID NO: 3) for root specific expression was located upstream of this Gateway cassette.

Figure 4:
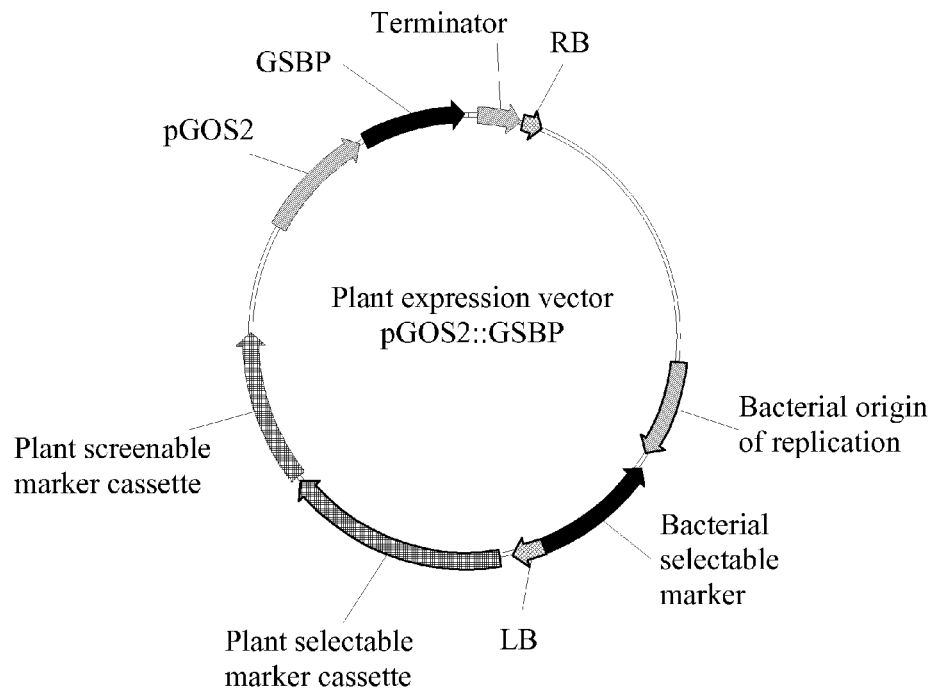
FIG. 4 represents the binary vector for increased expression in *Oryza sativa* of a GSBP-like protein-encoding nucleic acid under the control of a rice GOS2 promoter (pGOS2). A similar construct was created with the rice GSBP-like protein under control of the RCc3 promoter.

After the LR recombination step, the resulting expression vector pGOS2::GSBP-like (FIG. 4) was transformed into *Agrobacterium* strain LBA4044 according to methods well known in the art.

A second construct (pRCc3::GSBP-like) was made with the GSBP-like coding sequence under control of the RCc3 promoter (SEQ ID NO: 4) but otherwise identical to the pGOS2::GSBP-like vector and used for plant transformation.

Example 7

Plant Transformation

Rice Transformation

The *Agrobacterium* containing the expression vector was used to transform *Oryza sativa* plants. Mature dry seeds of the rice japonica cultivar Nipponbare were dehusked. Sterilization was carried out by incubating for one minute in 70% ethanol, followed by 30 minutes in 0.2% HgCl$_2$, followed by a 6 times 15 minutes wash with sterile distilled water. The sterile seeds were then germinated on a medium containing 2,4-D (callus induction medium). After incubation in the dark for four weeks, embryogenic, scutellum-derived calli were excised and propagated on the same medium. After two weeks, the calli were multiplied or propagated by subculture on the same medium for another 2 weeks. Embryogenic callus pieces were sub-cultured on fresh medium 3 days before co-cultivation (to boost cell division activity).

*Agrobacterium* strain LBA4404 containing the expression vector was used for co-cultivation. *Agrobacterium* was inoculated on AB medium with the appropriate antibiotics and cultured for 3 days at 28° C. The bacteria were then collected and suspended in liquid co-cultivation medium to a density (OD$_{600}$) of about 1. The suspension was then transferred to a Petri dish and the calli immersed in the suspension for 15 minutes. The callus tissues were then blotted dry on a filter paper and transferred to solidified, co-cultivation medium and incubated for 3 days in the dark at 25° C. Co-cultivated calli were grown on 2,4-D-containing medium for 4 weeks in the dark at 28° C. in the presence of a selection agent. During this period, rapidly growing resistant callus islands developed. After transfer of this material to a regeneration medium and incubation in the light, the embryogenic potential was released and shoots developed in the next four to five weeks. Shoots were excised from the calli and incubated for 2 to 3 weeks on an auxin-containing medium from which they were transferred to soil. Hardened shoots were grown under high humidity and short days in a greenhouse.

Approximately 35 independent T0 rice transformants were generated for one construct. The primary transformants were transferred from a tissue culture chamber to a greenhouse. After a quantitative PCR analysis to verify copy number of the T-DNA insert, only single copy transgenic plants that exhibit tolerance to the selection agent were kept for harvest of T1 seed. Seeds were then harvested three to five months after transplanting. The method yielded single locus transformants at a rate of over 50% (Aldemita and Hodges 1996, Chan et al. 1993, Hiei et al. 1994).

Corn Transformation

Transformation of maize (Zea mays) is performed with a modification of the method described by Ishida et al. (1996) Nature Biotech 14(6): 745-50. Transformation is genotype-dependent in corn and only specific genotypes are amenable to transformation and regeneration. The inbred line A188 (University of Minnesota) or hybrids with A188 as a parent are good sources of donor material for transformation, but other genotypes can be used successfully as well. Ears are harvested from corn plant approximately 11 days after pollination (DAP) when the length of the immature embryo is about 1 to 1.2 mm. Immature embryos are cocultivated with *Agrobacterium tumefaciens* containing the expression vector, and transgenic plants are recovered through organogenesis. Excised embryos are grown on callus induction medium, then maize regeneration medium, containing the selection agent (for example imidazolinone but various selection markers can be used). The Petri plates are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Wheat Transformation

Transformation of wheat is performed with the method described by Ishida et al. (1996) Nature Biotech 14(6): 745-50. The cultivar Bobwhite (available from CIMMYT, Mexico) is commonly used in transformation. Immature embryos are co-cultivated with *Agrobacterium tumefaciens* containing the expression vector, and transgenic plants are recovered through organogenesis. After incubation with *Agrobacterium*, the embryos are grown in vitro on callus induction medium, then regeneration medium, containing the selection agent (for example imidazolinone but various selection markers can be used). The Petri plates are incubated in the light at 25° C. for 2-3 weeks, or until shoots develop. The green shoots are transferred from each embryo to rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Soybean Transformation

Soybean is transformed according to a modification of the method described in the Texas A&M U.S. Pat. No. 5,164,310. Several commercial soybean varieties are amenable to transformation by this method. The cultivar Jack (available from the Illinois Seed foundation) is commonly used for transformation. Soybean seeds are sterilised for in vitro sowing. The hypocotyl, the radicle and one cotyledon are excised from seven-day old young seedlings. The epicotyl and the remaining cotyledon are further grown to develop axillary nodes. These axillary nodes are excised and incubated with *Agrobacterium tumefaciens* containing the expression vector. After the cocultivation treatment, the explants are washed and transferred to selection media. Regenerated shoots are excised and placed on a shoot elongation medium. Shoots no longer than 1 cm are placed on rooting medium until roots develop. The rooted shoots are transplanted to soil in the greenhouse. T1 seeds are produced from plants that exhibit tolerance to the selection agent and that contain a single copy of the T-DNA insert.

Rapeseed/Canola Transformation

Cotyledonary petioles and hypocotyls of 5-6 day old young seedling are used as explants for tissue culture and transformed according to Babic et al. (1998, Plant Cell Rep 17: 183-188). The commercial cultivar Westar (Agriculture Canada) is the standard variety used for transformation, but other varieties can also be used. Canola seeds are surface-sterilized for in vitro sowing. The cotyledon petiole explants with the cotyledon attached are excised from the in vitro seedlings, and inoculated with *Agrobacterium* (containing the expression vector) by dipping the cut end of the petiole explant into the bacterial suspension. The explants are then cultured for 2 days on MSBAP-3 medium containing 3 mg/l BAP, 3% sucrose, 0.7% Phytagar at 23° C., 16 hr light. After two days of co-cultivation with *Agrobacterium*, the petiole explants are transferred to MSBAP-3 medium containing 3 mg/l BAP, cefotaxime, carbenicillin, or timentin (300 mg/l) for 7 days, and then cultured on MSBAP-3 medium with cefotaxime, carbenicillin, or timentin and selection agent until shoot regeneration. When the shoots are 5-10 mm in length, they are cut and transferred to shoot elongation medium (MSBAP-0.5, containing 0.5 mg/l BAP). Shoots of about 2 cm in length are transferred to the rooting medium (MS0) for root induction. The rooted shoots are transplanted to soil in the greenhouse. T1 seeds are produced from plants that exhibit tolerance to the selection agent and that contain a single copy of the T-DNA insert.

Alfalfa Transformation

A regenerating clone of alfalfa (*Medicago sativa*) is transformed using the method of (McKersie et al., 1999 Plant Physiol 119: 839-847). Regeneration and transformation of alfalfa is genotype dependent and therefore a regenerating plant is required. Methods to obtain regenerating plants have been described. For example, these can be selected from the cultivar Rangelander (Agriculture Canada) or any other commercial alfalfa variety as described by Brown D C W and A Atanassov (1985. Plant Cell Tissue Organ Culture 4: 111-112). Alternatively, the RA3 variety (University of Wisconsin) has been selected for use in tissue culture (Walker et al., 1978 Am J Bot 65:654-659). Petiole explants are cocultivated with an overnight culture of *Agrobacterium tumefaciens* C58C1 pMP90 (McKersie et al., 1999 Plant Physiol 119: 839-847) or LBA4404 containing the expression vector. The explants are cocultivated for 3 d in the dark on SH induction medium containing 288 mg/L Pro, 53 mg/L thioproline, 4.35 g/L K2SO4, and 100 μm acetosyringinone. The explants are washed in half-strength Murashige-Skoog medium (Murashige and Skoog, 1962) and plated on the same SH induction medium without acetosyringinone but with a suitable selection agent and suitable antibiotic to inhibit *Agrobacterium* growth. After several weeks, somatic embryos are transferred to BOi2Y development medium containing no growth regulators, no antibiotics, and 50 g/L sucrose. Somatic embryos are subsequently germinated on half-strength Murashige-Skoog medium. Rooted seedlings were transplanted into pots and grown in a greenhouse. T1 seeds are produced from plants that exhibit tolerance to the selection agent and that contain a single copy of the T-DNA insert.

Example 8

Phenotypic Evaluation Procedure 8.1 Evaluation Setup

Approximately 35 independent T0 rice transformants were generated. The primary transformants were transferred from a tissue culture chamber to a greenhouse for growing and harvest of T1 seed. Five events (for the pGOS2::GSBP-like construct) or six events (for the pRCc3::GSBP-like construct), of which the T1 progeny segregated 3:1 for presence/absence of the transgene, were retained. For each of these events, approximately 10 T1 seedlings containing the transgene (hetero- and homo-zygotes) and approximately 10 T1 seedlings lacking the transgene (nullizygotes) were selected by monitoring visual marker expression. The transgenic plants and the corresponding nullizygotes were grown side-by-side at random positions. Greenhouse conditions were of shorts days (12 hours light), 28° C. in the light and 22° C. in the dark, and a relative humidity of 70%.

Five T1 events with the pGOS2::GSBP-like construct were further evaluated in the T2 generation following the same evaluation procedure as for the T1 generation but with more individuals per event. From the stage of sowing until the stage of maturity the plants were passed several times through a digital imaging cabinet. At each time point digital images (2048×1536 pixels, 16 million colours) were taken of each plant from at least 6 different angles.

Drought Screen

Plants from T2 seeds were grown in potting soil under normal conditions until they approached the heading stage. They were then transferred to a "dry" section where irrigation was withheld. Humidity probes were inserted in randomly chosen pots to monitor the soil water content (SWC). When SWC went below certain thresholds, the plants were automatically re-watered continuously until a normal level was reached again. The plants were then re-transferred again to normal conditions. The rest of the cultivation (plant maturation, seed harvest) was the same as for plants not grown under abiotic stress conditions. Growth and yield parameters are recorded as detailed for growth under normal conditions.

Nitrogen Use Efficiency Screen

Rice plants from T2 seeds are grown in potting soil under normal conditions except for the nutrient solution. The pots are watered from transplantation to maturation with a specific nutrient solution containing reduced N nitrogen (N) content, usually between 7 to 8 times less. The rest of the cultivation (plant maturation, seed harvest) is the same as for plants not grown under abiotic stress. Growth and yield parameters are recorded as detailed for growth under normal conditions.

8.2 Statistical Analysis: F Test

A two factor ANOVA (analysis of variants) was used as a statistical model for the overall evaluation of plant phenotypic characteristics. An F test was carried out on all the parameters measured of all the plants of all the events transformed with the gene of the present invention. The F test was carried out to check for an effect of the gene over all the transformation events and to verify for an overall effect of the gene, also known as a global gene effect. The threshold for significance for a true global gene effect was set at a 5% probability level for the F test. A significant F test value points to a gene effect, meaning that it is not only the mere presence or position of the gene that is causing the differences in phenotype.

Because two experiments with overlapping events were carried out, a combined analysis was performed. This is useful to check consistency of the effects over the two experiments, and if this is the case, to accumulate evidence from both experiments in order to increase confidence in the conclusion. The method used was a mixed-model approach that takes into account the multilevel structure of the data (i.e. experiment—event—segregants). P values were obtained by comparing likelihood ratio test to chi square distributions.

8.3 Parameters Measured

Biomass-Related Parameter Measurement

From the stage of sowing until the stage of maturity the plants were passed several times through a digital imaging cabinet. At each time point digital images (2048×1536 pixels, 16 million colours) were taken of each plant from at least 6 different angles.

The plant aboveground area (or leafy biomass) was determined by counting the total number of pixels on the digital images from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground. The above ground area is the area measured at the time point at which the plant had reached its maximal leafy biomass. The early vigour is the plant (seedling) aboveground area three weeks post-germination.

Early vigour was determined by counting the total number of pixels from aboveground plant parts discriminated from the background. This value was averaged for the pictures taken on the same time point from different angles and was converted to a physical surface value expressed in square mm by calibration. The results described below are for plants three weeks post-germination.

Seed-Related Parameter Measurements

The mature primary panicles were harvested, counted, bagged, barcode-labelled and then dried for three days in an oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. The number of filled seeds was determined by counting the number of filled husks that remained after the separation step. The total seed yield was measured by weighing all filled husks harvested from a plant. Total seed number per plant was measured by counting the number of husks harvested from a plant. Thousand Kernel Weight (TKW) is extrapolated from the number of filled seeds counted and their total weight. The Harvest Index (HI) in the present invention is defined as the ratio between the total seed yield and the above ground area ($mm^2$), multiplied by a factor $10^6$. The total number of flowers per panicle as defined in the present invention is the ratio between the total number of seeds and the number of mature primary panicles. The seed fill rate as defined in the present invention is the proportion (expressed as a %) of the number of filled seeds over the total number of seeds (or florets).

Example 9

Results of the Phenotypic Evaluation of the Transgenic Plants

For plants transformed with the pGOS2::GSBP-like construct or the pRCc3::GSBP-like construct and grown under non-stress conditions, an increase of more than 5% was observed for at least one of: aboveground biomass (AreaMax), total seed yield, number of filled seeds, and number of flowers per panicle.

For plants transformed with the pGOS2::GSBP-like construct or the pRCc3::GSBP-like construct and grown under conditions of drought stress, an increase of more than 5% was observed for at least one of: aboveground biomass (AreaMax), emergence vigour (early vigour), total seed yield, number of filled seeds, fill rate, harvest index, and of more than 2% for thousand kernel weight.

The invention claimed is:

1. A method for enhancing yield and/or biomass in a plant relative to a control plant, comprising:
transforming and expressing in a plant a nucleic acid encoding a GTPase activating protein SH3 domain binding protein-like (GSBP-like) polypeptide, and
selecting for a transgenic plant having increased yield and/or biomass relative to a control plant, wherein said GSBP-like polypeptide comprises the amino acid sequence of SEQ ID NO: 2.

2. The method of claim 1, wherein said enhanced yield and/or biomass comprises one or more of early vigour, increased yield, increased biomass, and/or increased seed yield relative to a control plant.

3. The method of claim 1, wherein said enhanced yield and/or biomass is obtained under non-stress conditions.

4. The method of claim 1, wherein said enhanced yield and/or biomass is obtained under drought stress conditions.

5. The method of claim 1, wherein said nucleic acid is operably linked to a promoter capable of driving expression of the nucleic acid in roots of a plant.

6. The method of claim 5, wherein said promoter is a constitutive promoter, a GOS2 promoter, or a GOS2 promoter from rice.

7. The method of claim 5, wherein said promoter is a root-specific promoter, a RCc3 promoter, or a RCc3 promoter from rice.

8. The method of claim 1, wherein said nucleic acid encoding said GSBP-like polypeptide is of plant origin.

9. A method for making a plant having one or more of increased yield, increased biomass and/or increased seed yield relative to a control plant, comprising:
(a) transforming and expressing a construct into plant cells, wherein the construct comprises:
(i) a nucleic acid encoding a GSBP-like polypeptide comprising the amino acid sequence of SEQ ID NO: 2;
(ii) one or more control sequences capable of driving expression of the nucleic acid of (i);
wherein the nucleic acid of part (i) and said one or more control sequences of part (ii) are operably linked;
(b) obtaining transgenic plants expressing said GSBP-like polypeptide from said transformed cells of step (a); and
(c) selecting for a transgenic plant from the transgenic plants of step (b) having one or more of increased yield, increased biomass and/or increased seed yield relative to a control plant.

10. A method for the production of a transgenic plant having one or more of increased yield, increased biomass, and/or increased seed yield relative to a control plant, comprising:
(i) transforming and expressing in plant cells a nucleic acid encoding a GSBP-like polypeptide comprising the amino acid sequence of SEQ ID NO: 2;
(ii) obtaining transgenic plants expressing said GSBP-like polypeptide from said transformed cells of step (i);
(iii) cultivating said transgenic plants of step (ii) under conditions promoting plant growth and development; and
(iv) selecting for a transgenic plant from the transgenic plants of step (iii) having one or more of increased yield, increased biomass, and/or increased seed yield relative to a control plant.

11. The method of claim 9, wherein one of said control sequences is a constitutive promoter, a GOS2 promoter, or a GOS2 promoter from rice.

12. The method of claim 9, wherein one of said control sequences is a root-specific promoter, a RCc3 promoter, or a RCc3 promoter from rice.

* * * * *